US006482594B2

(12) United States Patent
Gold et al.

(10) Patent No.: US 6,482,594 B2
(45) Date of Patent: Nov. 19, 2002

(54) SYSTEMATIC EVOLUTION OF LIGANDS BY EXPONENTIAL ENRICHMENT: PHOTOSELECTION OF NUCLEIC ACID LIGANDS

(75) Inventors: Larry Gold, Boulder, CO (US); Michael Willis, Louisville, CO (US); Tad Koch, Boulder, CO (US); Steven Ringquist, Lyons, CO (US); Kirk Jensen, Boulder, CO (US); Brent Atkinson, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 09/882,246

(22) Filed: Jun. 14, 2001

(65) Prior Publication Data

US 2002/0106652 A1 Aug. 8, 2002

Related U.S. Application Data

(62) Division of application No. 09/459,553, filed on Dec. 13, 1999, now Pat. No. 6,291,184, which is a division of application No. 09/093,293, filed on Jun. 8, 1998, now Pat. No. 6,001,577, which is a continuation of application No. 08/612,895, filed as application No. PCT/US94/10562 on Sep. 16, 1994, now Pat. No. 5,763,177, which is a continuation-in-part of application No. 08/143,564, filed on Oct. 25, 1993, and a continuation-in-part of application No. 08/123,935, filed on Sep. 17, 1993, now abandoned, which is a continuation-in-part of application No. 07/714,131, filed on Jun. 10, 1991, now Pat. No. 5,475,096, said application No. 08/143,564, is a continuation-in-part of application No. 07/714,131, which is a continuation-in-part of application No. 07/536,428, filed on Jun. 11, 1990, now abandoned, said application No. 08/143,564, is a continuation-in-part of application No. 07/931,473, filed on Aug. 17, 1992, now Pat. No. 5,270,163, which is a division of application No. 07/714,131.

(51) Int. Cl.$^7$ .................... C12Q 1/68; C12P 19/34; C07H 21/04; C07H 21/02; C07K 14/00

(52) U.S. Cl. .................... 435/6; 435/91.2; 536/23.1; 536/24.33; 536/25.4

(58) Field of Search .................... 435/6, 91.2; 536/23.1, 536/24.33, 25.4; 530/350

(56) References Cited

U.S. PATENT DOCUMENTS

| | | | |
|---|---|---|---|
| 5,035,996 A | | 7/1991 | Hartley |
| 5,270,163 A | | 12/1993 | Gold et al. |
| 5,472,841 A | * | 12/1995 | Jayasena et al. ............ 435/6 |
| 5,723,323 A | | 3/1998 | Kauffman et al. |
| 5,763,177 A | * | 6/1998 | Gold et al. ............... 435/6 |

FOREIGN PATENT DOCUMENTS

| | | |
|---|---|---|
| AU | 692469 | 11/1998 |
| GB | 2 183 661 A | 6/1987 |
| WO | WO 89/06694 | 7/1989 |
| WO | WO 91/19813 | 12/1991 |
| WO | WO 92/14843 | 9/1992 |
| WO | WO 93/05182 | 3/1993 |
| WO | WO 95/07364 | 3/1995 |

OTHER PUBLICATIONS

Allen et al. (1991) J. Biol. Chem. 266:6113–6119.
Barbier et al. (1984) Biochemistry 23:2933–9.
Bayley and Knowles (1977) Methods Enzymol. 46:69–115.
Beckett et al. (1988) J. Mol. Biol. 204:939–47.
Blatter et al. (1992) Nature 359:650–3.
Carey et al. (1983) Biochemistry 22:4723–4750.
Chen and Prusoff (1977) Biochemistry 16:3310–3315.
Czarnecki et al. (1979) Methods Enzymol. 56:642–52.
Dietz et al. (1987) J. Am. Chem. Soc. 109:1793–1797.
Dietz and Koch (1987) Photochem. Photobiol. 46:971–8.
Dietz and Koch (1989) Photochem. Photobiol. 49:121–9.
Eggen and Nathans (1969) J. Mol. Biol. 39:293–305.
Ellington & Szostak (1990) Abstracts of papers presented at the 1990 meeting on RNA Processing, Cold Spring Harbor Laboratory, Cold Spring Harbor, NY, p.
Evans et al. (1989) Biochemistry 28:713–20.
Farrar et al. (1991) Am. Chem. Soc., U.S. 30:3075–3082.
Favre (1990) in *Bioorganic Photochemistry, vol. 1: Photochemistry and the Nucleic Acids* (Morrison, H., Ed.) 379–425, John Wiley and Sons: New York.
Gott et al. (1991) Am. Chem. Soc., U.S. 30:6290–6295.
Groebe and Uhlenbeck (1988) Nucleic Acids Res. 16:11725–35.
Hanna et al. (1993) Nucleic Acids Res. 21:2073–9.
Hutchinson and Kohnlein (1980) Prog. Subcell. Biol. 7:1–42.

(List continued on next page.)

Primary Examiner—Stephanie W. Zitomer
(74) Attorney, Agent, or Firm—Swanson & Bratschun, LLC

(57) ABSTRACT

Methods to obtain nucleic acid ligands that photocrosslink to target molecules associated with a disease state are provided. The methods presented are variations on the photoSELEX methods for obtaining nucleic acid ligands. In one method, a candidate mixture of photocrosslinkable nucleic acids is contacted with a biological substance obtained from a source associated with a disease state suspected of containing a target molecule to form nucleic acid-target molecule complexes, the complexes are irradiated to form crosslinked complexes, the photocrosslinked complexes are partitioned from the remainder of the candidate mixture; and the nucleic acid ligands that photocrosslink to molecule are retained. These nucleic acids are then contacted with a second biological substance of the same type as the first, but obtained from a source not associated with a disease state. This removes nucleic acids with affinity to molecules that are not associated with the disease state. In another method, photocrosslinkable nucleic acids are not incorporated in the initial candidate mixture, but rather are incorporated in an enriched candidate mixture obtained by contacting a biological substance associated with a disease state containing a target molecule to form nucleic acid-target molecule complexes, partitioning the complexes away from the candidate mixture.

8 Claims, 35 Drawing Sheets

OTHER PUBLICATIONS

Ito et al. (1980) J. Am. Chem. Soc. 102:7535–40.
Ito et al. (1980) Photchem. Photobiol. 32:683–85.
Jensen et al. (1995) Proc. Natl. Acad. of Sci. USA 92:12220–24.
Joyce (1989) Gene 82:83–7.
Joyce & Inoue (1989) Nucleic Acids Research 17:711–13.
Katouzian–Safadi et al. (1991) Nucleic Acids Research 19:4937–41.
Katouzian–Safadi et al. (1991) Photochem. Photobiol. 53:611–15.
Khalili (1988) EMBO J. 7:1205–10.
Kinzler & Vogelstein (1989) Nucleic Acids Research 17:3645–53.
Kramer et al. (1974) J. Mol. Biol. 89:719–36.
Lee et al. (1991) J. Biol. Chem. 266:16478–84.
Levisohn & Spiegelman (1968) PNAS USA 60:866–72.
Levisohn & Spiegelman (1969) PNAS USA 63:805–11.
Lin and Riggs (1974) Proc. Natl. Acad. Sci. USA 71:947–51.
Ling et al. (1970) Virology 40:920–29.
Liu and Verdine (1992) Tetrahedron Letters 33:4265–68.
Mee (1987) in *Radiation Chemistry: Principles and Applications* 477–499 (Farhataziz and Rodgers, eds.), VCH Publishers, New York.
Milligan et al. (1987) Nucleic Acids Res. 15:8783–98.
Ogata and Gilbert (1977) Proc. Natl. Acad. Sci. USA 74:4973–76.
Oliphant et al. (1986) Gene 44:177–83.
Oliphant & Struhl (1987) Methods in Enzymology 155:568–83.
Oliphant & Struhl (1988) Nucleic Acids Research 16:7673–83.
Oliphant et al. (1989) Mol. Cell. Biol. 9:2944–49.
Rahn and Sellin (1982) Photochem. Photobiol. 35:459–65.
Rahn and Stafford (1979) Photochem. Photobiol. 30:449–54.
Robertson & Joyce (1990) Nature 344:467–68.
Rothman and Kearns (1967) Photochem. Photobiol. 6:775–78.
Saito et al. (1986) J. Org. Chem. 51:5148–53.
Saito and Sugiyama (1990) in *Bioorganic Photochemistry, vol. 1: Photochemistry and the Nucliec Acids,* (Morrison, H., Ed.) 317–340, John Wiley & Sons: New York.
Salvucci and Haley (1990) Planta 181:287–95.
Schneider et al. (1992) J. Mol. Biol. 228:862–69.
Shetlar (1980) Photochem. Photobiol. Rev. 5:105–97.
Sugiyama et al. (1993) J. Amer. Chem. Soc. 115:4443–48.
Szybalski (1974) Cancer Chemother. Rep. 58:539–57.
Talbot et al. (1990) Nucleic Acids Res. 18:3521–28.
Tanner et al. (1988) Biochemistry 27:8852–61.
Thiesen & Bach (1990) Nucleic Acids Research 18:3203–8.
Tuerk & Gold (1990) Science 249:505–510.
Weber (1967) Biochemistry 6:3144–54.
Weintraub (1973) Cold Spring Harbor Symp. Quant. Biol. 38:247–56.
Wick and Matthews (1991) J. Biol. Chem. 266:6106.
Wolfes et al. (1986) Eur. J. Biochem. 159:267–73.
Wower et al. (1988) Biochemistry 27:8114–21.
Wower et al. (1989) Biochemistry 28:1563–67.
Wyatt et al. (1992) Genes & Development 6:2542–53.

* cited by examiner

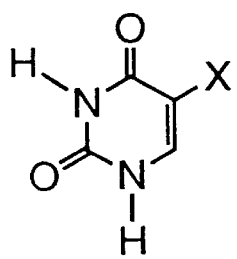  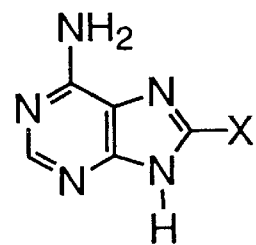
X=Br, 5-bromouracil   4-thiouracil   X=N₃, 8-azidoadenine
X=I, 5-iodouracil                    X=Br, 8-bromoadenine
X=N₃, 5-azidouracil
FIG. 1

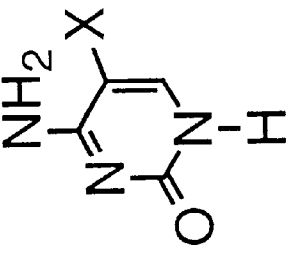
X=Br, 5-bromocytosine
X=I, 5-iodocytosine
X=CH₂=CHBr, 5-bromovinylcytosine
X=CH₂=CHI, 5-iodovinylcytosine
X=N₃, 5-azidocytosine
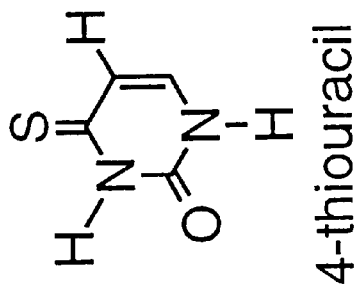
4-thiouracil
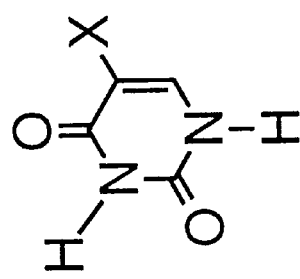
X=Br, 5-bromouracil
X=I, 5-iodouracil
X=CH₂=CHBr, 5-bromovinyluracil
X=CH₂=CHI, 5-iodovinyluracil
X=N₃, 5-azidouracil
FIG. 5

X=N$_3$, 8-azidoguanine
X=Br, 8-bromoguanine
X=I, 8-iodoguanine

X=N$_3$, 8-azidoxanthine
X=Br, 8-bromoxanthine
X=I, 8-iodoxanthine

X=N$_3$, 8-azidoadenine
X=Br, 8-bromoadenine
X=I, 8-iodoadenine

X=N$_3$, 8-azidohypoxanthine
X=Br, 8-bromohypoxanthine
X=I, 8-iodohypoxanthine

| | | SEQ ID NO: |
|---|---|---|
| 6a | agguagcauugagaaacacguuuguggacucucuguaucu | 5 | class 1 L1-XL

| | | | SEQ ID NO: |
|---|---|---|---|
| a: 49 | aguuacgauuAACAg--acgacUGUUaacggccuaccu | | 6 |
| 65 | uaacggcuuAACAagcaccauUGUUaaccuagugccu | | 7 |
| 11 | gaguggcuuAACAagcaccauUGUUaaccuaguaccu | | 8 |
| 25 | gugcagauuAACAacaac-guUGUUaacucccucucu | | 9 |
| *24 | cuguggauuAACAaggcacacCUGUUaaccguuaccu | + | 10 |
| 38 | cuguggauuAACAaggcacacCUGUUaaccguaccc | | 11 |
| 58 | agacgauuAACAAuccacggaUGUUaacgcgcuagaa | | 12 |
| 6 | aagacgauuAACAaaacacguUGUUaacgcaacaccu | – | 13 |
| 66 | gauuggauuAACAggcacccCUGUUaa--ccuaccacu | + | 14 |
| 45 | aggaggauuAACAaacaaaagguUGUUaacccguacca | | 15 |
| 40 | ugaaggauuAACAacuaaugUGUUaaccaugua | – | 16 |
| 52 | uugaggauuAACAggcacacCUGUcUaacgguuaccc | | 17 |
| 27 | auguggcuuAACAaguacgcuUGUUaacccaaaaacg | | 18 |
| 20 | aggacgauuAACAaacacguUGUUcacgccaugc | | 19 |
| 41 | gacuggcuuAACAaacauguUGUUaaccguguacca | + | 20 |
| 33 | cggcggauuAACAcgacacacucgcUGUuaccauauc | | 21 |

FIG. 16

|   | SEQ ID NO: |
|---|---|
| b : 17 | gcaucagaugaAACAgcacgucUGUUcacuaugcaccc | 22 |
| 57 | gcaucagaugaAACAgcacgucUGUUcacuaugcaccu | 23 |
| 42 | gcaucagaugaACAgcacgucUGUUcacuaugcaccu | 24 |
| 3 | caguauagaAACAccacgugUGUUccacuguaccu | 25 |
| 37 | caguuagaAACAacacguuUGUUccacugccu | 26 |
| 4 | gaguuagaAACAacacguuUGUUccacuccu | 27 |
| 36 | gaguuagaAACAacacguuUGUUccacugucu | 28 |
| 44 | gauuagaAACAacacguuUGUUccacucccu | 29 |
| 7 | gauuagaAACAacgugUGUUccacugccu | 30 |
| 51 | gauuggacuuAACAgacaccCUGUUaaccacu | 31 |
| c : 15 | ugccacaguuagaAACAcgauUGUUacuguaug | 32 |
| 47 | uacaggcuuaagaAACAcguuUGUUaaccaccccu | 33 |
| 14 | ucgagcaguguaAACAcgauuuGUUccugcuca | 34 |
| 62 | ugaugccuagaAACAcauuaqUGUUcccucugu | 35 |
| 54 | acgugccucuagaAACAcaucgaUGUUccccucuca | 36 |
| 56 | acccgcccugugaAACAcgcuuagUGUUcccucuca | 37 |
| 48 | cgguugacguuagaAACAcguucguUGUUccccu | 38 |
| 2 | gcuugcguuagaAACAcguuugacGUUcccu | 39 |
| 10 | gcacccuagaAACAcguuagagacGUUccccu | 40 |

FIG. 16 (CONT'D)

|  | SEQ ID NO: |  |
|---|---|---|
| d: 22 | aggaaccuagaAACAcacagUGUUccccucugcccac | 41 |
| 26 | gccugcauggauuAACAcguauGUUaaccgacucc | 42 |
| *18 | ugaAACAcugagaaacgUGUUccccuugugugau | 43 | class 2

| 61 | aGGAACCUCAAgccgcgccccuagaacacucggcaccu | 44 |
|---|---|---|
| 8 | aGGAACCUCAAgaaagcccugaacacucgaagccu | 45 |
| 53 | aGGAACCUCAAgaaacccugaacacucauuaccg | 46 |
| 39 | aGGAACCUCAAgaaauccgaacgacaaccuacaccu | 47 |
| 59 | aGGAACCUCAAgaaaacccgccacggaccccaacca | 48 |
| 35 | gGGAACCUCAAuaaaucacgcacgcauacggcaucu | 49 |
| 29 | gGGAACCUCAAgagacccgacaccaggauacucggac | 50 |
| 46 | aaguGGAACCUCAAucccguaagaagauccuguaccu | 51 |
| 9 | augugcauagagaugauauauGGAACCUCAGuagag | 52 |
| 5 | ucaugcauaggcauaggcagauGGAACCUCAGuagcc | 53 |
| 31 | augugcaacaaggcgcacgauaaGGAACCUCGAagu | 54 |
| 19 | gaguacagcacgcaacacguacggGGAACCUCAAagu | 55 |

FIG. 16 (CONT'D)

class 1 consensus

SEQ ID NO:56 class 2 consensus

SEQ ID NO:57

```
         C
      A     G
   C           iU
      C  ▪  G
      A  ▪ iU
      C  ▪  G
      A  ▪ iU
      A  ▪ iU
      A  ▪ iU
    G    ▪  C
 iU
A           |
 iU
      G  ▪  C
     iU  ▪  A
      G  ▪  C
      G  ▪ iU
      G  ▪  C
      5'    3'
``` trunc2

SEQ ID NO:58

FIG. 18A

```
      A C
   C      A
   G  ·  C
   G  ·  C
   A  ·  iU
   C  ·  G
   A  ·  iU
   A  ·  iU
  iU  ·  A
  iU  ·  A
   A     |
   G  ·  C
   G  ·  C
   G  ·  C
   G  ·  iU
   5'    3'
``` trunc24

SEQ ID NO:59

FIG. 19A

SEQUENCE LISTING (1) GENERAL INFORMATION:

(iii) NUMBER OF SEQUENCES: 64

(2) INFORMATION FOR SEQ ID NO: 1:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ix) FEATURE:
       (D) OTHER INFORMATION: U at position 13 is 5-
           bromouracil (xi) SEQUENCE DESCRIPTION: SEQ ID NO: 1:

GGGAGCGAGC AAUAGCCGC                                                19

(2) INFORMATION FOR SEQ ID NO: 2:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ix) FEATURE:
       (D) OTHER INFORMATION: U at position 13 is 5-
           iodouracil (xi) SEQUENCE DESCRIPTION: SEQ ID NO: 2:

GGGAGCGAGC AAUAGCCGC                                                19

(2) INFORMATION FOR SEQ ID NO: 3:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ix) FEATURE:
       (D) OTHER INFORMATION: U at position 13 has
           hydrogen molecule attached (xi) SEQUENCE DESCRIPTION: SEQ ID NO: 3:

GGGAGCGAGC AAUAGCCGC                                                19

(2) INFORMATION FOR SEQ ID NO: 4:

(i) SEQUENCE CHARACTERISTICS:
       (A) LENGTH: 44 base pairs
       (B) TYPE: nucleic acid
       (C) STRANDEDNESS: single
       (D) TOPOLOGY: linear (ix) FEATURE:
       (D) OTHER INFORMATION: all U are 5-iodouracil (xi) SEQUENCE DESCRIPTION: SEQ ID NO: 4:

GAACAUGAGG AUUACCCAUG AAUUCGAGCU CGCCCGGGCU CUAG                     44

(2) INFORMATION FOR SEQ ID NO: 5:

(i) SEQUENCE CHARACTERISTICS:
       (A) LENGTH: 37 base pairs (B) TYPE: nucleic acid
        (C) STRANDEDNESS: single
        (D) TOPOLOGY: linear (xi) SEQUENCE DESCRIPTION: SEQ ID NO: 5:

GGGUGCAUUG AGAAACACGU UUGUGGACUC UGUAUCU                                37

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 6:

AGGUACGAUU AACAGACGAC UGUUAACGGC CUACCU                                 36

(2) INFORMATION FOR SEQ ID NO: 7

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 7:

UAACGGCUUA ACAAGCACCA UUGUUAACCU AGUGCCU                                37

(2) INFORMATION FOR SEQ ID NO: 8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 8:

GAGUGGCUUA ACAAGCACCA UUGUUAACCU AGUACCU                                37

(2) INFORMATION FOR SEQ ID NO: 9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 9:

GUGCAGAUUA ACAACAACGU UGUUAACUCC UCCUCU                                 36

(2) INFORMATION FOR SEQ ID NO: 10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 10:

CUGUGGAUUA ACAGGCACAC CUGUUAACCG UGUACCU                                37

(2) INFORMATION FOR SEQ ID NO: 11:

(i) SEQUENCE CHARACTERISTICS:
        (A) LENGTH: 37 base pairs
        (B) TYPE: nucleic acid (C) STRANDEDNESS: single
        (D) TOPOLOGY: linear (xi) SEQUENCE DESCRIPTION: SEQ ID NO: 11:

CUGUGGAUUA ACAGGCACAC CUGUUAACCG UGUACCC                                37

(2) INFORMATION FOR SEQ ID NO: 12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 12:

AGACGAUUAA CAUCCACGGA UGUUAACGCG CUAGAA                                 36

(2) INFORMATION FOR SEQ ID NO: 13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 13:

AAGACGAUUA ACAAACACGU UUGUUAACGC AACACCU                                37

(2) INFORMATION FOR SEQ ID NO: 14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 14:

GAUUGGAUUA ACAGGCACCC CUGUUAACCU ACCACU                                 36

(2) INFORMATION FOR SEQ ID NO: 15:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 15:

AGGAGGAUUA ACAACAAAGG UUGUUAACCC CGUACCA                                37

(2) INFORMATION FOR SEQ ID NO: 16:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 16:

UGAAGGAUUA ACAACUAAUG UUGUUAACCA UGUA                                   34

(2) INFORMATION FOR SEQ ID NO: 17:

(i) SEQUENCE CHARACTERISTICS:
        (A) LENGTH: 37 base pairs
        (B) TYPE: nucleic acid
        (C) STRANDEDNESS: single (D) TOPOLOGY: linear (xi) SEQUENCE DESCRIPTION: SEQ ID NO: 17:

UUGAGGAUUA ACAGGCACAC CUGCUAACCG UGUACCC                                    37

(2) INFORMATION FOR SEQ ID NO: 18:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO: 18:

AUGUGGCUUA ACAAGUACGC UUGUUAACCC AAAAACG                                    37

(2) INFORMATION FOR SEQ ID NO: 19:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO: 19:

AGGACGAUGA ACAAACACGU UUGUUCACGC CAUGC                                      35

(2) INFORMATION FOR SEQ ID NO: 20:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO: 20:

GACUGGCUUA ACAAACAUGU UUUGUUAACC GUGUACCA                                   38

(2) INFORMATION FOR SEQ ID NO: 21:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO: 21:

CGGCGGAUUA ACACGACACA CUCGUGUUAA CCAUAUC                                    37

(2) INFORMATION FOR SEQ ID NO: 22:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO: 22:

GCAUCAGAUG AACAGCACGU CUGUUCACUA UGCACCC                                    37

(2) INFORMATION FOR SEQ ID NO: 23:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO: 23:

GCAUCAGAUG AACAGCACGU CUGUUCACUA UGCACCU         37

(2) INFORMATION FOR SEQ ID NO: 24:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 24:

GCAUCAGAUG GACAGCACGU CUGUUCACUA UGCACCU         37

(2) INFORMATION FOR SEQ ID NO: 25:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 25:

CAGUGUAUGA AACACCACGU GUGUUUCCAC UGUACCU         37

(2) INFORMATION FOR SEQ ID NO: 26:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 26:

CAGUGUAUGA AACAACACGU UUGUUUCCAC UGCCU           35

(2) INFORMATION FOR SEQ ID NO: 27:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 27:

GAGUGUAUGA AACAACACGU UUGUUUCCAC UCCCU           35

(2) INFORMATION FOR SEQ ID NO: 28:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 28:

GAGUGUAUGA AACAACACGU UUGUUUCCAC UGUCU           35

(2) INFORMATION FOR SEQ ID NO: 29:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 29:

GAUUGUAUGA AACAACGUGU UUGUUUCCAC UCCCU     35

(2) INFORMATION FOR SEQ ID NO: 30:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 30:

GAAUGUAUGA AACAACACGU UUGUUUCCAC UGCCU     35

(2) INFORMATION FOR SEQ ID NO: 31:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 31:

GAUUGGACUU AACAGACACC CCUGUUAACC UACCACU     37

(2) INFORMATION FOR SEQ ID NO: 32:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 32:

UGCGACAGUU AGAAACACGA UUGUUUACUG UAUG     34

(2) INFORMATION FOR SEQ ID NO: 33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 33:

UACAGGCUUA AGAAACACGU UUGUUAACCA ACCCCU     36

(2) INFORMATION FOR SEQ ID NO: 34:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 34:

UCGAGCAGUG UGAAACACGA UUGUGUUUCC UGCUCA     36

(2) INFORMATION FOR SEQ ID NO: 35:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 35:

UGAUGCCUAG AGAAACACAU UAGUGUUUCC CUCUGU                                36

(2) INFORMATION FOR SEQ ID NO: 36:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 36:

ACGUGCCUCU AGAAACACAU CUGAUGUUUC CCUCUCA                               37

(2) INFORMATION FOR SEQ ID NO: 37:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 37:

ACCCGCCUCG UGAAACACGC UUGAUGUUUC CCUCUCA                               37

(2) INFORMATION FOR SEQ ID NO: 38:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 38:

CGGUGACGUA UGAAACACGU UCGUUGAUUU CCGU                                  34

(2) INFORMATION FOR SEQ ID NO: 39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 39:

GCUUGCGAAA CACGUUUGAC GUGUUUCCCU                                       30

(2) INFORMATION FOR SEQ ID NO: 40:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 40:

GCACCCUAGA AACGCGUUAG UAGACGUUUC CCU                                   33

(2) INFORMATION FOR SEQ ID NO: 41:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 41:

AGGAACCUAG AAACACACAG UGUUUCCCUC UGCCCAC                                37

(2) INFORMATION FOR SEQ ID NO: 42:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 42:

GCCUGCAUGG AUUAACACGU AUGUGUUAAC CGACUCC                                37

(2) INFORMATION FOR SEQ ID NO: 43:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 43:

UGAAACACUG AGAAACACGU GUUUCCCCUU GUGUGAU                                37

(2) INFORMATION FOR SEQ ID NO: 44:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 44:

AGGAACCUCA AGCCGCCCCU AGAACACUCG GCACCU                                 36

(2) INFORMATION FOR SEQ ID NO: 45:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 45:

AGGAACCUCA AGAAAGCCCC UGAAACACUC GAAGCCU                                37

(2) INFORMATION FOR SEQ ID NO: 46:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 46:

AGGAACCUCA AGAAACCCCC UGAAACACUC AUUACCG                                37

(2) INFORMATION FOR SEQ ID NO: 47:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 47:

AGGAACCUCA AGAAAUCCGA ACGACAACCC UACACCU                                37

(2) INFORMATION FOR SEQ ID NO: 48:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 48:

AGGAACCUCA AGAAACCCCG CCACGGACCC CAACCA                      36

(2) INFORMATION FOR SEQ ID NO: 49:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 49:

GGGAACCUCA AUAAUCACGC ACGCAUACUC GGCAUCU                     37

(2) INFORMATION FOR SEQ ID NO: 50:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 50:

GGGAACCUCA AGAGACCCGA CAGGAUACUC GGAC                        34

(2) INFORMATION FOR SEQ ID NO: 51:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 51:

AAGUGGAACC UCAAUCCCGU AAGAAGAUCC UGUACCU                     37

(2) INFORMATION FOR SEQ ID NO: 52:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 52:

AUGUGCAUAG AGAUGUACAU AUGAAACCUC AGUAGAG                     37

(2) INFORMATION FOR SEQ ID NO: 53:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 53:

UCAUGCAUAG GCAUAGGCAG AUGGAACCUC AGUAGCC                     37

(2) INFORMATION FOR SEQ ID NO: 54:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 54:

AUGUGCAACA AGGCGCACGG AUAAGGAACC UCGAAGU                  37

(2) INFORMATION FOR SEQ ID NO: 55:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 55:

GAGUACAGCA CGCAACACGU ACGGGGAACC UCAAAGU                  37

(2) INFORMATION FOR SEQ ID NO: 56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (D) OTHER INFORMATION: N at positions 1 and 20
            indicates 1-2 complementary base pairs (ix) FEATURE:
        (D) OTHER INFORMATION: N at position 3 indicates 1
            or 3 nucleotides (ix) FEATURE:
        (D) OTHER INFORMATION: N at positions 10 and 12
            indicates 1-4 complementary base pairs (ix) FEATURE:
        (D) OTHER INFORMATION: N at position 11 indicates 4
            or 5 nucleotides (ix) FEATURE:
        (D) OTHER INFORMATION: U is iodouracil (xi) SEQUENCE DESCRIPTION: SEQ ID NO: 56:

NGNKDAACAN NNUGUUHMCN                                    20

(2) INFORMATION FOR SEQ ID NO: 57:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (D) OTHER INFORMATION: U is iodouracil (xi) SEQUENCE DESCRIPTION: SEQ ID NO: 57:

GGAACCUCAA UUGAUGGCCU UCC                            23

(2) INFORMATION FOR SEQ ID NO: 58:

(i) SEQUENCE CHARACTERISTICS:
        (A) LENGTH: 32 base pairs (B) TYPE: nucleic acid
        (C) STRANDEDNESS: single
        (D) TOPOLOGY: linear (ix) FEATURE:
        (D) OTHER INFORMATION: U is iodouracil (xi) SEQUENCE DESCRIPTION: SEQ ID NO: 58:

GGGUGUAUGA AACACCACGU GUGUUUCCAC UC                                32

(2) INFORMATION FOR SEQ ID NO: 59:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 59:

GGGGAUUAAC AGGCACACCU GUUAACCCU                                   29

(2) INFORMATION FOR SEQ ID NO: 60:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 60:

TAATACGACT CACTATA                                                17

(2) INFORMATION FOR SEQ ID NO: 61:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO: 61:

GAGTGGAAAC ACACGTGGTG TTTCATACAC CCTATAGTGA GTCGTATTA             49

(2) INFORMATION FOR SEQ ID NO: 62:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO: 62:

AGGGTTAACA GGTGTGCCTG TTAATCCCCT ATAGTGAGTC GTATTA                46

(2) INFORMATION FOR SEQ ID NO: 63:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO: 63:

CTAGAGCCCG GGC                                                    13

(2) INFORMATION FOR SEQ ID NO: 64:

-continued (i) SEQUENCE CHARACTERISTICS:
    (A) LENGTH: 44 base pairs
    (B) TYPE: nucleic acid
    (C) STRANDEDNESS: single
    (D) TOPOLOGY: linear (xi) SEQUENCE DESCRIPTION: SEQ ID NO: 64:

CTAGAGCCCG GGCGAGCTCG AATTCATGGG TAATCCTCAT GTTC            44

SYSTEMATIC EVOLUTION OF LIGANDS BY EXPONENTIAL ENRICHMENT: PHOTOSELECTION OF NUCLEIC ACID LIGANDS

This application is a Divisional of U.S. patent application Ser. No. 09/459,553, filed Dec. 13, 1999, entitled "Systematic Evolution of Ligands by Exponential Enrichment: Photoselection of Nucleic Acid Ligands and Solution Selex," now U.S. Pat. No. 6,291,184, which is a Divisional of U.S. patent application Ser. No. 09/093,293, filed Jun. 8, 1998, now U.S. Pat. No. 6,001,577, entitled "Systematic Evolution of Ligands by Exponential Enrichment: Photoselection of Nucleic Acid Ligands and Solution Selex," which is a Continuation of U.S. patent application Ser. No. 08/612,895, filed Mar. 8, 1996, now U.S. Pat. No. 5,763,177, which is a 35 U.S.C. §371 filing of PCT/US94/10562 (WO 95/08003), filed Sep. 16, 1994, entitled "Systematic Evolution of Ligands by Exponential Enrichment: Photoselection of Nucleic Acid Ligands and Solution Selex," which is a Continuation-in-Part of U.S. patent application Ser. No. 08/123,935, filed Sep. 17, 1993, entitled "Photoselection of Nucleic Acid Ligands," now abandoned in favor of U.S. patent application Ser. No. 08/443,959, filed May 18, 1995, now abandoned, and a Continuation-in-Part of U.S. patent application Ser. No. 08/143,564, filed Oct. 25, 1993, entitled "Systematic Evolution of Ligands by Exponential Enrichment: Solution SELEX," now abandoned. U.S. patent application Ser. Nos. 08/123,935 and 08/143,564 are Continuations-in-Part of U.S. patent application Ser. No. 07/714,131, filed Jun. 10, 1991, entitled "Nucleic Acid Ligands," now U.S. Pat. No. 5,475,096, which is a Continuation-in-Part of U.S. patent application Ser. No. 07/536,428, filed Jun. 11, 1990, entitled "Systematic Evolution of Ligands by EXponential Enrichment," now abandoned. U.S. patent application Ser. No. 08/143,564 is also a continuation-in-part of U.S. patent application Ser. No. 07/931,473, filed Aug. 17, 1992, entitled "Methods for Identifying Nucleic Acid Ligands," now U.S. Pat. No. 5,270,163, which is a divisional of U.S. patent application Ser. No. 07/714,131.

This work was supported by grants from the United States Government funded through the National Institutes of Health. The U.S. Government has certain rights in this invention.

FIELD OF THE INVENTION

This invention relates, in part, to a method for selecting nucleic acid ligands which bind and/or photocrosslink to and/or photoinactivate a target molecule. The target molecule may be a protein, pathogen or toxic substance, or any biological effector. The nucleic acid ligands of the present invention contain photoreactive or chemically reactive groups and are useful, inter alia, for the diagnosis and/or treatment of diseases or pathological or toxic states.

The underlying method utilized in this invention is termed SELEX, an acronym for Systematic Evolution of Ligands by EXponential enrichment. An improvement of the SELEX method herein described, termed Solution SELEX, allows more efficient partitioning between oligonucleotides having high and low affinity for a target molecule. An improvement of the high affinity nucleic acid products of SELEX are useful for any purpose to which a binding reaction may be put, for example in assay methods, diagnostic procedures, cell sorting, as inhibitors of target molecule function, as therapeutic agents, as probes, as sequestering agents and the like.

BACKGROUND OF THE INVENTION

The SELEX method (hereinafter termed SELEX), described in U.S. patent application Ser. No. 07/536,428, filed Jun. 11, 1990, entitled "Systematic Evolution of Ligands By Exponential Enrichment," now abandoned, U.S. patent application Ser. No. 07/714,131, filed Jun. 10, 1991, entitled "Nucleic Acid Ligands," issued as U.S. Pat. No. 5,475,096 and U.S. patent application Ser. No. 07/931,473, filed Aug. 17, 1992, entitled "Methods for Identifying Nucleic Acid Ligands," issued as U.S. Pat. No. 5,270,163, all of which are herein specifically incorporated by reference (referred to herein as the SELEX Patent Applications), provides a class of products which are nucleic acid molecules, each having a unique sequence, each of which has the property of binding specifically to a desired target compound or molecule. Each nucleic acid molecule is a specific ligand of a given target compound or molecule. SELEX is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size can serve as targets.

The SELEX method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by theory, SELEX is based on the inventors' insight that within a nucleic acid mixture containing a large number of possible sequences and structures there is a wide range of binding affinities for a given target. A nucleic acid mixture comprising, for example a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection, partition and amplification are repeated until a desired goal is achieved. In the most general case, selection/partition/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/partition/amplification iterations.

Photocrosslinking of nucleic acids to proteins has been achieved through incorporation of photoreactive functional groups in the nucleic acid. Photoreactive groups which have been incorporated into nucleic acids for the purpose of photocrosslinking the nucleic acid to an associated protein include 5-bromouracil, 4-thiouracil, 5-azidouracil, and 8-azidoadenine (see FIG. 1).

Bromouracil has been incorporated into both DNA and RNA by substitution of bromodeoxyuracil (BrdU) and bromouracil (BrU) for thyrnine and uracil, respectively. BrU-RNA has been prepared with 5-bromouridine triphosphate in place of uracil using T7 RNA polymerase and a DNA template, and both BrU-RNA and BrdU-DNA have been prepared with 5-bromouracil and 5-bromodeoxyuracil phosphoramidites, respectively, in standard nucleic acid synthesis (Talbot et al. (1990) Nucleic Acids Res. 18:3521). Some examples of the photocrosslinking of BrdU-substituted DNA to associated proteins are as follows: BrdU-substituted DNA to proteins in intact cells (Weintraub (1973) Cold Spring Harbor Symp. Quant. Biol. 38:247); BrdU-substituted lac operator DNA to lac repressor (Lin and Riggs (1974) Proc. Natl. Acad. Sci. U.S.A. 71:947; Ogata and Gilbert (1977) Proc. Natl. Acad. Sci. U.S.A. 74:4973; Barbier et al. (1984) Biochemistry 23:2933; Wick and Matthews (1991) J. Biol. Chem. 266:6106); BrdU-substituted DNA to EcoRI and EcoRV restriction endonucleases (Wolfes et al. (1986) Eur. J. Biochem. 159:267); *Escherichia coli* BrdU-substituted DNA to cyclic adenosine 3',5'-monophosphate receptor protein (Katouzian-Safadi et al. (1991) Photochem. Photobiol. 53:611); BrdU-substituted DNA oligonucleotide of human polyomavirus to proteins from human fetal brain extract (Khalili et al. (1988) EMBO J. 7:1205); a yeast BrdU-substituted DNA oligonucleotide to GCN4, a yeast transcriptional activator (Blatter et al. (1992) Nature 359:650); and a BrdU-substituted DNA oligonucleotide of Methanosarcina sp CHT155 to the chromosomal protein Mc1 (Katouzian-Safadi et al. (1991) Nucleic Acids Res. 19:4937). Photocrosslinking of BrU-substituted RNA to associated proteins has also been reported: BrU-substituted yeast precursor tRNA$^{Phe}$ to yeast tRNA ligase (Tanner et al. (1988) Biochemistry 27:8852) and a BrU-substituted hairpin RNA of the R17 bacteriophage genome to R17 coat protein (Gott et al. (1991) Biochemistry 30:6290).

4-Thiouracil-substituted RNA has been used to photocrosslink, especially, t-RNA's to various associated proteins (Favre (1990) in: *Bioorganic Photochemistry, Volume 1: Photochemistry and the Nucleic Acids*, H. Morrison (ed.), John Wiley & Sons: New York, pp. 379–425; Tanner et al. (1988) supra). 4-Thiouracil has been incorporated into RNA using 4-thiouridine triphosphate and T7 RNA polymerase or using nucleic acid synthesis with the appropriate phosphoramidite; it has also been incorporated directly into RNA by exchange of the amino group of cytosine for a thiol group with hydrogen sulfide. Yet another method of site specific incorporation of photoreactive groups into nucleic acids involves use of 4-thiouridylyl-(3'–5')-guanosine (Wyatt et al. (1992) Genes & Development 6:2542).

Examples of 5-azidouracil-substituted and 8-azidoadenine- substituted nucleic acid photocrosslinking to associated proteins are also known. Associated proteins that have been crosslinked include terminal deoxynucleotidyl transferase (Evans et al. (1989) Biochemistry 28:713; Farrar et al. (1991) Biochemistry 30:3075); Xenopus TFIUA, a zinc finger protein (Lee et al. (1991) J. Biol. Chem. 266:16478); and *E. coli* ribosomal proteins (Wower et al. (1988) Biochemistry 27:8114). 5-Azidouracil and 8-azidoadenine have been incorporated into DNA using DNA polymerase or terminal transferase. Proteins have also been photochemically labelled by exciting 8-azidoadenosine 3',5'-biphosphate bound to bovine pancreatic ribonuclease A (Wower et al. (1989) Biochemistry 28:1563) and 8-azidoadenosine 5'-triphosphate bound to ribulose-bisphosphate carboxylase/oxygenase (Salvucci and Haley (1990) Planta 181:287).

8-Bromo-2'-deoxyadenosine as a potential photoreactive group has been incorporated into DNA via the phosphoramidite (Liu and Verdine (1992) Tetrahedron Lett. 33:4265). The photochemical reactivity has yet to be investigated.

Photocrosslinking of 5-iodouracil-substituted nucleic acids to associated proteins has not been previously investigated, probably because the size of the iodo group has been thought to preclude specific binding of the nucleic acid to the protein of interest. However, 5-iodo-2'-de-oxyuracil and 5-iodo-2'-deoxyuridine triphosphate have been shown to undergo photocoupling to thymidine kinase from *E. coli* (Chen and Prusoff (1977) Biochemistry 16:33 10).

Mechanistic studies of the photoehemical reactivity of the 5-bromouracil chromophore have been reported including studies with regard to photocrosslinking. Most importantly, BrU shows wavelength dependent photochemistry. Irradiation in the region of 310 nm populates an n,π* singlet state which decays to ground state and intersystem crosses to the lowest energy triplet state (Dietz et al. (1987) J. Am. Chem. Soc. 109:1793), most likely the π,π* triplet (Rothman and Kearns (1967) Photochem. Photobiol. 6:775). The triplet state reacts with electron-rich amino acid residues via initial electron transfer followed by covalent bond formation. Photocrosslinking of triplet 5-bromouracil to the electron rich aromatic amino acid residues tyrosine, tryptophan and histidine (Ito et al. (1980) J. Am. Chem. Soc. 102:7535; Dietz and Koch (1987) Photochem. Photobiol. 46:971), and the disulfide bearing amino acid, cystine (Dietz and Koch (1989) Photochem. Photobiol. 49:121), has been demonstrated in model studies. Even the peptide linkage is a potential functional group for photocrosslinking to triplet BrU (Dietz et al. (1987) supra). Wavelengths somewhat shorter than 308 nm populate both the n,π* and π,π* singlet states. The π,π* singlet undergoes carbon-bromine bond homolysis as well as intersystem crossing to the triplet manifold (Dietz et al. (1987) supra); intersystem crossing may occur in part via internal conversion to the n,π* singlet state. Carbon-bromine bond homolysis likely leads to nucleic acid strand breaks (Hutchinson and Köhnlein (1980) Prog. Subcell. Biol. 7:1; Shetlar (1980) Photochem. Photobiol. Rev. 5:105; Saito and Sugiyama (1990) in: *Bioorganic Photochemistry, Volume 1: Photochemistry and the Nucleic Acids*, H. Morrison, ed., John Wiley and Sons, New York, pp. 317–378). The wavelength dependent photochemistry is outlined in the Jablonski Diagram in FIG. 2 and the model photocrosslinking reactions are shown in FIG. 3.

The location of photocrosslinks from irradiation of some BrU-substituted nucleoprotein complexes have been investigated. In the lac repressor-BrdU-lac operator complex a crosslink to tyrosine-17 has been established (Allen et al. (1991) J. Biol. Chem. 266:6113). in the archaebacterial chromosomal protein MC1-BrdU-DNA complex a crosslink to tryptophan-74 has been implicated. In yeast BrdU-substituted DNA-GCN4 yeast transcriptional activator a crosslink to alanine-238 was reported (Blatter et al. (1992) supra). In this latter example the nucleoprotein complex was irradiated at 254 nm which populated initially the $\pi,\pi^*$ singlet state.

The results of some reactivity and mechanistic studies of 5-iodouracil, 5-iodo-2'-deoxyuracil, 5-iodo-2'-deoxyuracil-substituted DNA, and 5-iodo-2'-deoxycytosine-substituted DNA have been reported. 5-Iodouracil and 5-iodo-2'-deoxyuracil couple at the 5-position to allylsilanes upon irradiation in acetonitrile-water bearing excess silane with emission from a medium pressure mercury lamp filtered through Pyrex glass; the mechanism was proposed to proceed through initial carbon-iodine bond homolysis followed by radical addition to the $\pi$-bond of the allylsilane (Saito et al. (1986) J. Org. Chem. 51:5148).

Aerobic and anaerobic photo-deiodination of 5-iodo-2'-deoxyuracil-substituted DNA has been studied as a function of excitation wavelength; the intrinsic quantum yield drops by a factor of 4 with irradiation in the region of 313 nm relative to the quantum yield with irradiation in the region of 240 nm. At all wavelengths the mechanism is proposed to involve initial carbon-iodine bond homolysis (Rahn and Sellin (1982) Photochem. Photobiol. 35:459). Similarly, carbon-iodine bond homolysis is proposed to occur upon irradiation of 5-iodo-2'-deoxycytidine-substituted DNA at 313 nm (Rahn and Stafford (1979) Photochem. Photobiol. 30:449). Strictly monochromatic light was not used in any of these studies. Recently, a 5-iodouracil-substituted duplex DNA was shown to undergo a photochemical single strand break (Sugiyama et al. (1993) J. Am. Chem. Soc. 115:4443).

Also of importance with respect to the present invention is the observed direct population of the triplet states of 5-bromouracil and 5-iodouracil from irradiation of the respective $S_o \rightarrow T$ absorption bands in the region of 350–400 nm (Rothman and Kearns (1967) supra).

Photophysical studies of the 4-thiouracil chromophore implicate the $\pi,\pi^*$ triplet state as the reactive state. The intersystem crossing quantum yield is unity or close to unity. Although photocrosslinking within 4-thiouracil-substituted nucleoprotein complexes has been observed, amino acid residues reactive with excited 4-thiouracil have not been established (Favre (1990) supra). The addition of the a-amino group of lysine to excited 4-thiouracil at the 6-position has been reported; however, this reaction is not expected to be important in photocrosslinking within nucleoprotein complexes because the a-amino group is involved in a peptide bond (Ito et al. (1980) Photochem. Photobiol. 32:683).

Photocrosslinking of azide-bearing nucleotides or nucleic acids to associated proteins is thought to proceed via formation of the singlet and/or triplet nitrene (Bayley and Knowles (1977) Methods Enzymol. 46:69; Czarnecki et al. (1979) Methods Enzymol. 56:642; Hanna et al. (1993) Nucleic Acids Res. 21:2073). Covalent bond formation results from insertion of the nitrene in an O—H, N—H, S—H or C—H bond. Singlet nitrenes preferentially insert in heteroatom-H bonds and triplet nitrenes in C—H bonds. Singlet nitrenes can also rearrange to azirines which are prone to nucleophilic addition reactions. If a nucleophilic site of a protein is adjacent, crosslinking can also occur via this pathway. A potential problem with the use of an azide functional group results if it resides ortho to a ring nitrogen; the azide will exist in equilibrium with a tetrazole which is much less photoreactive.

The coat protein-RNA hairpin complex of the R17 bacteriophage is an ideal system for the study of nucleic acid-protein photocrosslinking because of the simplicity of the system in vitro. The system is well characterized, consisting of a viral coat protein that binds with high affinity to an RNA hairpin within the phage genome. In vivo the interaction of the coat protein with the RNA hairpin plays two roles during phage infection: the coat protein acts as a translational repressor of replicase synthesis (Eggen and Nathans (1969) J. Mol. Biol. 39:293), and the complex serves as a nucleation site for encapsidation (Ling et al. (1970) Virology 40:920; Beckett et al. (1988) J. Mol Biol. 204:939). Many variations of the wild-type hairpin sequence also bind to the coat protein with high affinity (Tuerk & Gold (1990) Science 249:505; Gott et al. (1991) Biochemistry 30:6290, Schneider et al. (1992) J. Mol. Biol. 228:862).

The selection of nucleic acid ligands according to the SELEX method may be accomplished in a variety of ways, such as on the basis of physical characteristics. Selection on the basis of physical characteristics may include physical structure, electrophoretic mobility, solubility, and partitioning behavior. U. S. patent application Ser. No. 07/960,093, filed Oct. 14, 1992, entitled "Method for Selecting Nucleic Acids on the Basis of Structure," now abandoned (See, U.S. Pat. No. 5,707,796) herein specifically incorporated by reference, describes the selection of nucleic acid sequences on the basis of specific electrophoretic behavior. The SELEX technology may also be used in conjunction with other selection techniques, such as HPLC, column chromatography, chromatographic methods in general, solubility in a particular solvent, or partitioning between two phases.

BRIEF SUMMARY OF THE INVENTION

In one embodiment, the present invention includes a method for selecting and identifying nucleic acid ligands from a candidate mixture of randomized nucleic acid sequences on the basis of the ability of the randomized nucleic acid sequences to bind and/or photocrosslink to a target molecule. This embodiment is termed Covalent SELEX generally, and PhotoSELEX specifically when irradiation is required to form covalent linkage between the nucleic acid ligand and the target.

In one variation of this embodiment, the method comprises preparing a candidate mixture of nucleic acid sequences which contain photoreactive groups; contacting the candidate mixture with a target molecule wherein nucleic acid sequences having increased affinity to the target molecule bind the target molecule, forming nucleic acid-target molecule complexes; irradiating the nucleic acid-target molecule mixture, wherein some nucleic acids incorporated in nucleic acid-target molecule complexes crosslink to the target molecule via the photoreactive functional groups; taking advantage of the covalent bond to partition the crosslinked nucleic acid-target molecule complexes from free nucleic acids in the candidate mixture; and identifying the nucleic acid sequences that were photocrosslinked to the target molecule. The process can further include the iterative step of amplifying the nucleic acids that photocrosslinked to the target molecule to yield a mixture of nucleic acids enriched in sequences that are able to photocrosslink to the target molecule.

In another variation of this embodiment of the present invention, nucleic acid ligands to a target molecule selected through SELEX are further selected for their ability to crosslink to the target. Nucleic acid ligands to a target molecule not containing photoreactive groups are initially identified through the SELEX method. Photoreactive groups are then incorporated into these selected nucleic acid ligands, and the ligands contacted with the target molecule. The nucleic acid-target molecule complexes are irradiated and those able to photocrosslink to the target molecule identified.

In another variation of this embodiment of the present invention, photoreactive groups are incorporated into all possible positions in the nucleic acid sequences of the candidate mixture. For example, 5-iodouracil and 5-iodocytosine may be substituted at all uracil and cytosine positions. The first selection round is performed with irradiation of the nucleic acid-target molecule complexes such that selection occurs for those nucleic acid sequences able to photocrosslink to the target molecule. Then SELEX is performed with the nucleic acid sequences able to photocrosslink to the target molecule to select crosslinking sequences best able to bind the target molecule.

In another variation of this embodiment of the present invention, nucleic acid sequences containing photoreactive groups are selected through SELEX for a number of rounds in the absence of irradiation, resulting in a candidate mixture with a partially enhanced affinity for the target molecule. PhotoSELEX is then conducted with irradiation to select ligands able to photocrosslink to the target molecule.

In another variation of this embodiment of the present invention, SELEX is carried out to completion with nucleic acid sequences not containing photoreactive groups, and nucleic acid ligands to the target molecule selected. Based on the sequences of the selected ligands, a family of related nucleic acid sequences is generated which contain a single photoreactive group at each nucleotide position. PhotoSELEX is performed to select a nucleic acid ligand capable of photocrosslinking to the target molecule.

In a further variation of this embodiment of the present invention, a nucleic acid ligand capable of modifying the bioactivity of a target molecule through binding and/or crosslinking to a target molecule is selected through SELEX, photoSELEX, or a combination of these methods.

In a further variation of this embodiment of the present invention, a nucleic acid ligand to a unique target molecule associated with a specific disease process is identified. In yet another variation of this embodiment of the present invention, a nucleic acid ligand to a target molecule associated with a disease state is used to treat the disease in vivo.

The present invention further encompasses nucleic acid sequences containing photoreactive groups. The nucleic acid sequences may contain single or multiple photoreactive groups. Further, the photoreactive groups may be the same or different in a single nucleic acid sequence. The photoreactive groups incorporated into the nucleic acids of the invention include any chemical group capable of forming a crosslink with a target molecule upon irradiation. Although in some cases irradiation may not be necessary for crosslinking to occur.

The nucleic acids of the present invention include single- and double-stranded RNA and single- and double-stranded DNA. The nucleic acids of the present invention may contain modified groups such as 2'-amino (2'-NH$_2$) or 2'-fluoro (2'-F)-modified nucleotides. The nucleic acids of the present invention may further include backbone modifications.

The present invention further includes the method whereby candidate mixtures containing modified nucleic acids are prepared and utilized in the SELEX process, and nucleic acid ligands are identified that bind or crosslink to the target species. In one example of this embodiment, the candidate mixture is comprised of nucleic acids wherein all uracil residues are replaced by 5-halogenated uracil residues, and nucleic acid ligands are identified that form covalent attachments to the selected target.

An additional embodiment of the present invention, termed solution SELEX, presents several improved methods for partitioning between ligands having high and low affinity nucleic acid-target complexes is achieved in solution and without, or prior to, use of a partitioning matrix. Generally, a central theme of the method of solution SELEX is that the nucleic acid candidate mixture is treated in solution and results in preferential amplification during PCR of the highest affinity nucleic acid ligands or catalytic RNAs. The solution SELEX method achieves partitioning between high and low affinity nucleic acid-target complexes through a number of methods, including (1) Primer extension inhibition which results in differentiable cDNA products such that the highest affinity ligands may be selectively amplified during PCR. Primer extension inhibition is achieved with the use of nucleic acid polymerases, including DNA or RNA polymerases, reverse transcriptase, and Qβ-replicase. (2) Exonuclease hydrolysis inhibition which also results in only the highest affinity ligands amplifying during PCR. This is achieved with the use of any 3'→5' double-stranded exonuclease. (3) Linear to circle formation to generate differentiable cDNA molecules resulting in amplification of only the highest affinity ligands during PCR.

In one embodiment of the solution SELEX method, synthesis of cDNAs corresponding to low affinity oligonucleotides are preferentially blocked and thus rendered non-amplifiable by PCR. In another embodiment, low affinity oligonucleotides are preferentially removed by affinity column chromatography prior to PCR amplification. Alternatively, high affinity oligonucleotides may be preferentially removed by affinity column chromatography. In yet another embodiment of the SELEX method, cDNAs corresponding to high affinity oligonucleotides are preferentially rendered resistant to nuclease enzyme digestion. In a further embodiment, cDNAs corresponding to low affinity oligonucleotides are rendered preferentially enzymatically or chemically degradable.

Solution SELEX is an improvement over prior art partitioning schemes. With the method of the present invention, partitioning is achieved without inadvertently also selecting ligands that only have affinity for the partitioning matrix, the speed and accuracy of partitioning is increased, and the procedure may be readily automated.

The present disclosure provides non-limiting examples which are illustrative and exemplary of the invention. Other partitioning schemes and methods of selecting nucleic acid ligands through binding and photocrosslinking to a target molecule will be become apparent to one skilled in the art from the present disclosure.

BRIEF DESCRIPTION OF THE FIGURES

FIG. 1 shows structures of photoreactive chromophores which have been incorporated into nucleic acids.

FIG. 16 (SEQ ID NOS:5–55) shows the sequence of the previously identified RNA ligand to HIV-1 Rev protein that is referred to herein as 6a (SEQ ID NO:5). Also shown are 52 sequences from round 13 selected for photocrosslinking to HIV-1 Rev protein.

DETAILED DESCRIPTION OF THE INVENTION

Figure 2:
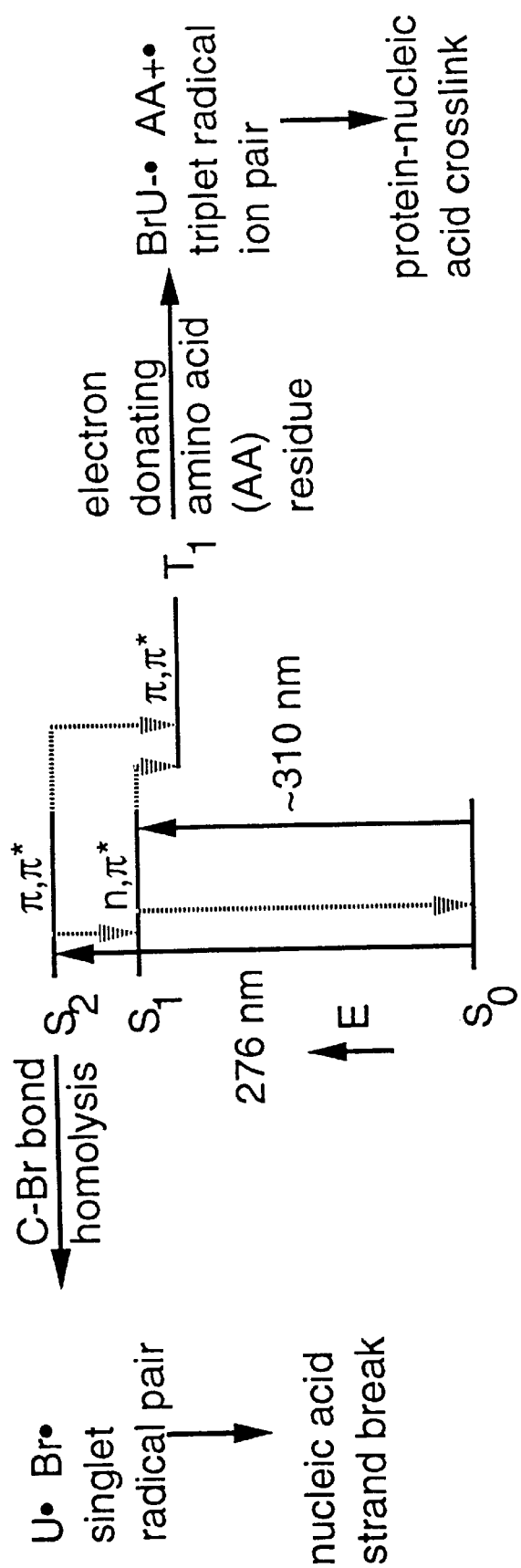
FIG. 2 shows a Jablonski energy level diagram for the 5-bromouracil chromophore and the reactivity of the various excited states.

The present invention includes a variation of the SELEX method for selecting nucleic acid ligands. This application hereby specifically incorporates by reference the full text including the definitions provided in the earlier SELEX patent applications, specifically those provided in U.S. patent application Ser. No. 07/536,428, filed Jun. 11, 1990, now abandoned, and 07/714,131, filed Jun. 10, 1991, now U.S. Pat. No. 5,475,096. The method of one embodiment of the present invention, termed covalent SELEX or photoSELEX, identifies and selects nucleic acid ligands capable of binding and/or photocrosslinking to target molecules.

This application also presents a method for improved partitioning of nucleic acid ligands identified through the SELEX method.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the potential of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–10%) is retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acid mixture to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

Partitioning means any process whereby ligands bound to target molecules can be separated from nucleic acids not bound to target molecules. More broadly stated, partitioning allows for the separation of all the nucleic acids in a candidate mixture into at least two pools based on their relative affinity to the target molecule. Partitioning can be accomplished by various methods known in the art. Nucleic acid-protein pairs can be bound to nitrocellulose filters while unbound nucleic acids are not. Columns which specifically retain nucleic acid-target complexes can be used for partitioning. For example, oligonucleotides able to associate with a target molecule bound on a column allow use of column chromatography for separating and isolating the highest affinity nucleic acid ligands. Liquid-liquid partitioning can be used as well as filtration gel retardation, and density gradient centrifugation.

I. PhotoSELEX.

The present invention encompasses nucleic acid ligands which bind, photocrosslink and/or photoinactivate target molecules. Binding as referred to herein generally refers to the formation of a covalent bond between the ligand and the target, although such binding is not necessarily irreversible. Certain nucleic acid ligands of the present invention contain photoreactive groups which are capable of photocrosslinking to the target molecule upon irradiation with light. Additional nucleic acid ligands of the present invention are capable of bond formation with the target in the absence of irradiation.

In one embodiment, the present invention encompasses nucleic acid ligands which are single- or double-stranded RNA or DNA oligonucleotides. The nucleic acid ligands of the present invention may contain photoreactive groups capable of crosslinking to the selected target molecule when irradiated with light. Further, the present invention encompasses nucleic acid ligands containing any modification thereof Reference to a photoreactive group herein may simply refer to a relatively simple modification to a natural nucleic acid residue that confers increased reactivity or photoreactivity to the nucleic acid residue. Such modifications include, but are not limited to, modifications at cytosine exocyclic amines, substitution with halogenated groups, e.g., 5'-bromo- or 5'-iodo-uracil, modification at the 2'-position, e.g., 2'-amino (2'-$NH_2$) and 2'-fluoro (2'-F), backbone modifications, methylations, unusual base-pairing combinations and the like. For example, the nucleic acid ligands of the present invention may include modified nucleotides such as 2'-NH$_2$-iodouracil, 2'-NH$_2$-iodocytosine, 2'-NH$_2$-iodoadenine, 2'-NH$_2$-bromouracil, 2'-NH$_2$-bromocytosine, and 2'-NH$_2$-bromoadenine.

In one embodiment of the photoSELEX method of the present invention, a randomized set of nucleic acid sequences containing photoreactive groups, termed the candidate mixture, is mixed with a quantity of the target molecule and allowed to establish an equilibrium binding with the target molecule. The nucleic acid-target molecule mixture is then irradiated with light until photocrosslinking is complete as indicated by polyacrylamide gel electrophoresis. Only some of those nucleic acids binding tightly to the target molecules will efficiently crosslink with the target.

The candidate mixture of the present invention is comprised of nucleic acid sequences with randomized regions including chemically reactive or a photoreactive group or groups. Preferably the reactive groups are modified nucleic acids. The nucleic acids of the candidate mixture preferably include a randomized sequence portion as well as conserved sequences necessary for efficient amplification. The variable sequence portion may contain fully or partially random sequence; it may also contain subportions of conserved sequence incorporated within the randomized sequence regions.

Preferably, each oligonucleotide member of the candidate mixture contains at least one chemically reactive or photoreactive group. Further, each oligonucleotide member of the candidate mixture may be partially or fully substituted at each position by modified nucleotides containing reactive groups. The candidate mixture may also be comprised of oligonucleotides containing more than one type of reactive group.

The target molecules bound and/or photocrosslinked by the nucleic acid ligands of the present invention are commonly proteins and are selected based upon their role in disease and/or toxicity. Examples are enzymes for which an inhibitor is desired or proteins for which detection is desired. However, the target molecule may be any compound of interest for which a ligand is desired. A target molecule can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation.

Figure 5:
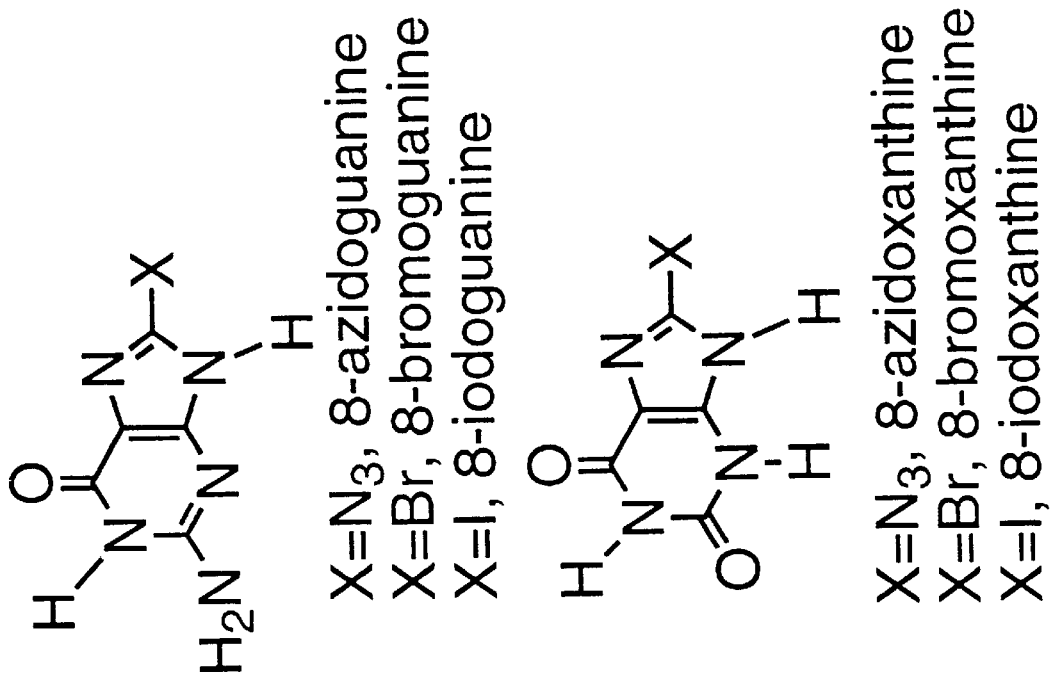
FIG. 5 shows structures of photoreactive chromophores which can be incorporated into randomized nucleic acid sequences.

A photoreactive group for the purpose of this application is preferably a modified nucleotide that contains a photochromophore, and that is capable of photocrosslinking with a target species. Although referred to herein as photoreactive groups, in some cases as described below, irradiation is not necessary for covalent binding to occur between the nucleic acid ligand and the target. Preferentially, the photoreactive group will absorb light in a spectrum of the wavelength that is not absorbed by the target or the non-modified portions of the oligonucleotide. This invention encompasses, but is not limited to, oligonucleotides containing a photoreactive group selected from the following: 5-bromouracil (Brq), 5-iodouracil (IU), 5-bromovinyluracil, 5-odovinyluracil, 5-azidouracil, 4-thiouracil, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-azidoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-bromodeoxyuridine, 8-bromo-2'-deoxyadenine, 5-iodo-2'-deoxyuracil, 5-iodo-2'-deoxycytosine, 5-[(4-azidophenacyl) thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine (FIG. 5). In one embodiment, the photoreactive groups are 5-bromouracil (BrU) and 5-iodouracil (IU).

The photoreactive groups of the present invention are capable of forming bonds with the target species upon irradiation of an associated nucleic acid target pair. The associated pair is referred to herein as a nucleoprotein complex, and in some cases irradiation is not required for bond formation to occur. The photocrosslink that typically occurs will be the formation of a covalent bond between the associated nucleic acid and the target. However, a tight ionic interaction between the nucleic acid and target may also occur upon irradiation.

In one embodiment, photocrosslinking occurs due to electromagnetic irradiation. Electromagnetic irradiation includes ultraviolet light, visible light, X-ray and gamma ray. 5-Halo substituted deoxyuracils and deoxycytosines are known to sensitize cells to ionizing radiation (Szybalski (1974) Cancer Chemother. Rep. 58:539).

Crosslinking experiments have shown that a precise juxtaposition of either IU or BrU and a tyrosine, tryptophan, or histidine is required for a high yield crosslinking to occur. The present invention takes advantage of this finding with selection for crosslinking molecules with randomly incorporated photoreactive groups. In one embodiment of the present invention, the photoreactive groups 5-bromouracil (BrU) or 5-iodouracil (IU) are incorporated into RNA by T7 polymerase transcription with the 5-halouridine triphosphate present in place of uridine triphosphate. Incorporation is achieved by using a mixture of 5-halouridine triphosphate and uridine triphosphate or all 5-halouridine triphosphate. A randomized set of $^{32}$P or $^{33}$P-labeled or unlabeled RNA sequences is obtained from a randomized set of DNA templates, synthesized using standard methodology.

The randomized set of RNA oligonucleotides containing BrU or IU are mixed with a quantity of a target protein. The photoreactive chromophore is incorporated randomly into RNA as BrU or IU in place of uracil using standard methodology. The RNA-target protein mixture is irradiated with near ultraviolet light in the range of 300 to 325 nm until photocrosslinking is complete. Only those photoreactive groups adjacent to a reactive amino acid residue in a nucleoprotein complex form a covalent bond to the protein. Excited BrU or IU, returns to the ground state unless it is near a reactive functional group such as an oxidizable amino acid residue. Amino acid residues which have been established as being reactive with the lowest triplet state of 5-bromouracil include tyrosine, tryptophan, histidine, and cystine (see FIG. 3). Others of potential reactivity based upon mechanistic studies are phenylalanine, methionine, cysteine, lysine, and arginine.

Nucleoprotein complexes which do not form crosslinks may be easily disrupted by adjusting the reaction medium such as by denaturing with heat and/or salt. Nucleic acids covalently bound to the protein may be separated from free nucleic acids on a nitrocellulose filter or by other partitioning methods known to those skilled in the art. Alternate methods for separating nucleic acids covalently bound to targets from free nucleic acids include gel electrophoresis followed by electroelution, precipitation, differential solubility, and chromatography. To one skilled in the art, the method of choice will depend at least in part on the target molecule of interest. The crosslinked nucleic acids are released from the nitrocellulose filter by digestion of the protein material with enzymes such as Proteinase K. At this point 5-halouracil groups which have photocrosslinked to the target protein are bound to a single amino acid or to a short peptide. The read-through ability of reverse transcriptase is not effected by incorporation of a substituent at the 5-position of uracil because reverse transcriptase (RT) does not differentiate the 5-position of uracil from that of thymine. Derivatization of the 5-position has been used to incorporate groups as large as biotin into RNA molecules. In one embodiment of the present invention, the target is removed from the selected photocrosslinked nucleic acid by photo or chemical dissociation.

Complementary nucleic acid copies of the selected RNA sequences are prepared with an appropriate primer. The cDNA is amplified with a DNA polymerase and a second primer. 5-Halo-2'-deoxyuracil is not employed in the DNA synthesis and amplification steps. The amplified DNAs are then transcribed into RNA sequences using 5-halouridine triphosphate in place of uridine triphosphate in the same or different ratio of 5-halouridine to uridine in the candidate mixture.

For the subsequent round of photoSELEX, the partially selected RNA sequences are again allowed to complex with a quantity of the target protein. Subsequently, the nucleoprotein complexes are irradiated in the region of 300–325 nm. RNA sequences which have crosslinked to protein are again separated from RNA sequences which have not crosslinked. cDNAs are prepared and amplified and a third set of RNA sequences containing 5-halouracil are prepared. The cycle is continued until it converges to one or several RNA ligands which bind with high affinity and photocrosslink to the target protein. Shortening of the irradiation time in later cycles can further enhance the selection. The cDNAs of the selected RNA ligands are amplified, gel purified, and sequenced. Alternatively, the RNA sequences can be sequenced directly. The selected RNA sequences are then transcribed from the appropriate synthesized DNA template, again using 5-halouridine triphosphate in place of uridine triphosphate (Example 11).

In another embodiment of the present invention, photoSELEX is performed on oligonucleotide sequences preselected for their ability to bind the target molecule (Example 12). SELEX is initially performed with oligonucleotides which do not contain photoreactive groups. The RNA ligand is transformed into a photoreactive ligand by substitution of photoreactive nucleic acid nucleotides at specific sites in the ligand. The photochemically active permutations of the initial ligand may be developed through a number of approaches, such as specific substitution or partial random incorporation of the photoreactive nucleotides. Specific substitution involves the synthesis of a variety of oligonucleotides with the position of the photoreactive nucleotide changed manually. The location of the substitution is directed based upon the available data on binding of the ligand to the target molecule. For example, substitutions are made to the initial ligand in areas of the molecule that are known to interact with the target molecule. For subsequent selection rounds, the photoSELEX method is used to select for the ability to crosslink to the target molecule upon irradiation.

In another embodiment of the present invention, nucleic acid ligands are selected by photoSELEX followed by SELEX. PhotoSELEX is performed initially with oligonucleotide sequences containing photoreactive groups. Sequences selected for their ability to crosslink to the target molecule are then selected for ability to bind the target molecule through the SELEX method (Example 13).

In another embodiment of the present invention, a limited selection of oligonucleotides through SELEX is followed by selection through photoSELEX (Example 14). The initial SELEX selection rounds are conducted with oligonucleotides containing photoreactive groups. After a number of SELEX rounds, photoSELEX is conducted to select oligonucleotides capable of binding the target molecule.

In yet another embodiment of the present invention, nucleic acid ligands identified through SELEX are subjected to limited randomization, followed by selection through photoSELEX (Example 15). SELEX is first carried out to completion with nucleic acid sequences not containing photoreactive groups. The sequence of the nucleic acid ligand is used to generate a family of oligonucleotides through limited randomization. PhotoSELEX is subsequently performed to select a nucleic acid ligand capable of photocrosslinking to the target molecule.

In another embodiment of the present invention, photoSELEX is used to identify a nucleic acid ligand capable of modifying the biological activity of a target molecule (Example 16).

In a further embodiment of the present invention, the photoSELEX methodology is applied diagnostically to identify unique proteins associated with specific disease states (Example 17). In yet another embodiment of the present invention, nucleic acid ligands capable of crosslinking a target molecule associated with a specific disease condition are used in vivo to crosslink to the target molecule as a method of treating the disease condition (Examples 18 and 19).

Figure 3:
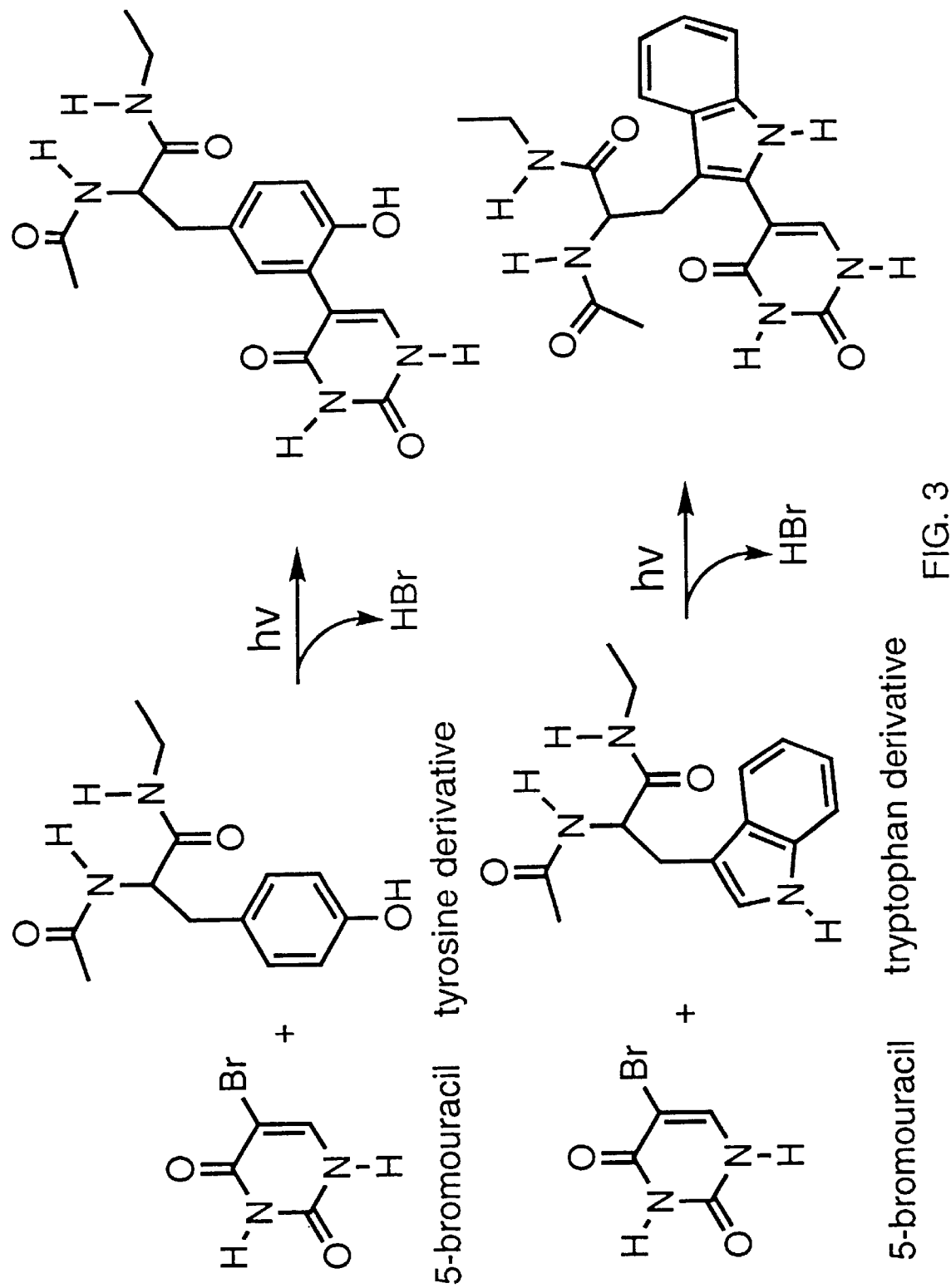
FIG. 3 shows the model reactions for photocrosslinking of the 5-bromouracil chromophore to amino acid residues such as tyrosine, tryptophan, histidine, and cystine.
Figure 3:
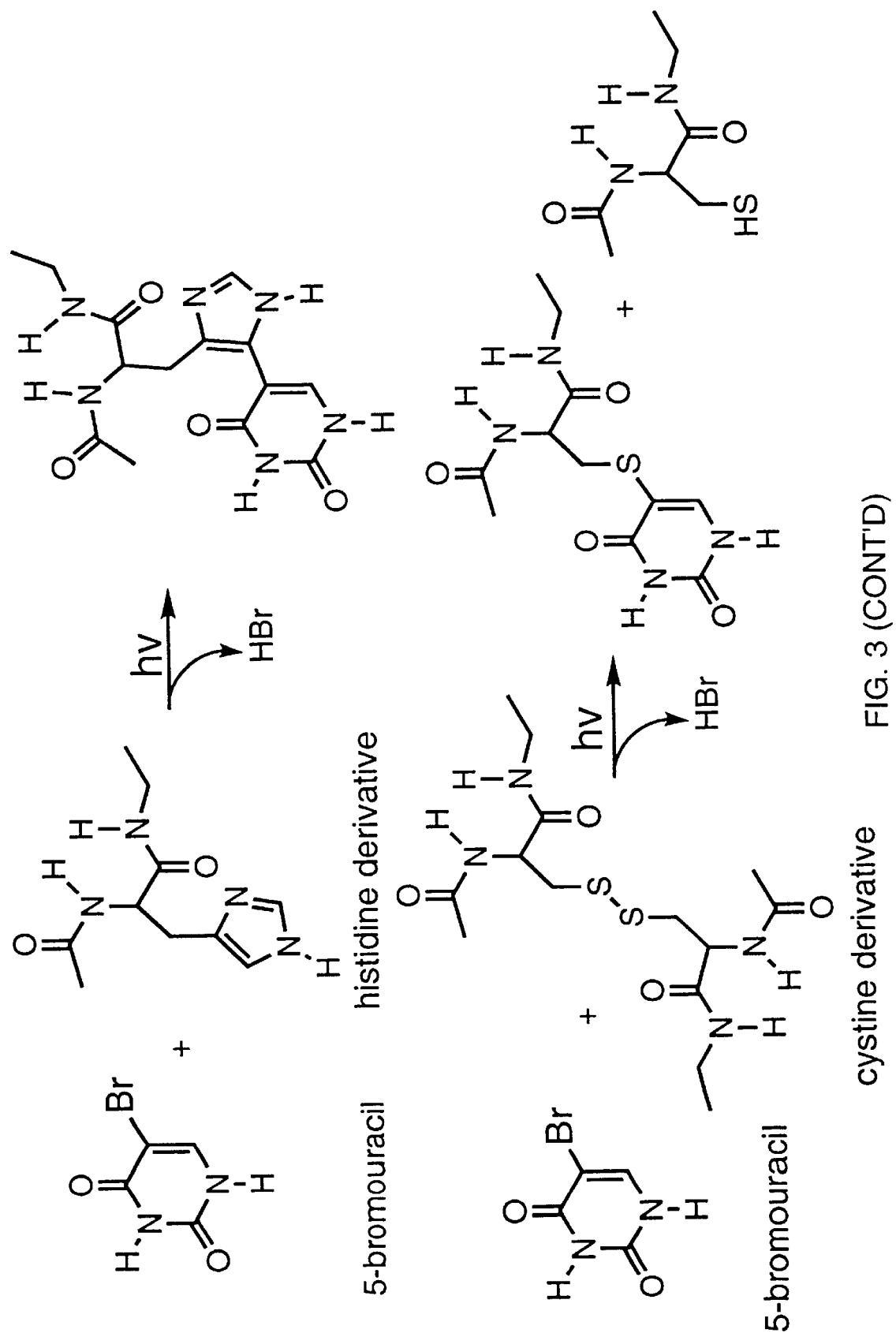

In one embodiment of the present invention, RNA ligands identified by photoSELEX are used to detect the presence of the target protein by binding to the protein and then photocrosslinking to the protein. Detection may be achieved by incorporating $^{32}$P or $^{33}$P-labels and detecting material which is retained by a nitrocellulose filter by scintillation counting or detecting material which migrates correctly on an electrophoretic gel with photographic film. Alternatively, photoSELEX creates a fluorescent chromophore which is detected by fluorescence emission spectroscopy. Fluorescence emission for the products of reaction of 5-bromouracil to model peptides (as shown in FIG. 3) has been reported by Dietz and Koch (1987) supra. In another embodiment of the invention, a fluorescent label is covalently bound to the RNA and detected by fluorescence emission spectroscopy. In another embodiment of the invention, RNA ligands selected through photoSELEX are used to inhibit the target protein through the same process. In yet another embodiment, the photoselected ligand is bound to a support and used to covalently trap a target.

Figure 4:
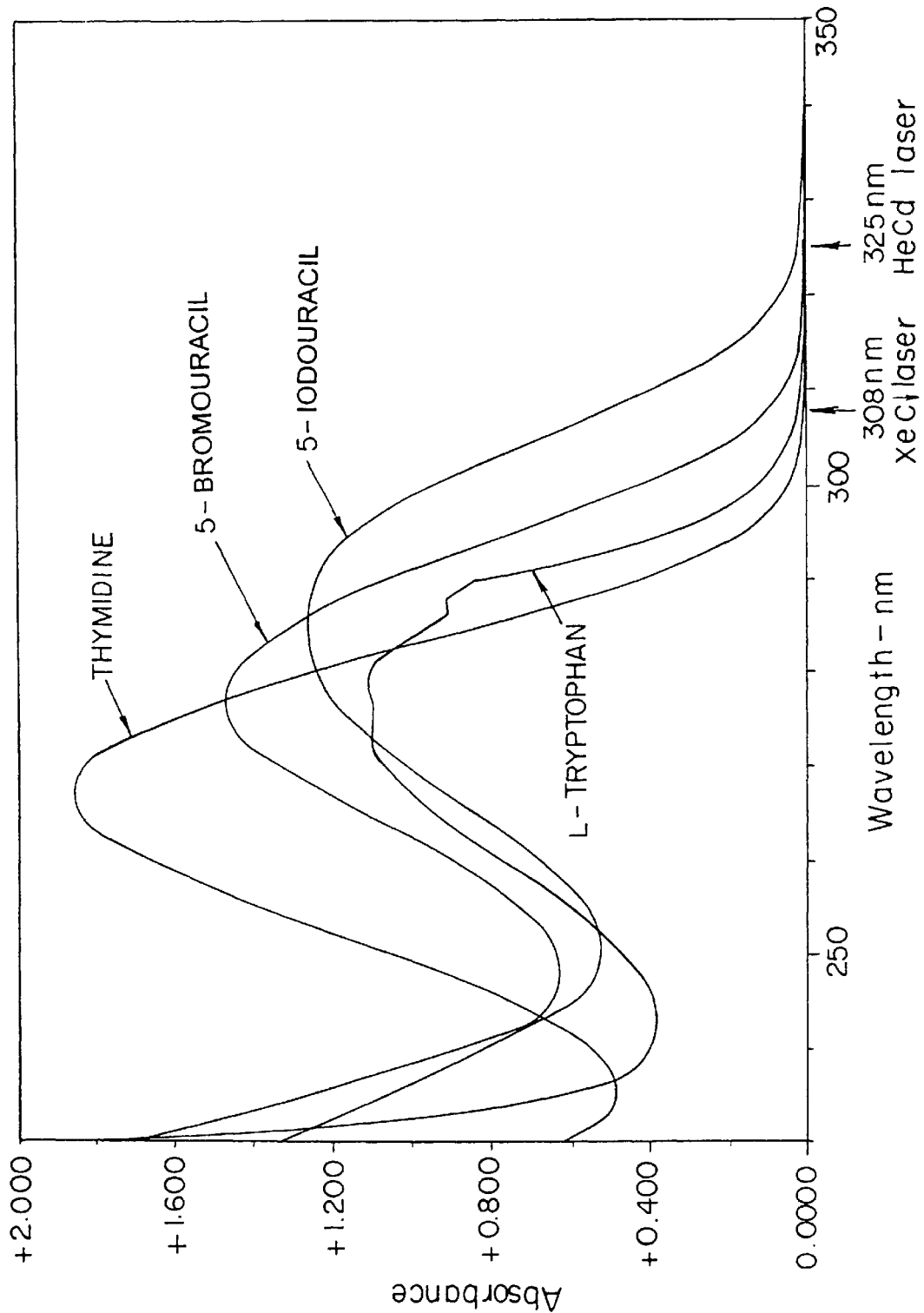
FIG. 4 compares UV absorption by thymidine, 5-bromouracil, 5-iodouracil, and L-tryptophan in TMK pH 8.5 buffer (100 mM tris(hydroxymethyl)aminomethane hydrochloride, 10 mM magnesium acetate, and 80 mM potassium chloride). The emission wavelengths of the XeCl and HeCd lasers are also indicated. Of particular importance is absorption by 5-iodouracil at 325 nm without absorption by tryptophan or thymidine. The molar extinction coefficient for 5-iodouracil at 325 nm is 163 L/mol cm.

In a one embodiment of the invention, 5-iodouracil is incorporated into the RNA sequences of the candidate mixture, and light in the range of 320–325 nm is used for irradiation. This combination assures regionselective photocrosslinking of the 5-halouracil chromophore to the target protein without other non-specific photoreactions. In particular, tryptophan residues of proteins and thymine and uracil bases of nucleic acids are known to be photoreactive. As shown in FIG. 4, 5-iodouracil absorbs at 325 nm but tryptophan and the standard nucleic acid bases do not. The molar extinction coefficient for 5-iodouracil at 325 nm is 163 L/mol cm. Monochromatic light in the region of 320–325 nm is preferably supplied by a frequency doubled tunable dye laser emitting at 320 run or by a helium cadmium laser emitting at 325 nm.

In one embodiment of the invention a xenon chloride (XeCl) excimer laser emitting at 308 nm is employed for the photocrosslinking of 5-iodouracil-bearing RNA sequences to a target protein. With this laser, a high yield of photocrosslinking of nucleoprotein complexes is achieved within a few minutes of irradiation time.

In another embodiment of the invention, photocrosslinking of 5-iodouracil-bearing RNA sequences to a target protein is achieved with wavelength filtered 313 nm high pressure mercury lamp emission or with low pressure mercury lamp emission at 254 nm absorbed by a phosphor and re-emitted in the region of 300–325 nm. The latter emission is also carefully wavelength filtered to remove 254 nm light not absorbed by the phosphor and light in the region of 290–305 nm which could damage the protein.

In a further embodiment of the invention, photocrosslinking of BrU- or IU-bearing RNA sequences to a target protein is achieved with light in the region of 350–400 nm which populates directly the triplet state from the ground state. Monochromatic light from the third harmonic of a Neodymium YAG laser at 355 nm or the first harmonic from a xenon fluoride (XeF) excimer laser at 351 mn may be particularly useful in this regard.

In yet another embodiment of the invention the photoreactive nucleotides are incorporated into single stranded DNAs and amplified directly with or without the photoreactive nucleotide triphosphate.

A. Covalent SELEX and Nucleic Acid Ligands That Bind to HIV-1 Rev Protein With and Without Irradiation.

The target protein chosen to illustrate photo-SELEX is Rev from HIV-1. Rev's activity in vivo is derived from its association with the Rev-responsive element (RRE), a highly structured region in the HIV-1 viral RNA. Previous RNA SELEX experiments of Rev have allowed the isolation of very high affinity RNA ligands. The highest affinity ligand, known as "6a," (SEQ ID NO:5) has a $K_d$ of approximately 1 nM and is shown in FIG. 16. The secondary structure of 6a, and its interaction with Rev, have been well characterized.

The construction of the nucleic acid library for photo-SELEX was based upon the Rev 6a sequence (SEQ ID NO:5). During the synthesis of the deoxyoligonucleotide templates for SELEX, the random region of the template was substituted by a "biased randomization" region, in which the ratio of the four input bases was biased in favor of the corresponding base in the 6a sequence. (Actual ratios were 62.5:12.5:12.5:12.5.) For example, if the 6a base for a particular position is G, then the base input mixture for this synthesis step is 62.5% G, and 12.5% of the other three bases.

The photoreactive uracil analogue 5-iodouracil (iU), which has been used to generate high-yield, region-specific crosslinks between singly-substituted iU nucleic acids and protein targets (Willis et al. (1993) Science 262:1255) was used for this example. The iU chromophore is reactive under long-wavelength ultraviolet radiation, and may photocouple to the aromatic amino acids of protein targets by the same mechanism as 5-bromouracil (Dietz et al. (1987) J. Am. Chem. Soc. 109:1793). As discussed above, the target for this study is the HIV-1 Rev protein, which is necessary for productive infection of the virus (Feinberg et al. (1986) Cell 46:807) and the expression of the viral structural genes gag, pol and env (Emerman et al. (1989) Cell 57:1155). The interaction of Rev with high affinity RNA ligands is well characterized. A single, high-affinity site within the RRE (the IIB stem) has been identified (Heaphy et al. (1991) Proc. Natl. Acad. Sci. USA 88:73.66). In vitro genetic selection experiments have generated RNA ligands that bind with high affinity to Rev and have helped determine the RNA structural elements necessary for Rev:RNA interactions (Bartel et al. (1991) Cell 67:529; Tuerk et al., In the Polymerase Chain Reaction (1993); Jensen et al. (1994) J. Mol. Biol. 235:237).

A "biased randomization" DNA oligonucleotide library, based upon the high affmity Rev ligand sequence 6a (SEQ ID NO:5), contains approximately $10^{14}$ unique sequences. This template was used for in vitro T7 transcription with 5-iUTP to generate fully-substituted iU RNA for selection. The photo-SELEX procedure alternated between affinity selection for Rev using nitrocellulose partitioning and monochromatic UV irradiation of the nucleoprotein complexes with denaturing polyacrylamide gel partitioning of the crosslinked complexes away from non-crosslinked RNA sequences. The final procedure utilized a simultaneous selection for affinity and crosslinking using competitor tRNA. Each round constitutes a selection followed by the conversion of recovered RNA to cDNA, polymerase chain reaction (PCR) amplification of the DNA, and in vitro transcription to generate a new pool of iU-RNA. To amplify RNA's recovered as covalent nucleoprotein complexes, the appropriate gel slice was isolated and proteinase K treated.

The RNA pool was first subjected to three rounds of affinity selection with Rev protein, with partitioning of the higher affinity sequences by nitrocellulose filters. Next, the evolving RNA pool was subjected to UV laser irradiation in the presence of excess Rev protein to allow those RNA sequences with the ability to crosslink with the protein to do so. Crosslinked RNA sequences were then partitioned using polyacrylamide gel electrophoresis (PAGE). These crosslinked RNAs were recovered from the gel material, the linked Rev protein digested away, and the RNAs used for cDNA synthesis and further amplification for the next round of photoSELEX. A 308 nm XeCl excimer laser was used for the first round of photocrosslinking; thereafter, a 325 nm HeCd laser was employed.

Following four rounds of selection for laser-induced crosslinking, the RNA pool was again put through three rounds of affinity selection. Finally, the RNA pool was selected simultaneously for its ability to bind Rev with high affinity and to crosslink to the protein. This was accomplished by using high concentrations of a non-specific nucleic acid competitor in the photocrosslinking reaction.

Figure 15:
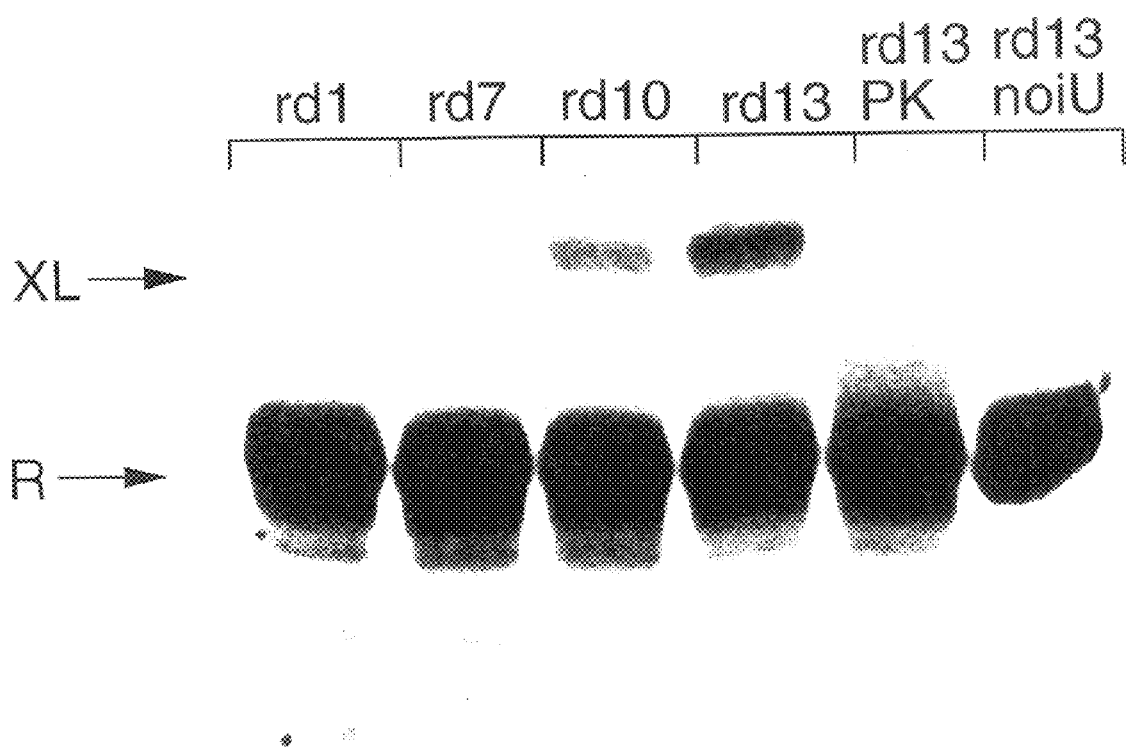
FIG. 15 shows the photocrosslinking of [$\alpha$-$^{32}$P] GTP labelled pool RNA to HIV-1 Rev protein using tRNA competition.

Crosslinked product increased approximately 30-fold from the starting pool to round 13 (FIG. 15). Under these conditions, the greatest increase in crosslinking is correlated with the greatest increase in affinity—from round 7 to round 10.

Figure 17:
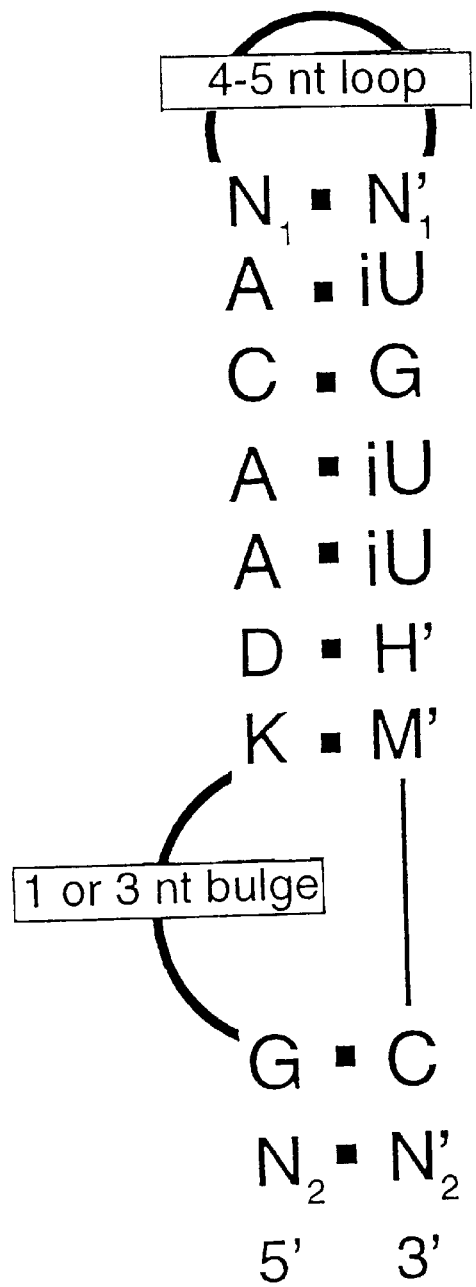
FIG. 17 (SEQ ID NOS:56–57) shows the consensus for class 1 ligands and class 2 ligands. Class 1: Consensus secondary structure for class 1 and class 2 molecules. $N_1$-$N_1'$ indicate 1–2 complementary base pairs; $N_2$-$N_2'$ indicates 1–4 complementary base pairs, D-H' is an A-U, U-A, or G-C base pair; K-M' is a G-C or U-A base pair (16). Class 2: Bold sequences represent the highly conserved 10 nucleotides that characterize class 2 molecules; base-pairing is with the 5' fixed end of the molecule.
Figure 17:
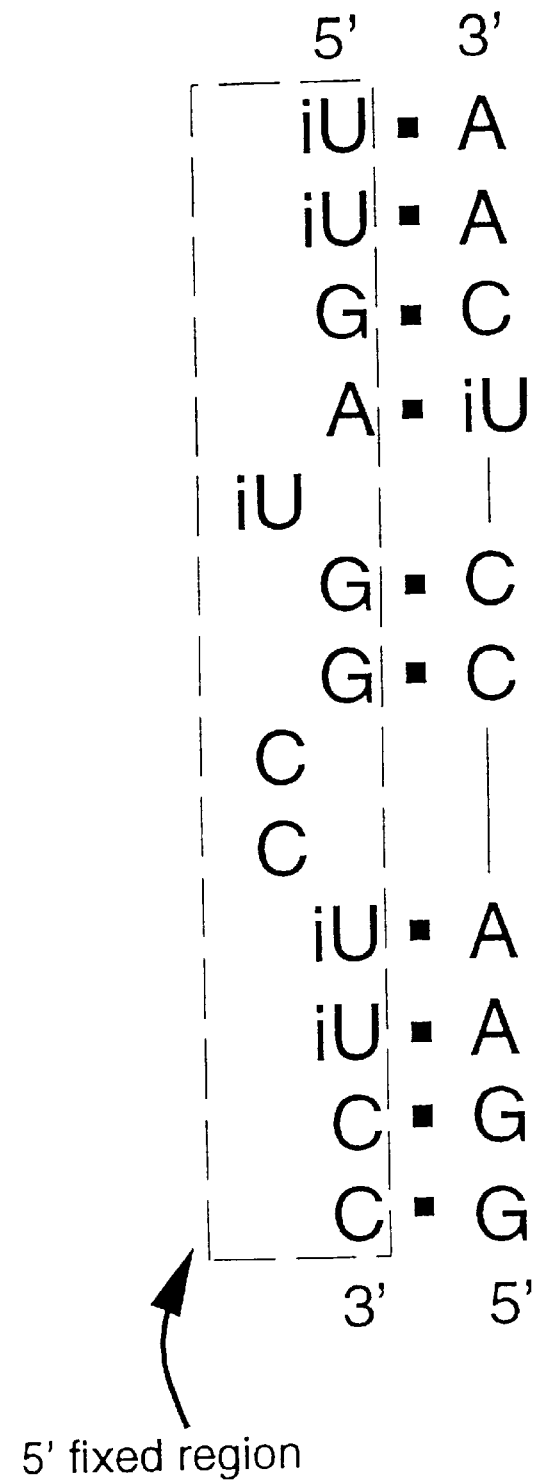

After 13 rounds of selection, the PCR products were cloned and 52 isolates sequenced (FIG. 16, SEQ ID NOS:5–55). Class 1 molecules, which comprise 77% of the total sequences, contain a very highly conserved motif, 5'KDAACAN . . . N'UGUUH'M'3' (SEQ ID NO:56) (FIG. 17). Computer folding algorithms predict that this conserved motif is base-paired and lies in a stem-loop structure. Subclasses a–d (FIG. 16, SEQ ID NOS:5–43) illustrate different strategies utilized in the "biased randomization" pool to obtain the consensus motif Class 2 molecules show a highly conserved 10-base sequence (FIG. 17, SEQ ID NO. 57), which is predicted to fold with the 5' fixed region of the RNA and forms a structure distinct from either the class 1 or the 6a (SEQ ID NO:5) motif. All class 1 sequences exhibit biphasic binding to Rev, with high affinity dissociation constants ($K_d$s) ranging from 1–10 nM. Class 2 sequences show monophasic binding to Rev with $K_d$s approximately of 30–50 nM. Analysis of round 13 sequences reveal that the frequency of the consensus motifs for class 1 and class 2 populations was very small in the starting pool, and some individual sequences arose only through the mutational pressures of the photo-SELEX procedure.

Cross-linking behavior differs between the two classes. Under high Rev concentrations (500 nM), and 4 min. of 325 nm irradiation, class 2 molecules produce greater crosslink yield and efficiency than class 1 molecules (data not shown); presumably, this behavior allows the class 2 molecules, with relatively low affinity for Rev, to compete under the photo-SELEX procedures. For class 1 molecules, longer irradiation times will produce higher molecular weight crosslinked species. Although not bound by theory, it is proposed that the RNAs, which contain both an evolved binding domain for Rev, and the fixed regions needed for amplification in SELEX, are able to bind more than one Rev molecule per RNA. Since each RNA contains on average 21 iU bases (RNA length—86 bases), it is thought that there is a certain promiscuity of the photoreaction that allows crosslinking of a single RNA to more than one Rev molecule at high protein concentrations. Class 2 molecules produce fewer high molecular weight species upon photocrosslinking; they are, on average, iU poor and may contain structures which do not allow binding/crosslinking to additional Rev molecules.

Analysis of individual round 13 RNAs revealed that a subpopulation could crosslink to Rev without laser irradiation. Thus, the single set of experiments demonstrated that both covalent SELEX without irradiation and photoSELEX with irradiation can be found in the same system. 4 of 15 round 13 sequences analyzed crosslink without laser irradiation (FIG. 16). From these few sequences, it was not readily possible to identify a sequence motif that confers laser independent crosslinking, although all molecules considered to date belong to the Ia subclass.

To further investigate laser-dependent and laser-independent crosslinking (LD-XL and LI-XL, respectively) and avoid the secondary photoproducts formed with full-length class 1 molecules, several small RNAs containing only the evolved sequences were constructed. Trunc2 and trunc24 (FIGS. 18 and 19) (SEQ ID NOS:58 AND 59) are based upon clones #3 and #24, respectively, and show monophasic binding to Rev with Kds of 0.5 nM (trunc2) and 20 nM (trunc24). Trunc2 (FIG. 18) exhibits LD-XL behavior, and trunc24 (FIG. 19) is capable of both LI-XL and LD-XL.

To explore the conformation and chemical requirements for LD-XL and LI-XL, crosslinking reactions were performed with trunc2 (SEQ ID NO:58) and trunc24 (SEQ ID NO:59) and several Arginine Rich Motif (ARM) proteins. The class of RNA-binding proteins includes the target protein, HIV-1 Rev, and also HIV-1 Tat and the highly similar HIV-2 Rev. LD-XL reactions with trunc2 (FIG. 18, SEQ ID NO:58) show that trunc2 is capable of crosslinking specifically to both HIV-1 and HIV-2 Rev proteins, but not HIV-1 Tat. The two slightly different migrating nucleoprotein complexes probably represent the ability of trunc2 to use one of two iU nucleotides to crosslink the Rev proteins. Although not bound by theory, it is proposed that a tryptophan residue present in the highly similar ARMs of both Rev proteins is the amino acid necessary for the specific photo-crosslinking of our high-affinity RNA ligands.

Trunc24 LI-XL (FIG. 19, SEQ ID NO:59), performed with the same proteins, shows crosslinking only to HIV-1 Rev. Like trunc3, trunc24 can photo-crosslink to HIV-2 Rev (data not shown). It was also observed that this LI-crosslink is reversible under highly denaturing conditions, or with high concentration of nucleic acid competitors. Although not bound by theory, these observations lead to the postulation that LI-XL proceeds by a Michael adduct between the 6 position of an IU and a cysteine residue, or possibly a 5 position substitution reaction. This postulation is consistent both with the observation that iU undergoes Michael adduct formation more readily than U, and the fact that HIV-1 Rev contains three cysteines, while HIV-2 Rev contains none.

Figure 20:
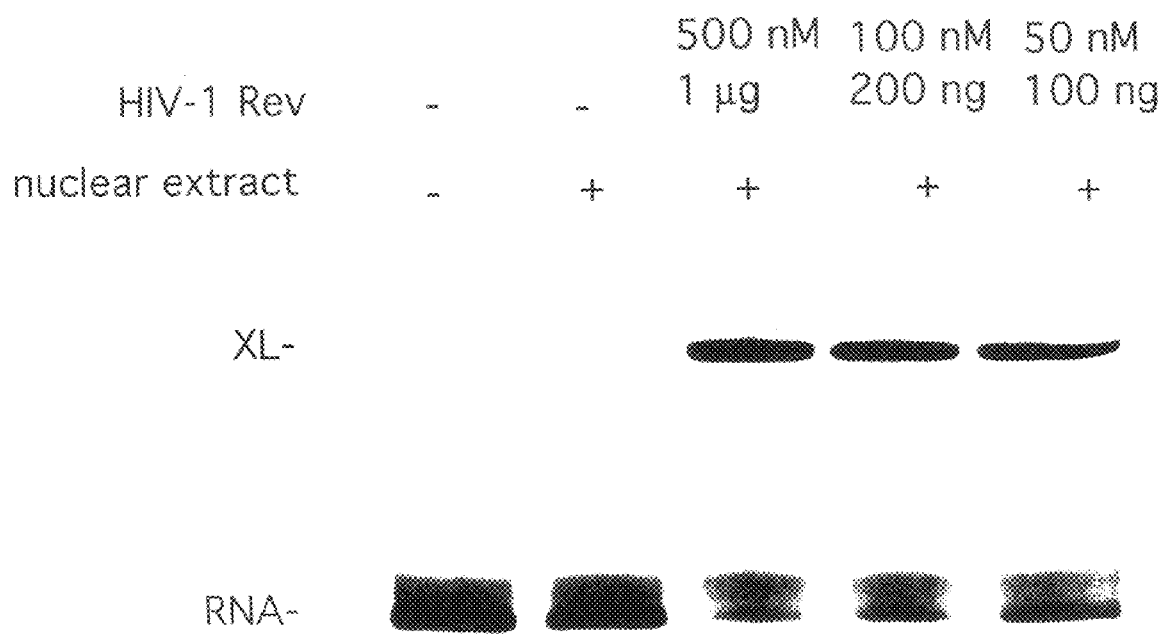
FIG. 20 shows the trunc24 (SEQ ID NO:59) photoindependent crosslinking with HIV-1 Rev in the presence of human nuclear extracts.

To test for the ability of trunc24 (SEQ ID NO:59) to discriminate HIV-1 Rev in a complex mixture, trunc24 and 10 μg of human fibroblast nuclear extract were mixed together with decreasing amounts of HIV-1 Rev (FIG. 20). At 50 nM Rev and a 1:100 weight ratio of Rev to nuclear extract, it was possible to see a very significant crosslinked product between trunc24 and Rev. Nuclear extracts and trunc24 alone resulted in no crosslinked products.

Example 1 describes the synthesis of hairpin RNA oligonucleotides RNA-1 (SEQ ID NO:1), RNA-2 (SEQ ID NO:2), and RNA-3 (SEQ ID NO:3) using 5-bromouridine triphosphate, 5-iodouridine triphosphate and uridine triphosphate, respectively. Experiments determining the RNA-protein binding curves for RNA-1 (SEQ ID NO:1), RNA-2 (SEQ ID NO:2), and RNA-3 (SEQ ID NO:3) to the bacteriophage R17 coat protein are described in Example 2. Example 3 describes the photocrosslinking of the RNA oligonucleotides to the R17 coat protein. The amino acid residue of the R17 coat protein photocrosslinked by RNA-1 (SEQ ID NO:1) after illumination via xenon chloride (XeCl) excimer laser at 308 nm is described in Example 4. Example 5 describes the photocrosslinking of iodouracil-substituted RNA-2 (SEQ ID NO:2) to the R17 coat protein by monochromatic emission at 325 nm. Example 6 describes the photocrosslinking of RNA-1 (SEQ ID NO:1) and RNA-2 (SEQ ID NO:2) to the R17 coat protein achieved after broad-band emission illumination with a transilluminator. Example 7 describes the photoreaction of 5-iodouracil with N-acetyltyrosine N-ethyl amide, which appeared to yield a photocrosslink similar to that achieved with 5-bromouracil-substituted nucleic acids to associated proteins. The preparation of a cDNA from a RNA photocrosslinked to the R17 coat protein is described in Example 8. Example 9 describes the photocrosslinking of an IC-substituted RNA ligand to the R17 coat protein.

Example 10 describes the incorporation of halogenated nucleotides into DNA. Examples 11–15 describes photoSELEX protocols which may be used to produce specific photoreactive nucleic acid ligands. Example 11 describes a continuous photoSELEX method. Example 12 describes a method in which nucleic acid ligands initially selected through SELEX are subsequently selected through photoSELEX for the capacity to crosslink to the target molecule. Example 13 describes one embodiment in which nucleic acid ligands identified through photoSELEX are then subjected to selection through SELEX and selected for ability to bind the target molecule. Example 14 describes another embodiment wherein a limited SELEX selection is followed by selection through photoSELEX. Example 15 describes an embodiment of the present invention in which nucleic acid ligands identified through SELEX are subjected to limited randomization, followed by selection through photoSELEX. Example 16 describes a method for selecting a nucleic acid ligand capable of modifying the biological activity of a target molecule. Example 17 describes a diagnostic procedure which uses the SELEX and photoSELEX methods to identify proteins associated with specific disease processes.

Example 18 describes a method for the in vivo treatment of disease through photoSELEX. A photoSELEX selected nucleic acid ligand able to bind and crosslink to a target molecule associated with a disease state is introduced into a patient in a number of ways known to the art. For example, the photoSELEX ligand may be transiently or constitutively expressed in the appropriate cells of a patient with the disease. Alternatively, the photoSELEX ligand may be taken into a patient's cells as a double-stranded DNA which is transcribed in the cell in the presence of iodinated cytosine. Iodinated cytosine may be administered to the patient, followed by irradiation with X-rays. IC incorporated into the nucleic acid ligand synthesized in the appropriate cells allows the ligand to crosslink and inactivate the target molecule. Further methods of introducing the photoSELEX ligand into a patient include liposome delivery of the halogenated ligand into the patient's cells.

Example 20 describes the production of modified nucleic acid ligands that crosslink, with or without irradiation, to HIV-1 Rev protein. FIG. 15 shows the results of crosslinking to the bulk candidate mixture at various rounds of SELEX. rd1-round 1 pool RNA; rd7-round 7 pool RNA; rd10-round 10 pool RNA; rd13-round 13 pool RNA; rd13/PK, photo-crosslinked round 13 pool RNA proteinase K treated (35 μl of a 100 μl reaction was incubated in 0.5% SDS, 50 μg/ml Proteinase K and 1 mM EDTA at 65 C. for one hour); rd13/no iU-round 13 pool RNA transcribed with UTP (no iU). R-free RNA; XL-crosslinked nucleoprotein complex.

Figure 18B:
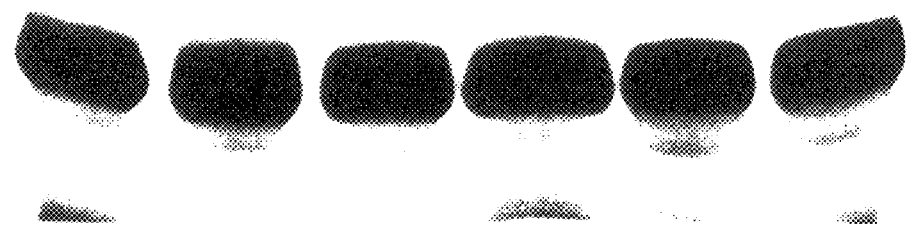
FIG. 18 (SEQ ID NO:58) shows the sequence and predicted secondary structure of trunc2 (18A). Also shown (18B) is a gel demonstrating the specificity of trunc2 photocrosslinking to ARM proteins.
Figure 19B:
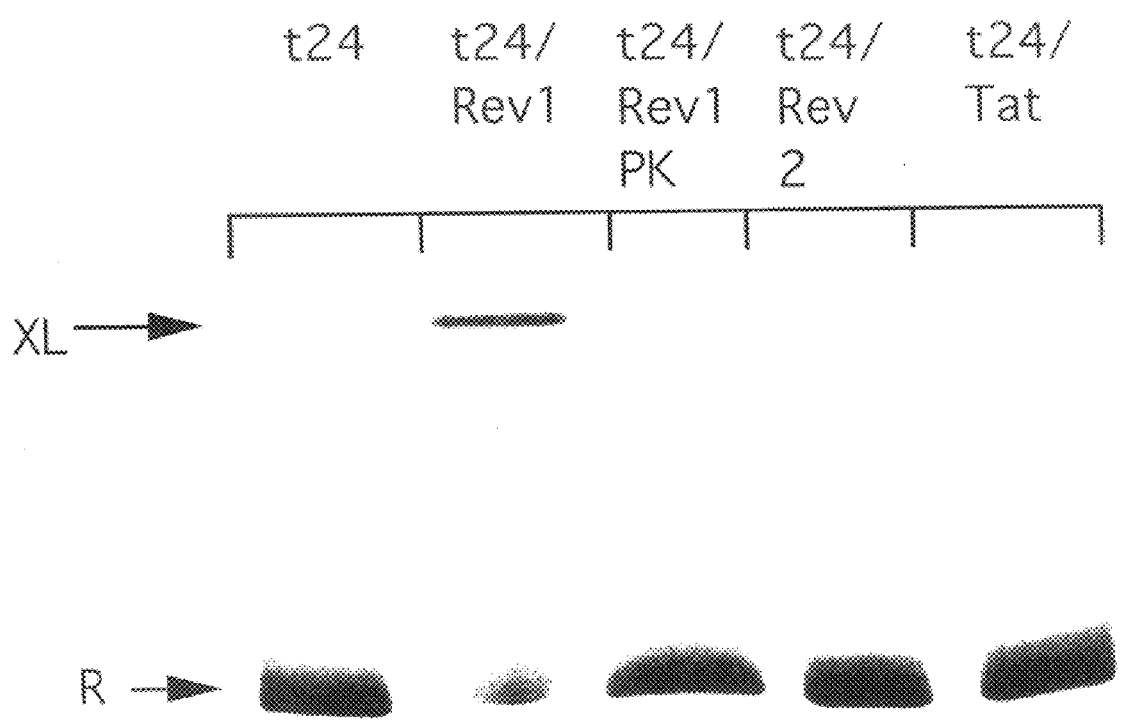
FIG. 19 shows the sequence and predicted secondary structure of trunc24 (SEQ ID NO:59) (19A). Also shown (19B) is a gel demonstrating the specificity of laser independent crosslinking to ARM proteins.

FIG. 16 shows the sequences sequenced after 13 rounds of SELEX (SEQ ID NOS:5–55). The sequences are aligned for maximum homology to the 6a sequence (SEQ ID NO:5). Underlines represent potential base pairing as indicated by computer RNA folding algorithms. Dashed underlines represent the 6a ligand "bubble" motif. Sequences flanked by underline represent either loop or bulge regions. Dashes are placed to maximize alignment with 6a. * denotes that two isolates were obtained. +indicates laser independent crosslinking and –denotes the lack of laser independent crosslinking to HIV-1 Rev. FIG. 17 (SEQ ID NOS:56–57) shows the consensus for class 1 and class 2 ligands. FIGS. 18 and 19 show the sequence of Trunc2 (SEQ ID NO:58) and Trunc24 (SEQ ID NO:59) and the specificity results. 500 nM protein, 20 μg tRNA, and approximately 1 nM of kinased trunc2 RNA were incubated for 10 min. at 37° C. and irradiated for 4 min. at 325 nm. t2-trunc2 RNA irradiated without added protein; t2Rev1/0'-trunc2 RNA, HIV-1 Rev protein and 0 min. of irradiation; t2/Rev1/4'-trunc2 RNA, HIV-1 Rev protein, and 4 min. of irradiation; t2/Rev1/4'/PK-trunc2 RNA, HIV-1 Rev protein, 4 min. of irradiation, and proteinase K treated as in FIG. 1; t2/Rev2/4'-trunc2 RNA, HIV-2 Rev protein, and 4 min. of irradiation; t2/Tat/4'-trunc2 RNA, HIV-1 Tat protein, and 4 min. of irradiation. R-free RNA; XL-crosslinked nucleoprotein complex. FIG. 20 shows the trunc24 photoindependent crosslinking with HIV-1 Rev in the presence of human nuclear extract.

II. Solution SELEX.

This embodiment of the present invention presents several improved methods for partitioning between oligonucleotides having high and low affinity for a target molecule. The method of the present invention has several advantages over prior art methods of partitioning: (1) it allows the isolation of nucleic acid ligands to the target without also isolating nucleic acid ligands to the partitioning matrix; (2) it increases the speed and accuracy by which the oligonucleotide candidate mixture is screened; and (3) the solution SELEX procedure can be accomplished in a single test tube, thereby allowing the partitioning step to be automated.

The materials and techniques required by the method of the present invention are commonly used in molecular biology laboratories. They include the polymerase chain reaction (PCR), RNA or DNA transcription, second strand DNA synthesis, and nuclease digestion. In practice, the techniques are related to one another in a cyclic manner as illustrated in FIG. 21.

Figure 21:
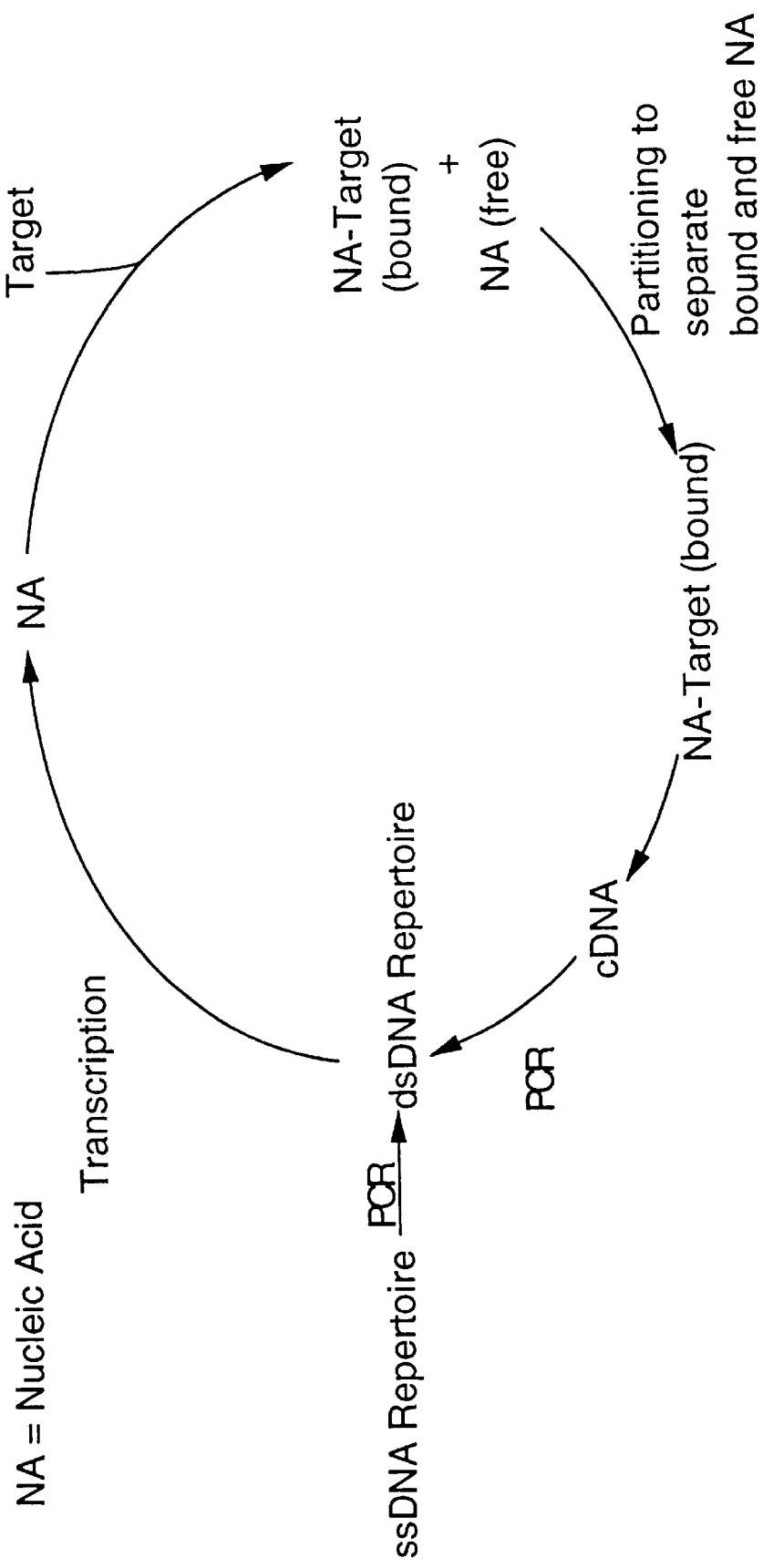
FIG. 21 illustrates the cyclical relationship between SELEX steps. A single-stranded nucleic acid repertoire of candidate oligonucleotides is generated by established procedures on a nucleic acid synthesizer, and is amplified by PCR to generate a population of double-stranded DNA molecules. Candidate DNA or RNA molecules are generated through asymmetric PCR or transcription, respectively, purified, and allowed to complex with a target molecule. This is followed by partitioning of bound and unbound nucleic acids, synthesis of cDNA, and PCR amplification to generate double-stranded DNA.

In the SELEX method, described by Tuerk and Gold (1990) Science 249:1155 and illustrated in FIG. 21, a single-stranded nucleic acid candidate mixture is generated by established procedures on a nucleic acid synthesizer, and is incubated with dNTP and Klenow fragment to generate a population of double-stranded DNA templates. The double-stranded DNA or the RNA transcribed from them are purified, and contacted with a target molecule. RNA sequences with enhanced affinity to the target molecule form nucleic acid-target complexes. This is followed by partitioning of bound and unbound nucleic acids, and separation of the target molecule from the bound nucleic acids. cDNA is synthesized from the enhanced affinity nucleic acids and double-stranded DNA generated by PCR amplification. The cycle is repeated until the complexity of the candidate mixture has decreased and its affinity as well as specificity to the target has been maximized.

A novel feature of the solution SELEX method is the means by which the bound and free members of the nucleic acid candidate mixture are partitioned. In one embodiment of the method of the present invention, generation of two physically distinct cDNA pools is accomplished by use of primer extension inhibition. One cDNA extension step is added to the basic SELEX protocol between steps 2 and 3 above, which allows the generation of two physically distinct cDNA pools—one having high affinity for the target and one having low affinity for the target—which are easily distinguished and separated from each other. Primer extension inhibition analysis is a common technique for examining site-bound proteins complexed to nucleic acids (Hartz et al. (1988) Methods Enzymol. 164:419), and relies on the ability of high affinity complexes to inhibit cDNA synthesis. Examples of protein-nucleic acid interactions studied by primer extension inhibition include ribosome binding to the mRNA ribosome-binding site (Hartz et al. (1988) Meth. Enzym. 164:419) as well as binding of the unique E. coli translation factor, SELB protein, to the mRNA selenocysteine insertion sequence (Baron et al. (1993) Proc. Natl. Acad. Sci. USA 90:4181).

Figure 22:
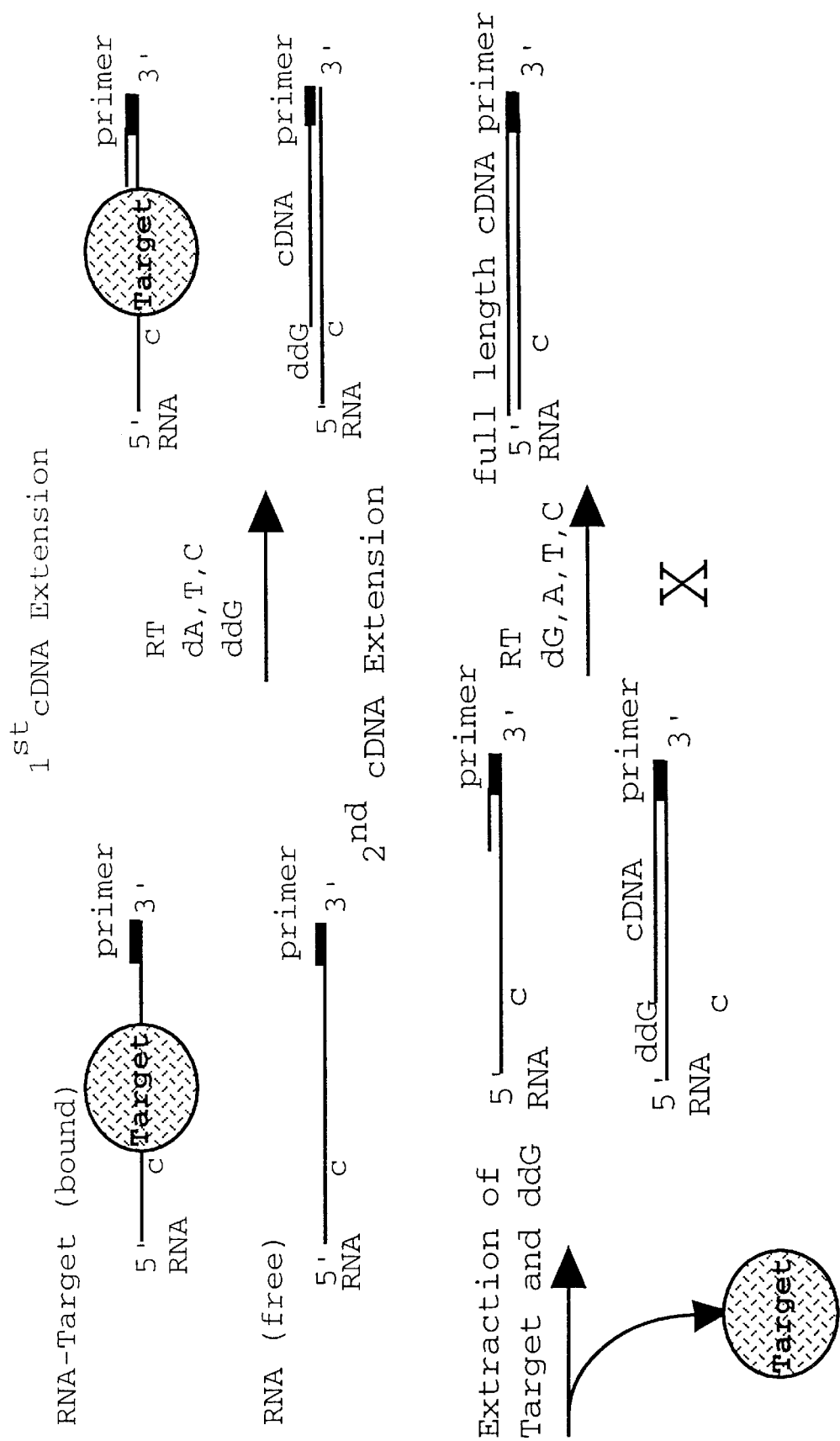
FIG. 22 illustrates one embodiment of the solution SELEX method in which primer extension inhibition is used to create differentiable cDNA pools—an amplifiable high affinity oligonucleotide cDNA pool and a non-amplifiable low affinity oligonucleotide cDNA pool. In this embodiment, the first cDNA extension is performed in the presence of chain terminating nucleotides such as ddG. After removal of the target molecule and dideoxynucleotides, the second cDNA extension is conducted in the presence of four dNTPs. Full-length cDNA is preferentially synthesized from the high affinity oligonucleotides and therefore, the high affinity cDNA pool is amplified in the subsequent PCR step.
Figure 23:
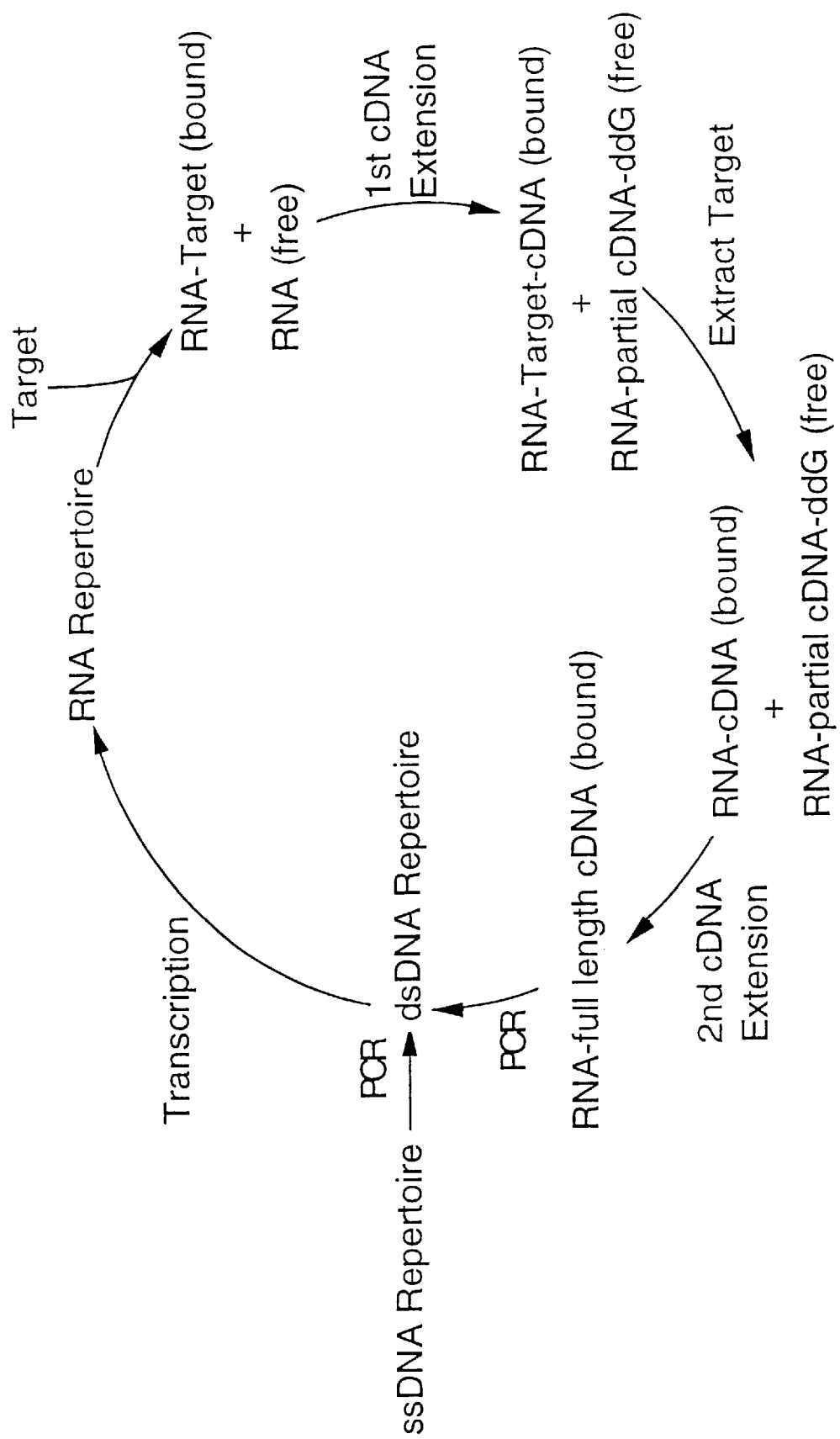
FIG. 23 illustrates the cyclic solution SELEX process for the embodiment shown in FIG. 22.

In one embodiment of the solution SELEX scheme, the first cDNA extension is performed in the presence of chain terminating nucleotide triphosphates. Under these conditions, oligonucleotides with low affinity for the target which form fast dissociating complexes with the target are converted into truncated cDNAs with a 3'-end terminated with a nonextendible nucleotide. The truncated cDNA chain is unable to anneal to the PCR primers, and therefore, is non-amplifiable. In contrast, tight complexes formed between high affinity oligonucleotides and the target molecule, characterized by slow dissociation rates, inhibit cDNA extension. The chain terminators are not incorporated into the nascent cDNA chain synthesized from the high affinity oligonucleotide because cDNA synthesis is blocked by the tightly bound target molecule. Full length cDNA from the high affinity complexes are obtained during a second round of cDNA extension in which the target and chain terminators have been removed from the system. Thus, weak affinity complexes are converted into truncated cDNA lacking the primer annealing site while tight complexes are converted into full length cDNA and are amplified by PCR (FIG. 22). The stringency of this method is easily modified by varying the molar ratio of chain terminators and dNTPs or the concentration of the polymerase, as primer extension inhibition is sensitive to polymerase concentration (Ringquist et al. (1993) Biochemistry 32:10245). As used in the present disclosure, the term "stringency" refers to the amount of free RNA that will be converted into PCR product.

Therefore, one crucial feature of the invention is its ability to partition strong and weak affinity complexes into amplifiable and non-amplifiable nucleic acid pools without requiring a partitioning matrix. It is the unique properties of these cDNA pools that allow selective amplification of the high affinity ligand.

The target molecule can be a protein (either nucleic acid or non-nucleic acid binding protein), nucleic acid, a small molecule or a metal ion. The solution SELEX method allows resolution of enantiomers as well as the isolation of new catalytic nucleic acids.

Primer extension inhibition may be achieved with the use of any of a number of nucleic acid polymerases, including DNA or RNA polymerases, reverse transcriptase, and Qβ-replicase.

The candidate mixture of nucleic acids includes any nucleic acid or nucleic acid derivative, from which a complementary strand can be synthesized.

Prior art partitioning included use of nitrocellulose or an affinity column. One disadvantage of the prior art partitioning was the phenomenon of matrix binders in which nucleic acids that specifically bind the partitioning matrix are selected along with those that specifically bind the target. Thus, one advantage of the method of the present invention is that it overcomes unwanted selective pressure originating with use of a partitioning matrix by only using such matrixes after nucleic acids with high affinity for the target have been partitioned in solution and amplified. Moreover, the ability to partition strong and weak affinity complexes during cDNA synthesis, based on the ability of only the strongest complexes to inhibit extension by a polymerase, results in the selection of only the highest affinity nucleic acid ligands. It is estimated that complexes with dissociation constants in the nanomolar or less range will efficiently block cDNA synthesis. The method of the present invention is expected to preferentially screen nucleic acid candidate mixtures for members that bind the target at this limit.

The use of primer extension inhibition allows partitioning of the oligonucleotide candidate mixture into two pools—those oligonucleotides with high target affinity (amplifiable) and those with low target affinity (non-amplifiable). As described above, chain terminators may be used to poison the first extension product, rendering the low affinity cDNAs non-amplifiable.

Figure 24:
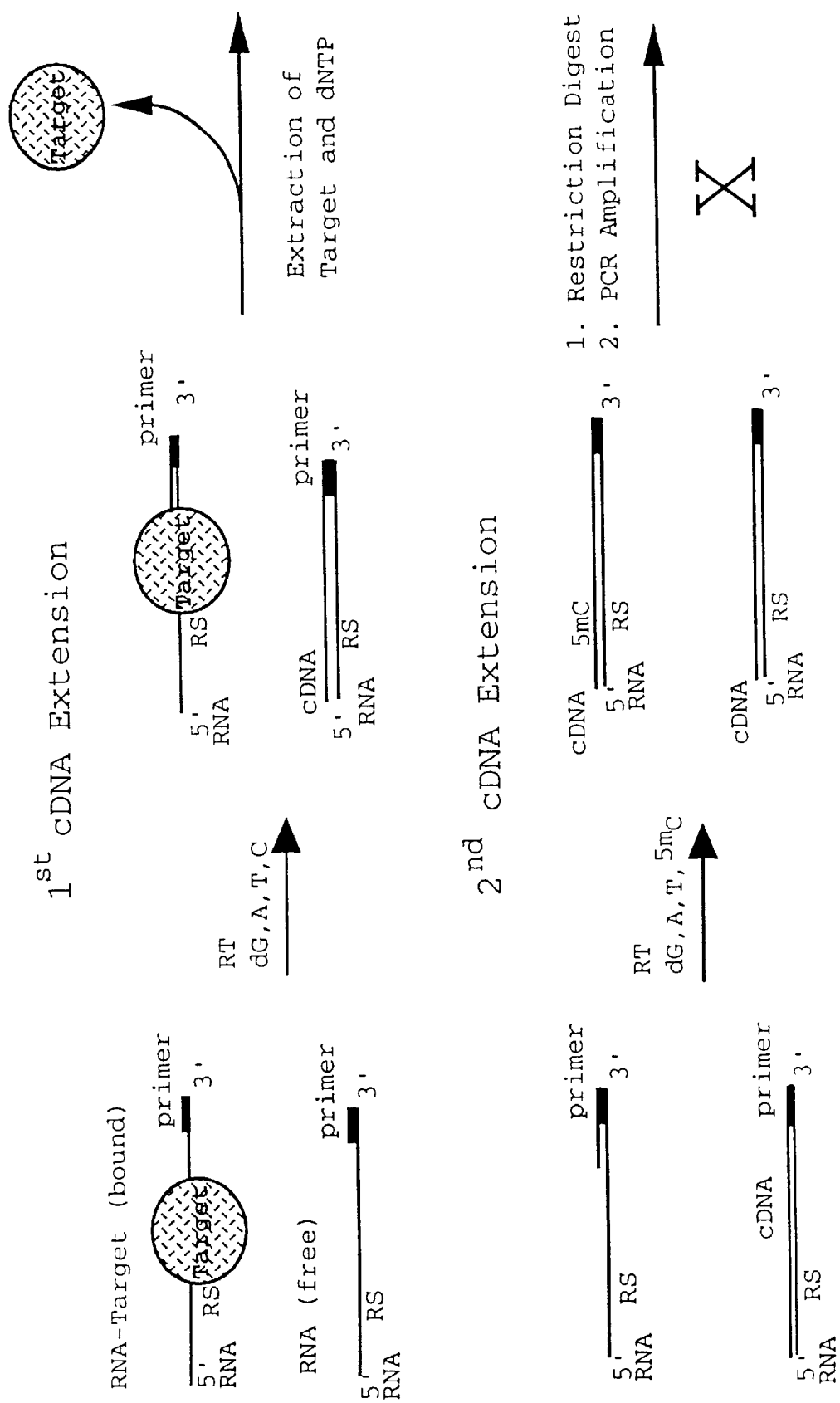
FIG. 24 illustrates one embodiment of the cyclic solution SELEX process wherein partitioning between oligonucleotides having high and low affinity to a target molecule is achieved by restriction enzyme digestion. In this embodiment, the first cDNA extension is conducted with four dNTPs and results in cDNAs corresponding to the low affinity oligonucleotides. The target is then removed and a second cDNA extension is conducted in the presence of modified nucleotides resistant to enzymatic cleavage. The cDNA pools are then incubated with restriction enzyme and only the cDNA pool corresponding to high affinity oligonucleotides is amplifiable in the subsequent PCR step.

In another embodiment of the method of the present invention, restriction enzymes are used to selectively digest the cDNA generated from the low affinity nucleic acids. A number of restriction enzymes have been identified that cleave single-stranded DNA. These enzymes cleave at specific sequences but with varying efficiencies. Partitioning of weak and strong affinity nucleic acids is accomplished by primer extension in the presence of the four dNTPs, followed by removal of the target and a second extension with modified nucleotides that are resistant to enzymatic cleavage. The cDNA pools can then be incubated with the appropriate restriction enzyme and the cDNA synthesized during the first extension cleaved to remove the primer annealing site and yield a non-amplifiable pool. Increased efficiency of cleavage is obtained using a hairpin at the restriction site (RS) to create a localized double-stranded region (FIG. 24).

In another embodiment of method of the present invention, cDNA sequences corresponding to low affinity nucleic acids are rendered selectively degradable by incorporation of modified nucleotide into the first cDNA extension product such that the resulting cDNA is preferentially degraded enzymatically or chemically.

Figure 25:
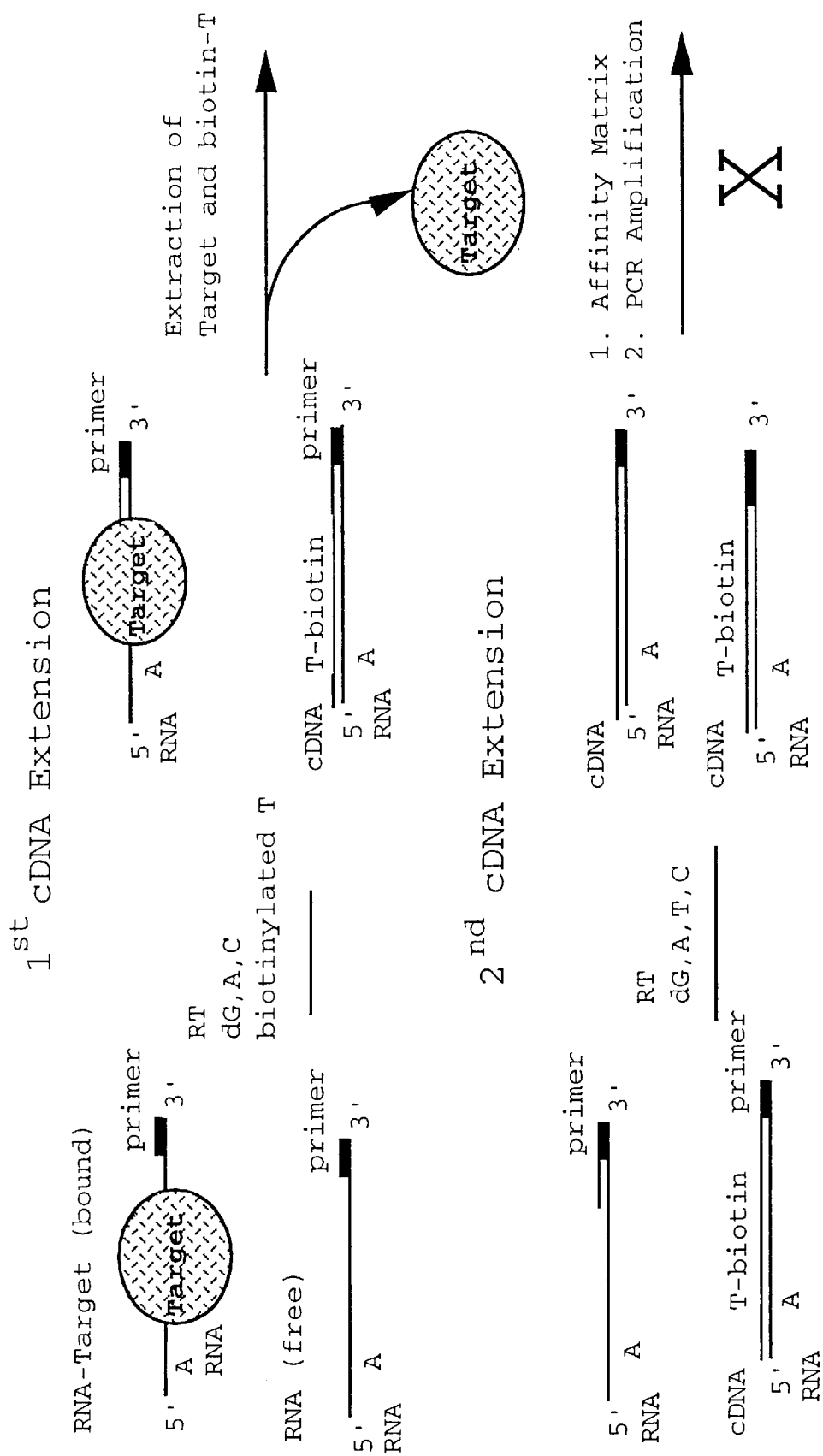
FIG. 25 illustrates one embodiment of the cyclic solution SELEX process wherein partitioning between oligonucleotides having high and low affinity to a target molecule is achieved by affinity chromatography. The first cDNA extension is performed in the presence of a modified nucleotide such as a biotinylated nucleotide, which allows the cDNA pool corresponding to the low-affuiity oligonucleotide to be retained on an affinity column.

In another embodiment of the method of the present invention, the first extension product can be removed from the system by an affinity matrix. Alternatively, the matrix could be used to bind the second extension product, e.g., the cDNAs corresponding to high affinity nucleic acids. This strategy relies on the incorporation of modified nucleotides during cDNA synthesis. For instance, the first cDNA extension could be performed in the presence of modified nucleotides (e.g., biotinylated, iodinated, thiolabelled, or any other modified nucleotide) that allow retention on an affinity matrix (FIG. 25). In an alternate embodiment of the method of the present minvention, a special sequence can also be incorporated for annealing to an affinity matrix. Thus, first synthesis cDNAs can be retarded on commercially obtainable matrices and separated from second synthesis cDNA, synthesized in the absence of the modified nucleotides and target.

In another embodiment of the invention, exonuclease hydrolysis inhibition is used to generate a pool of high affinity double-stranded nucleic acid ligands.

In yet another embodiment of the invention, the solution SELEX method is used to isolate catalytic nucleic acids.

In another embodiment of the invention, solution SELEX is used to preferentially amplify single-stranded nucleic acids.

In a further embodiment of the invention, the solution SELEX method is automated.

Removal of the target to allow cDNA synthesis from the high affinity nucleic acids can also be accomplished in a variety of ways. For instance, the target can be removed by organic extraction or denatured by temperature, as well as by changes in the electrolyte content of the solvent. In addition, the molecular repertoire of the candidate mixture that can be used with the invention include any from which a second complementary strand can be synthesized. Single-stranded DNA as well as RNA can be used, as can a variety of other modified nucleotides and their derivatives.

The following non-limiting examples illustrate the method of the present invention. Example 21 describes the solution SELEX process wherein partitioning between high and low affinity nucleic acids is achieved by primer extension inhibition. Example 22 illustrates the solution SELEX process wherein partitioning is achieved by restriction enzyme digestion of low affinity RNA. Example 23 describes the solution SELEX process wherein low affinity nucleic acids are separated from high affinity nucleic acids by affinity chromatography. Example 24 describes the isolation of high affinity double-stranded nucleic acid ligands with the use of exonuclease inhibition. Example 25 describes the isolation of catalytic nucleic acids. Example 26 describes an automated solution SELEX method.

The examples provided are non-limiting illustrations of methods of utilizing the present invention. Other methods of using the invention will become apparent to those skilled in the art from the teachings of the present disclosure.

EXAMPLE 1

Synthesis of RNA Sequences RNA-1, RNA-2, RNA-3, and RNA-7 and R17 Coat Protein

Figure 6:
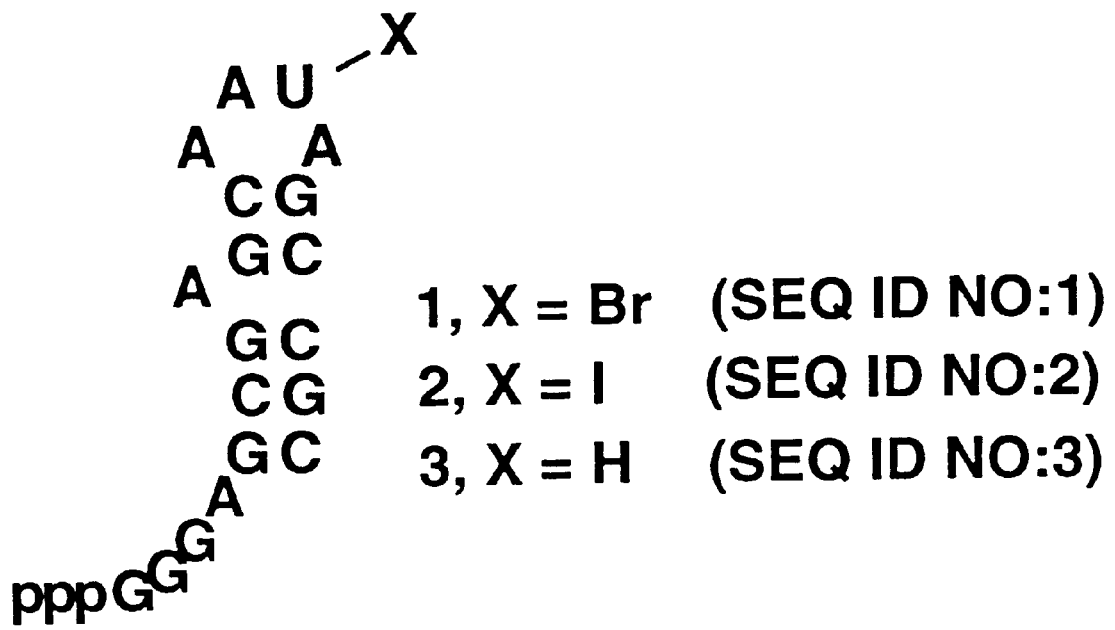
FIG. 6 shows the structures of hairpin RNA sequences RNA-1 (SEQ ID NO:1), RNA-2 (SEQ ID NO:2), and RNA-3 (SEQ ID NO:3) containing 5-bromouracil, 5-iodouracil, and uracil, respectively. These are variants of the wild-type hairpin of the R17 bacteriophage genome which bind tightly to the R17 coat protein.
Figure 12:
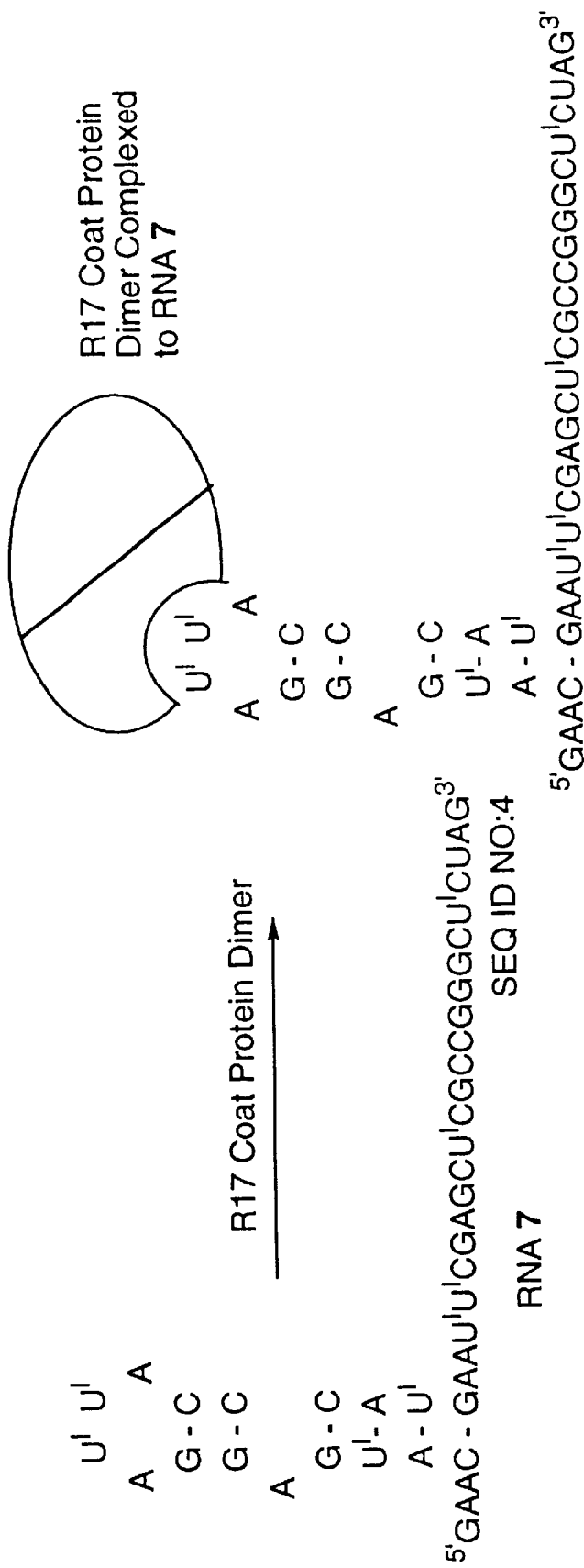
FIG. 12 pictures photocrosslinking of RNA-7 (SEQ ID NO:4) to R17 coat protein with 308 nm light followed by enzymatic digestion of most of the coat protein.
Figure 12:
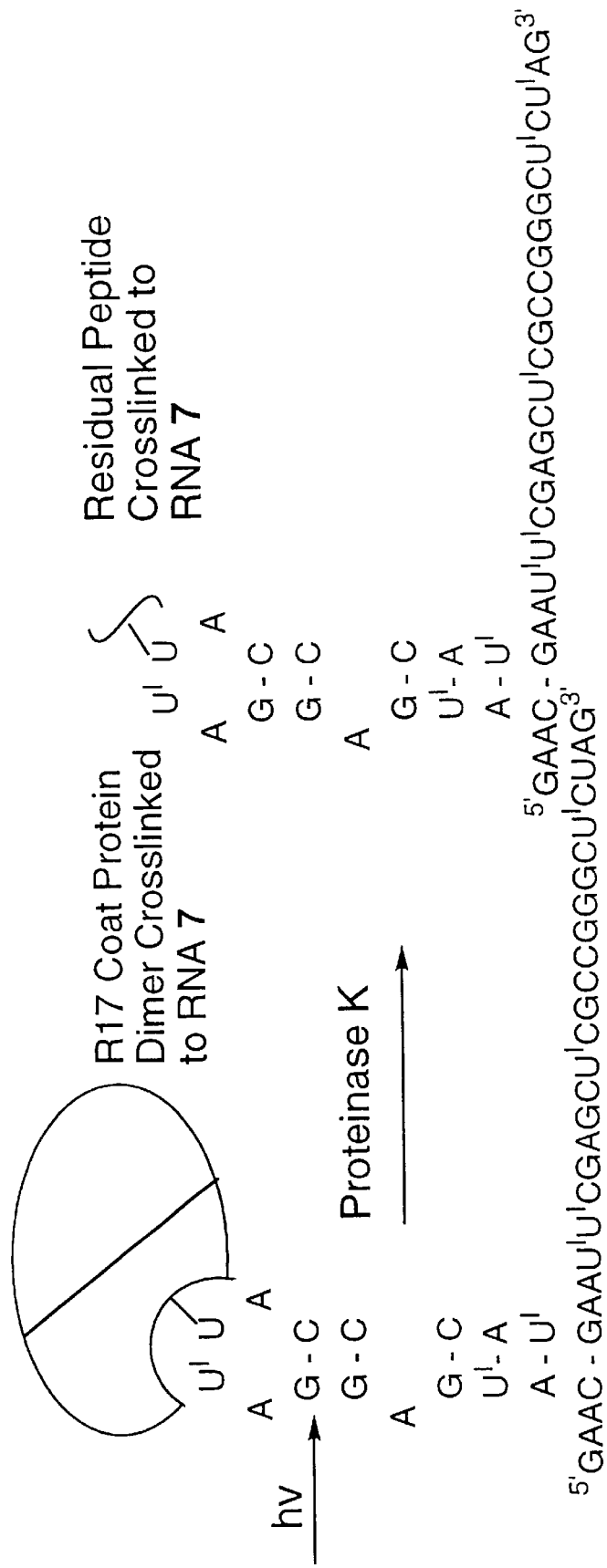
Figure 13:
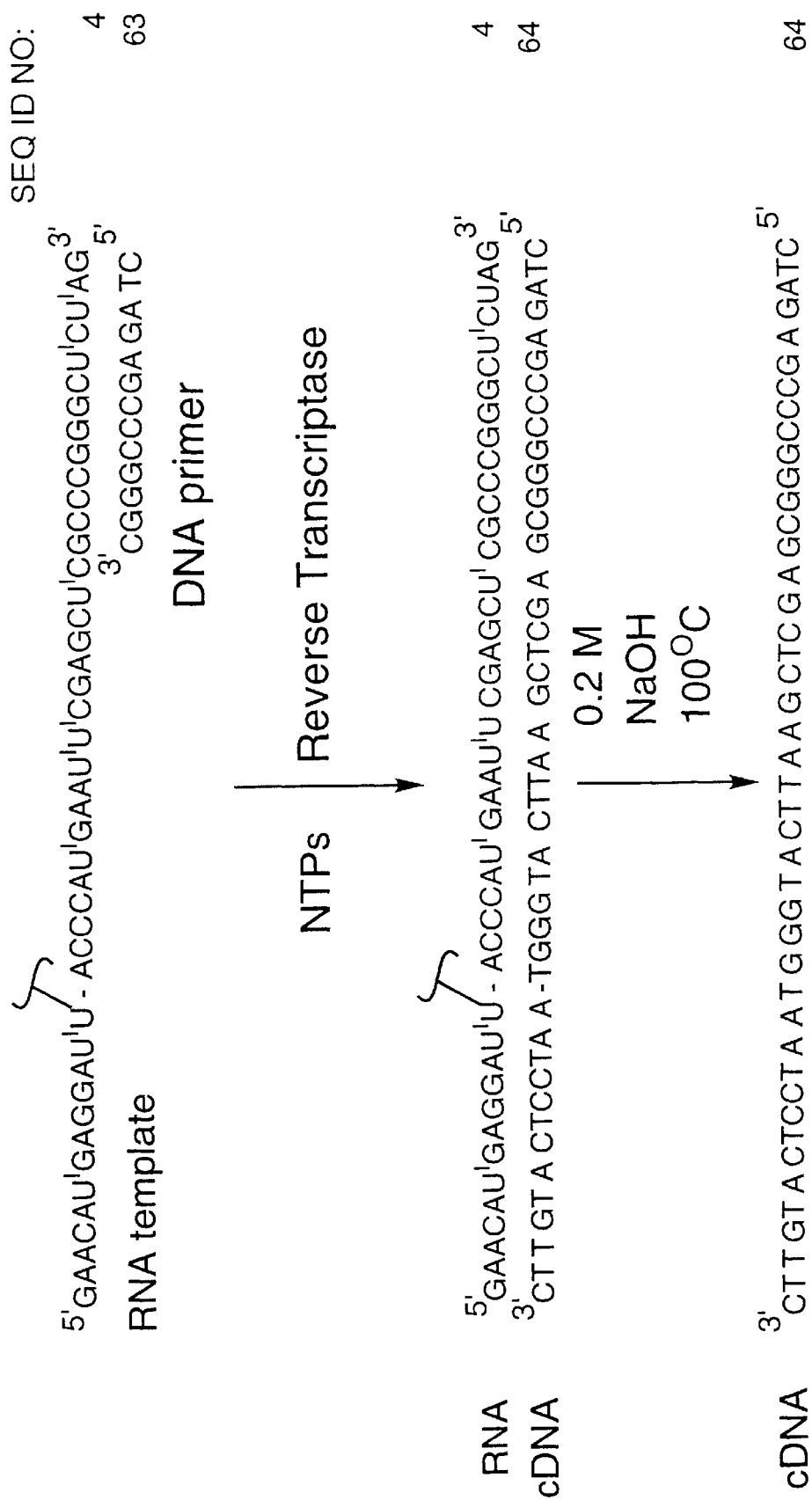
FIG. 13 shows formation of a complementary DNA from the RNA template after enzymatic digestion of the coat protein of FIG. 12 (SEQ ID NO:4).

RNA-1 (SEQ ID NO:1), RNA-2 (SEQ ID NO:2), and RNA-3 (SEQ ID NO:3) shown in FIG. 6 and RNA-7 (SEQ ID NO:4) shown in FIG. 12 were prepared by in vitro transcription from synthetic DNA templates or plasmids using methodology described by Milligan and co-workers (Milligan et al. (1987) Nucleic Acids Res. 15:8783). Transcription reactions contained 40 mM tris(hydroxymethyl) aminomethane hydrochloride (Tris-HCl, pH 8.1 at 37° C.), 1 mM spermidine, 5 mM dithiothreitol (DTT), 50 µg/ml of bovine serum albumin (BSA), 0.1% (v/v) Triton X-100, 80 mg/ml of polyethylene glycol ($m_r$ 8000), and 0.1 mg/ml of T7 RNA polymerase. Larger quantities of RNA were prepared with 3–5 mM of each of the nucleotide triphosphates (NTPs), 25 mM magnesium chloride, and 1 µM DNA template or 0.1 µg/ml of plasmid. Body-labeled RNAs were prepared in 100 µM reactions with 1 mM each of the three NTPs, 0.25 mM of the equivalent radiolabelled NTP ([α-$^{32}$P] NTP, 5 µCi), 15 mM $MgCl_2$, and 0.1 mg/ml of T7 RNA polymerase. Nucleotides, including 5-iodouridine triphosphate and 5-bromouridine triphosphate, were obtained from Sigma Chemical Co., St. Louis, Mo. RNA fragments were purified by 20% denaturing polyacrylamide gel electrophoresis (PAGE). The desired fragment was eluted from the polyacrylamide and ethanol-precipitated in the presence of 0.3 M sodium acetate. R17 bacteriophage was propagated in *Escherichia coli* strain S26, and the coat protein was purified using the procedure described by Carey and coworkers (Carey et al. (1983) Biochemistry 22:4723).

EXAMPLE 2

Binding Constants for RNA-1 and RNA-2 to R17 Coat Protein

Figure 7:
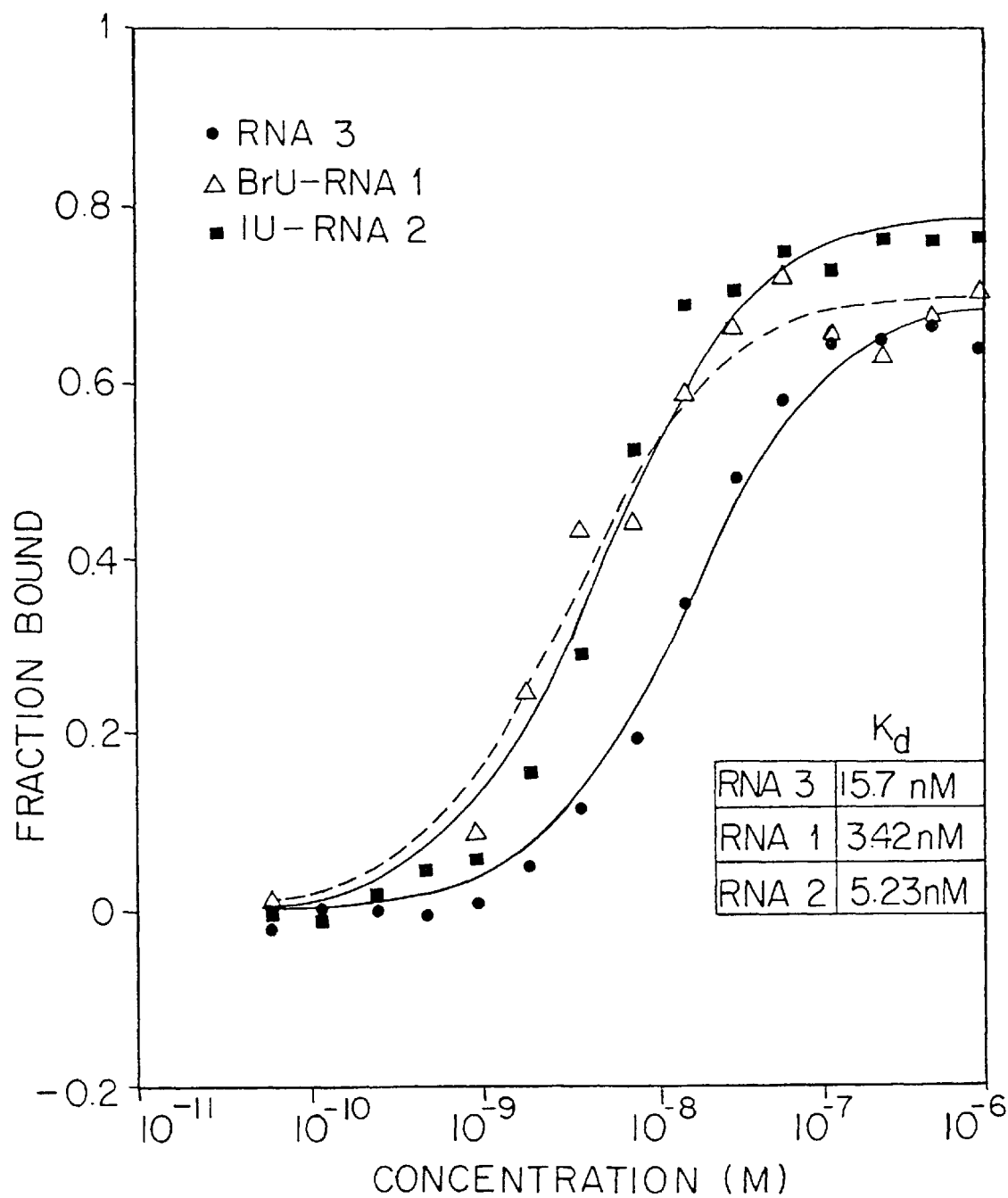
FIG. 7 shows binding curves for RNA-1 (SEQ ID NO:1), RNA-2 (SEQ ID NO:2), and RNA-3 (SEQ ID NO:3) to R17 coat protein. The binding constants calculated from the binding curves are also given.

RNA-protein binding curves for hairpin variants RNA-1 (SEQ ID NO:1), RNA-2 (SEQ ID NO:2) and RNA-3 (SEQ ID NO:3) to the bacteriophage R17 coat protein are shown in FIG. 7. The association constants between coat protein and the RNA hairpin variants were determined with a nitrocellulose filter retention assay described by Carey and co-workers (Carey et al. (1983) supra). A constant, low-concentration of $^{32}$P-labeled RNA was mixed with a series of coat protein concentrations between 0.06 nM and 1 µM in 10 mM magnesium acetate, 80 mM KCl, 80 µg/ml BSA, and 100 mM Tris-HCl (pH 8.5 at 4° C.) (TMK buffer). These were the same solution conditions used in the crosslinking experiments. After incubation at 4° C. for 45–60 min, the mixture was filtered through a nitrocellulose filter and the amount of complex retained on the filter determined by liquid scintillation counting. For each experiment the data points were fit to a non-cooperative binding curve and the $K_d$ value shown in FIG. 7 was calculated.

EXAMPLE 3

Figure 8:
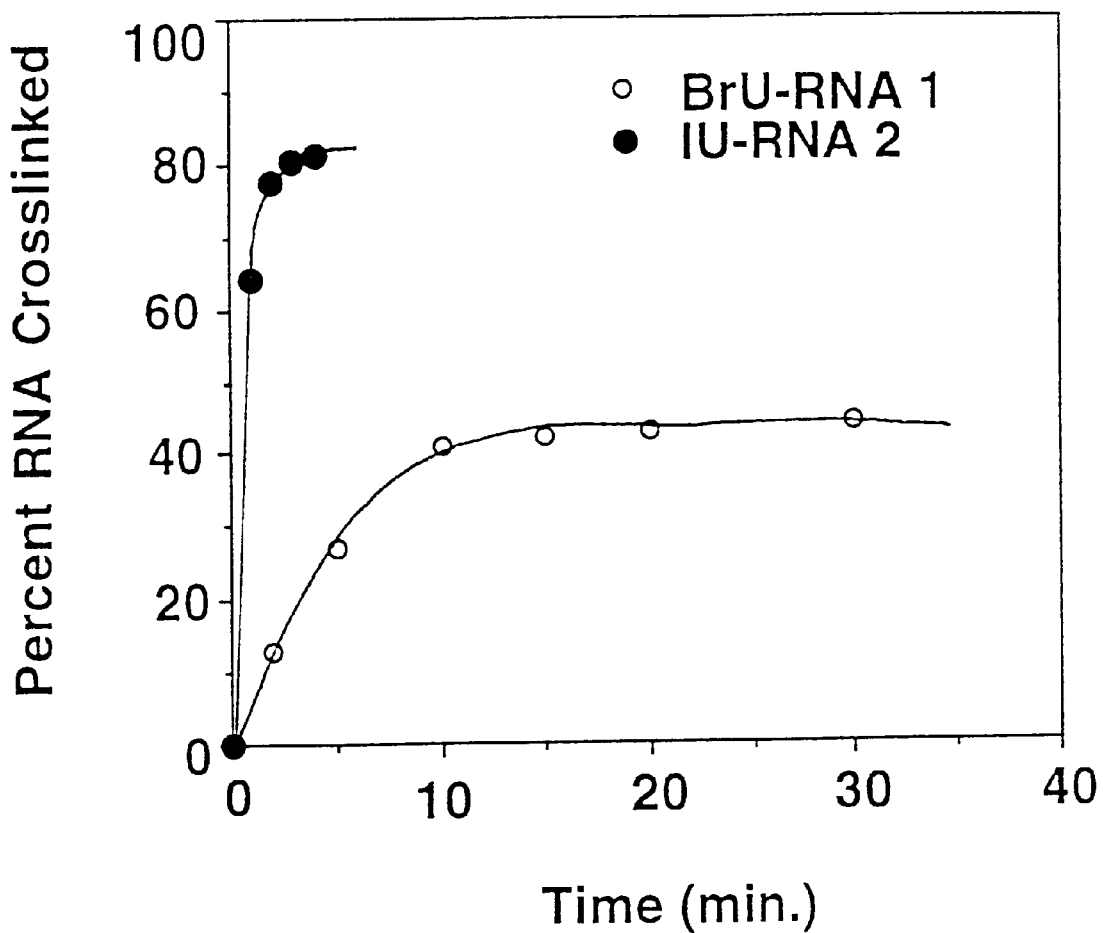
FIG. 8 shows the percent of RNA-1 (SEQ ID NO:1) and RNA-2 (SEQ ID NO:2) photocrosslinked to R17 coat protein with monochromatic irradiation at 308 nm from a XeCl excimer laser as a function of time. Photocrosslinking of RNA-1 (SEQ ID NO:1) maximized at 40% because of competitive photodamage to the coat protein during the irradiation period. Less photodamage to coat protein occurred with RNA-2 (SEQ ID NO:2) because of the shorter irradiation time.

Photocrosslinking of RNA-1 and RNA-2 to R17 Coat Protein at 308 nm $^{32}$P-Labeled RNA sequences RNA-1 (SEQ ID NO:1) and RNA-2 (SEQ ID NO:2) (5 nM) and R17 coat protein (120 nM) were each incubated on ice in 100 mM Tris-HCl (pH 8.5 at 4° C.), 80 mM KCl, 10 mM magnesium acetate, 80 µg/ml of BSA for 15–25 min before irradiations. These are conditions under which the RNA is fully bound to the coat protein. The RNAs were heated in water to 85° C. for 3 min and quick cooled on ice before use to ensure that the RNAs were in a hairpin conformation (Groebe and Uhlenbeck (1988) Nucleic Acids Res. 16:11725). A Lambda Physik EMG-101 excimer laser charged with 60 mbar of xenon, 80 mbar of 5% HCl in helium and 2360 mbar of helium was used for 308 nm irradiations. The output of the XeCl laser was directed unfocused toward a 4 mm wide by 1 cm path length quartz cuvette containing the RNA-protein complex. The laser was operated in the range of 60 mJ/pulse at 10 Hz; however, only about 25% of the laser beam was incident upon the reaction cell. Photocrosslinking yields of RNA-1 (SEQ ID NO:1) and RNA-2 (SEQ ID NO:2) to the R17 bacteriophage coat protein as a function of irradiation time are shown in FIG. 8. Crosslinked RNA was separated from uncrosslinked RNA by PAGE, and the yields were determined by autoradiography. Crosslinking of 5-bromouracil-containing variant RNA-1 (SEQ ID NO:1) maximized at about 40% because of competitive photodamage to the coat protein which inhibits binding to the RNA (Gott et al. (1991) supra). Less photodamage to coat protein occurred with RNA 2 because of the shorter irradiation time.

Crosslinking as a function of photons absorbed indicated that the quantum yield for crosslinking of BrU-RNA 1 is 0.014 and for crosslinking of IU-RNA-2 (SEQ ID NO:2), 0.006 with irradiation at 308 nm. In spite of the lower quantum yield, a higher crosslinking yield was obtained with IU-RNA 2 because of the seven times higher absorption probability of the IU chromophore at 308 nm. BrU and IU absorb at 308 nm with molar extinction coefficients of 385 and 2640 L/mol cm, respectively. Hence, a high level of photocrosslinking of the IU-RNA was achieved prior to protein damage.

EXAMPLE 4

Identification of the Amino Acid Residue Involved in the Crosslink of RNA-1 to R17 Coat Protein Large scale crosslinking of RNA-1 (SEQ ID NO:1) to R17 coat protein. A 10 ml solution containing 300 nM 5'-end-labeled RNA and 500 nM coat protein was incubated on ice in the presence of 100 mM Tris-HCl (pH 8.5 at 4° C.), 10 mM $Mg(OAc)_2$, 80 mM KCl, 80 mg bovine serum albumin (BSA), and 5 mM dithiothreitol (DTT) for 10–90 min. A Lambda Physik EMG-101 excimer laser was used for monochromatic irradiation at 308 nm. The beam output was measured at 69±5 mJ/pulse at 10 Hz. Approximately 50% of the beam was focused through a 7 mm-diameter circular beam mask into a 1 cm path length quartz cuvette in a thermostated cell holder. The laser power was measured with a Scientech 360–001 disk calorimeter power meter. The temperature was regulated at 4±2° C. with a Laude RC3 circulating bath.

The 10 ml reaction mixtures were prepared just prior to the irradiations which were performed in 2 ml fractions. After 5 min of irradiation the protein concentration was brought to 1 µM. The reaction mixture was then incubated for 3 min to allow exchange of photodamaged protein for fresh protein in the nucleoprotein complex and irradiated for an additional 5 min. This step was repeated nine times to give 90 ml of irradiated sample. The crosslinking, analyzed by 20% denaturing PAGE, and quantitated on a Molecular Dynamics Phosphoimager, revealed 22% crosslinking.

The 90 ml sample contained 5.9 mnol of crosslinked RNA, 21 nmol of free RNA, 97 nmol of free coat protein, and 7.2 mg of BSA. The total volume was reduced to 20 ml and split equally between two 50 ml polypropylene screw cap centrifuge tubes (Nalgene) and ethanol precipitated overnight at −20° C. The RNA and proteins were spun down to a pellet at 13,000 rpm in a fixed angle J-20 rotor with an Beckman J2-21 centrifuge. Each pellet was resuspended in 1 ml of 0.5 M urea, 50 mM Tris-HCl pH 8.3, and 0.2% SDS for 48 h at 4° C. with shaking. The fractions were combined, and the SDS was then removed by precipitation so as not to decrease the activity of trypsin. This was achieved using 40 mM KCl, and the precipitate was removed by spinning through a 0.22 μm cellulose acetate spin filter. The trypsin conditions were optimized using 500 μl of the solution.

Proteolvtic Digestion. The remaining 1.5 ml of crosslinked RNA solution containing free RNA and protein was brought to 6 ml to contain 1 M urea, 20 mM $CaCl_2$, and 6 mM DTT, and then 1.61 mg (1:5 w/w.) trypsin-TPCK (251 units/mg) was added. The reaction proceeded at 36° C. for 2 h at which time 1.61 mg more trypsin was added. At 4 h a 100 μL aliquot was removed and the reaction stopped by quick freezing. The reaction was analyzed by 20% polyacrylamide 19:1 crosslinked, 7 M urea, 90 mM Tris-borate/2 mM EDTA (TBE) gel electrophoresis (20% urea denaturing PAGE).

Purification of the digested crosslinked RNA. The trypsin reaction mixture was brought to 10 ml to reduce the molar concentration of salt, and run through a 240 μl DEAE ion exchange centrifuge column. The column was washed with 100 mM NaCl and spun dry in a bench top centrifuge to remove free peptide. The column bound material containing the RNA and crosslinked tryptic fragment was eluted from the column with 1 ml of 600 MM NaCl and the column spun dry. An additional 200 μl of 600 mM NaCl was spun through the column. The two fractions were pooled, ethanol precipitated and pelleted at 10,000 rpm for 35 min at 4° C. The pellet was resuspended in 25 μl of 7 M urea-TBE buffer, 10 mM DTT, 0.1% bromophenol blue, 0.1% xylene cylanol, and heated to 85° C. for 4 min and purified by 20% denaturing PAGE. The gel ran for 3.5 h at 600 V. A 5 min phosphoimage exposure was taken of the gel. The digested protein-RNA crosslink was then electrolytically blotted from the gel onto a PVDF protein sequencing membrane (0.2 micron) from Bio-RAD. The membrane was air dried, coomassie stained for 1 min, destained for 2 min in 50% MeOH: 50% $H_2O$, and rinsed twice with deionized $H_2O$. An autoradiogram was made of the membrane to visualize the digested protein RNA crosslink which was excised from the membrane and submitted for Edman degradation. The immobilized peptide was sequenced by automated Edman degradation, performed on an Applied Biosystems 470A sequencer using manufacturer's methods and protocols (Clive Slaughter, Howard Hughes Medical Institute, University of Texas, Southwestern). The Edman analysis indicated that the position of the crosslink was tyrosine-85 based upon the known amino acid sequence (Weber (1983) Biochemistry 6:3144).

EXAMPLE 5

Photocrosslinking of RNA-2 to R17 Coat Protein at 325 nm

Figure 9:
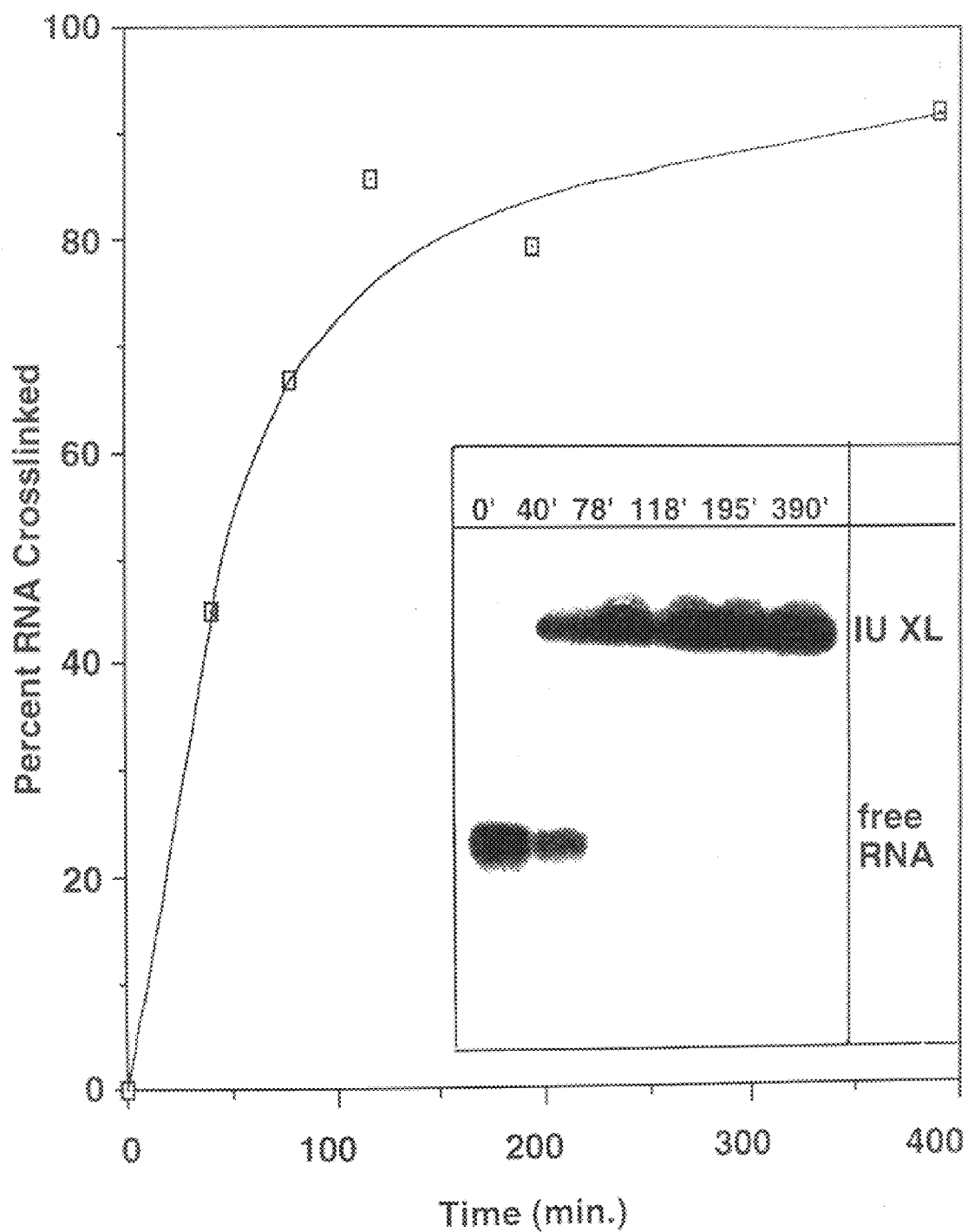
FIG. 9 shows the percent of RNA-2 (SEQ ID NO:2) photocrosslinked to R17 coat protein with monochromatic irradiation at 325 mn from a HeCd laser as a function of time. The data are also presented in the original electrophoretic gel format. The symbol IU XL marks RNA crosslinked to protein. A near-quantitative yield of photocrosslinking was obtained.

In an experiment analogous to that described in Example 3, IU-substituted RNA-2 (SEQ ID NO:2) was photocrosslinked to R17 coat protein with monochromatic emission at 325 nm from an Omnichrome HeCd laser (model 3074-40M325). The power output of the HeCd laser was 37 mW and the total beam of diameter 3 mm was incident upon the sample. To increase excitation per unit time the beam was reflected back through the sample with a dielectric-coated concave mirror. Crosslinked RNA was separated from uncrosslinked RNA by PAGE, and the yields were determined with a Phosphoinager. The percent of the RNA crosslinked to the protein as a function of irradiation time is shown in FIG. 9. High-yield crosslinking occurred without photodamage to the R17 coat protein. In a separate experiment analogous irradiation of coat protein alone at 325 nm with yet a higher dose resulted in protein which showed the same binding constant to R17 coat protein. Irradiation at 325 nm of BrU-containing RNA-1-R17 coat protein complex did not result in crosslinking because the BrU chromophore is transparent at 325 nm.

EXAMPLE 6

Figure 10:
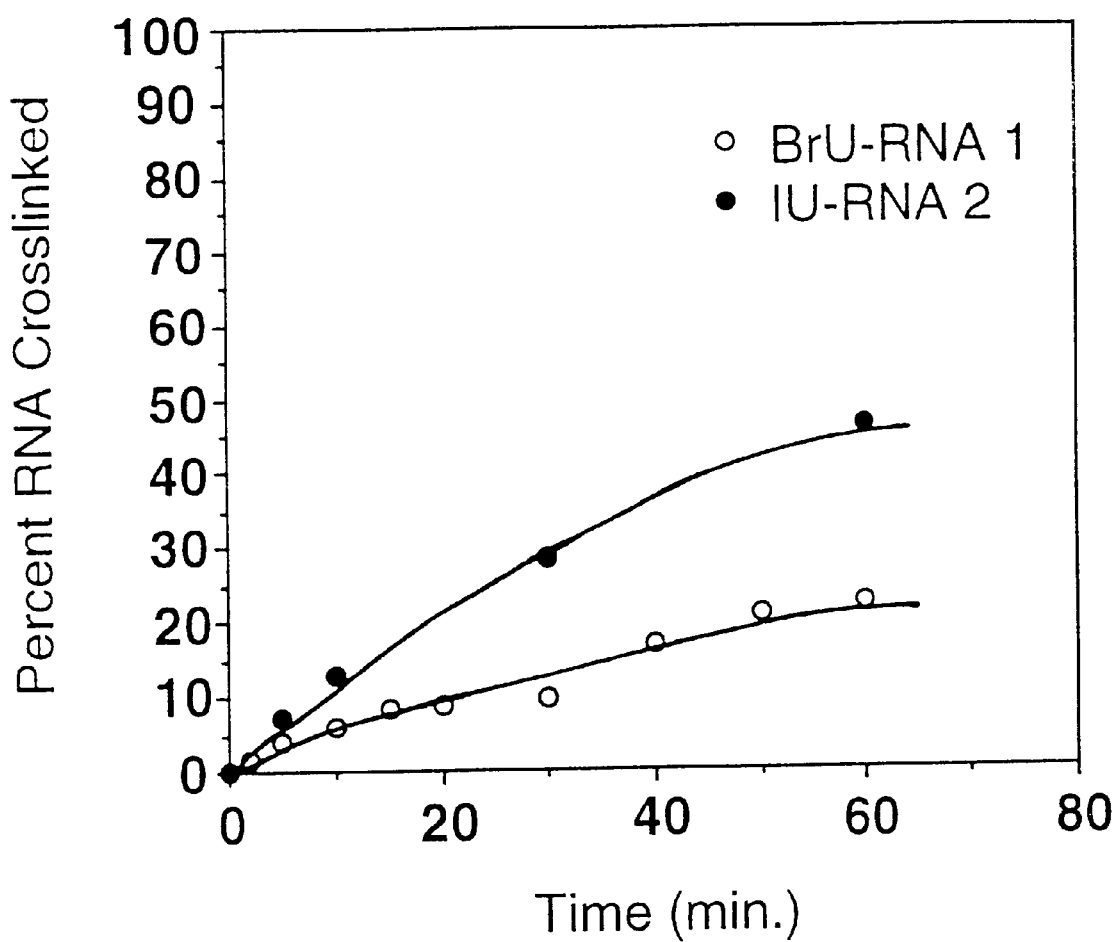
FIG. 10 shows the percent of RNA-1 (SEQ ID NO:1) and RNA-2 (SEQ ID NO:2) photocrosslinked to R17 coat protein with broad-band irradiation in the region of 312 nm from a Transilluminator as a function of time. Less than quantitative yields of photocrosslinking were obtained because of photodamage to the protein and possibly to the RNA sequences.

Photocrosslinking of RNA-1 and RNA-2 to R17 Coat Protein with a Transilluminator In an experiment analogous to that described in Example 3, RNA-1 (SEQ ID NO:1) and RNA-2 (SEQ ID NO:2) were photocrosslinked to the R17 coat protein with broad-band emission in the range of 312 nm from a Fisher Biotech Transilluminator (model FBTIV-816) filtered with polystyrene. Crosslinked RNA was separated from uncrosslinked RNA by PAGE, and the yields were determined by autoradiography. Percent RNAs crosslinked to protein as a function of irradiation time is shown in FIG. 10.

EXAMPLE 7

Photoreaction of 5-Iodouracil with N-Acetyltvrosine N-Ethyl Amide

Figure 11:
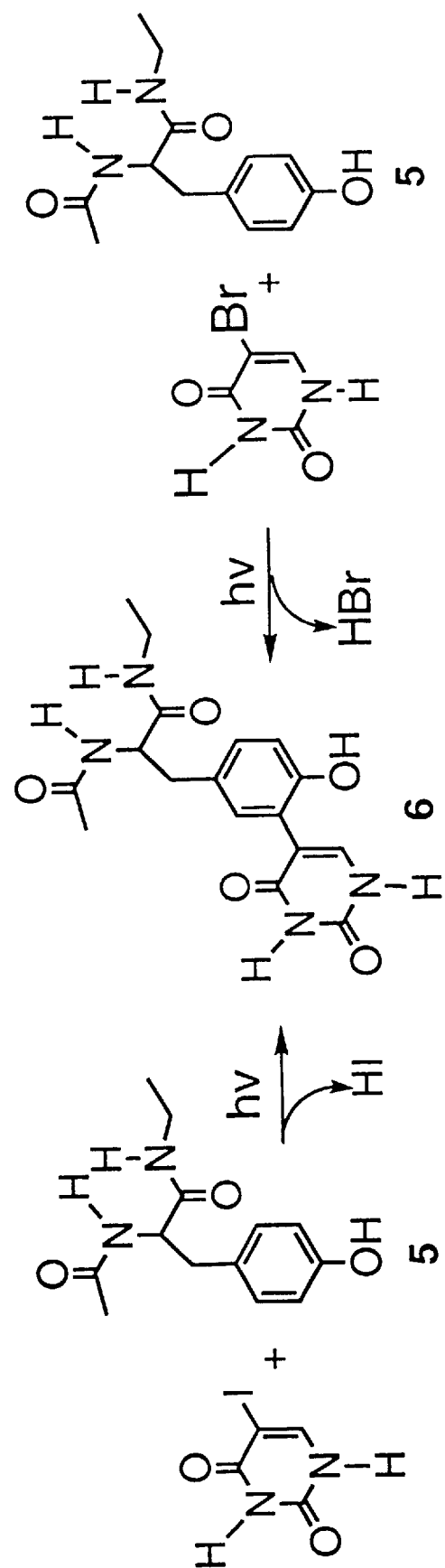
FIG. 11 shows formation of the same product, Structure 6, from irradiation at 308 nm of 5-iodouracil and 5-bromouracil in the presence of excess N-acetyltyrosine N-ethylamide (Structure 5).

N-acetyltyrosine N-ethylamide was prepared as described by Dietz and Koch (1987) supra. Irradiation of a pH 7, aqueous solution of iodouracil and 10 mol equivalent excess of N-acetyltyrosine N-ethyl amide at 308 nm with a XeCl excimer laser gave a photoadduct identical to the photoadduct (structure 6) from irradiation of bromouracil and N-acetyltyrosine N-ethylamide (Dietz and Koch (1987) supra) as shown in FIG. 11. Product comparison was performed by C-18 reverse phase HPLC and by $^1H$ NMR spectroscopy. Although little is known about the mechanism of photocrosslinking of IU-substituted nucleic acids to associated proteins, this result suggests that it is similar to that of photocrosslinking of BrU-substituted nucleic acids to associated proteins.

EXAMPLE 8

Preparation of a cDNA from an RNA Photocrosslinked to a Protein

Figure 14:
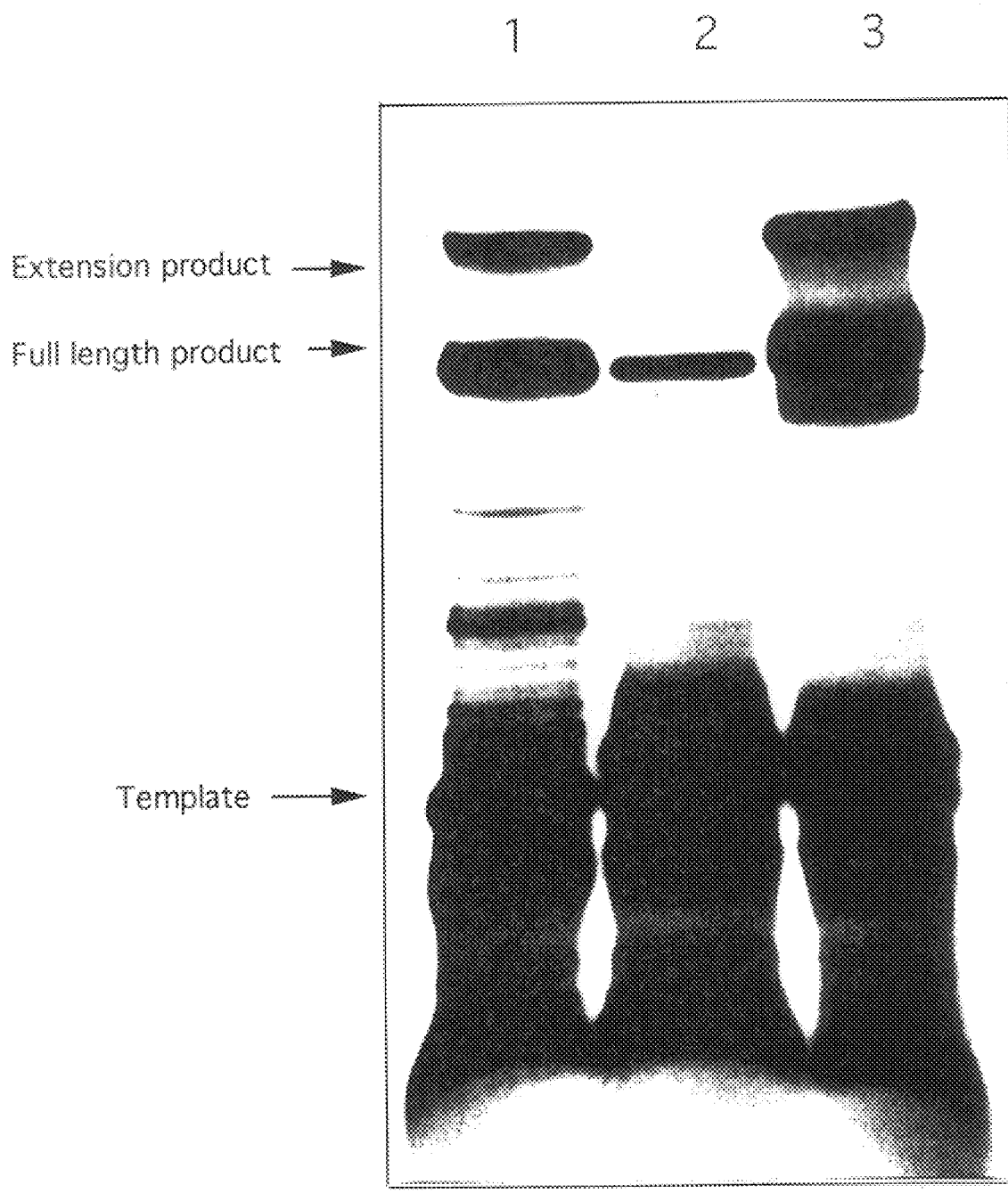
FIG. 14 shows the polyacrylamide gel of Example 8 showing production of a cDNA from an RNA template bearing modified nucleotides as shown in FIGS. 12 and 13. The modified nucleotides were 5-iodouracil and uracil substituted at the 5-position with a small peptide. Based upon model studies shown in FIG. 11, the peptide was most likely attached to the uracil via the phenolic ring of a tyrosine residue.

RNA-7 (SEQ ID NO:4) (FIG. 11) was prepared using methodology as reported in Example 1 using a plasmid instead of a DNA template. The photocrosslinking was performed as described in Example 3. A 4 ml reaction mixture consisting of 6.75 nM RNA and 120 nM R17 coat protein was irradiated, 2 ml at a time, at 308 nm with unfocused emission from a XeCl excimer laser. The laser produced 50 mJ/pulse and was operated at 10 Hz. The reaction proceeded to near quantitative crosslinking, 85–90%, in 5 min of irradiation. After crosslinking, 1 ml of the total reaction mixture was removed; EDTA (80 mM), SDS (0.1%), and $CaCl_2$ (0.1 mM) were added; the free (unbound) RNA present was purified away; and the protein digested with Proteinase K at 60° C. for 30 min. The RNA bound to residual protein was ethanol precipitated to remove salts and spun to a pellet. The pellet was washed three times with 70% ethanol to remove any residual salts. A reverse transcription reaction was employed to make a complementary DNA copy of the RNA template. A 13-base promoter was annealed to the RNA and the reverse transcription reaction was performed under the standard conditions of the manufacturer, Gibco (Gaithersburg, Md.), and was stopped after 1 hr. The cDNA was body labelled with $^{32}P$-labelled deoxycytidine triphosphate. The RNA template was then removed by hydrolyzing with 0.2 M sodium hydroxide at 100° C. for 5 min. The formation of the cDNA was followed by PAGE. A hydrolysis ladder and markers were added to the gel to determine the length of the cDNA. The cDNA co-migrated with the 44 nucleotide RNA template. If there had been a stop in the cDNA as a result of crosslinking modification, a shortened product of 31 nucleotides would have been observed. A small amount of a stop product was observed in the 22–25 nucleotide region of the gel, but this may have resulted from the hairpin secondary structure which begins at position 25 of the cDNA on the RNA template. No stop in the 31 nucleotide region of the gel appeared; this established that the reverse transcriptase had read through the position of the crosslink. A diagram of the gel appears in FIG. 14.

EXAMPLE 9

Iodocytosine Photocrosslinking 5-iodocytosine (IC) was incorporated in a hairpin RNA (RNA 8) that contained cytosine at the -5 position and bound the R17 coat protein with high affinity. The IC-bearing RNA is designated RNA 9. RNA 9 (5 nM) and R17 coat protein (120 nM) were incubated on ice in 100 mM Tris-HCl (pH 8.5 at 4° C.)/80 mM KCl/10 mM magnesium acetate/80 µg/ml BSA for 15–25 min prior to irradiation. The RNA in water was heated to 85° C. for 3 min and quick cooled on ice before use to ensure that it would be in a conformation that bound the coat protein (Groebe and Uhlenbeck (1988) supra). The complex was irradiated for 5 min at 4° C., and the experiment was compared to control irradiations of RNA 2 and RNA 8 coat protein complexes. Irradiation of RNA 8-coat protein complex resulted in no crosslinked product. Iradiation of RNA 9-coat protein complex resulted in the formation of a crosslink that formed in high yield (70–80%) similar to the yield of the control irradiation of RNA 2-coat protein complex (80–90%) Crosslinking of RNA 9 is presumed to occur through a similar mechanism as RNAs containing IU at position -5 of the loop hairpin (FIGS. 6 and 12). This assumption is based on the specificity of the crosslink since RNA 8 did not photocrosslink.

EXAMPLE 10

Incorporation of Halogenated Nucleotides into DNA Ligands

Photoreactive nucleotides may be incorporated into a DNA ligand capable of crosslinking to a target molecule upon irradiation by the methods discussed above. 5-Bromodeoxyuracil (BrdU), 8-bromo-2'-deoxyadenine, and 5-iodo-2'-deoxyuracil are examples of such photoreactive nucleotides.

EXAMPLE 11

PhotoSELEX

In one embodiment of the present invention, the photoSELEX method is applied to completion in the selection of a nucleic acid ligand which binds and photocrosslinks to a target molecule.

A randomized set of nucleic acid oligonucleotides is synthesized which contain photoreactive groups. The oligonucleotides of the candidate mixture may be partially or fully saturated at each available position with a photoreactive group. The candidate mixture is contacted with the target molecule and irradiated at the appropriate wavelength of light. Oligonucleotides crosslinked to the target molecule are isolated from the remaining oligonucleotides and the target molecule removed. cDNA copies of the isolated RNA sequences are made and amplified. These amplified cDNA sequences are transcribed into RNA sequences in the presence of photoreactive groups, and the photoSELEX process repeated as necessary.

EXAMPLE 12

Selection of Enhanced Photocrosslinking Ligands: SELEX Followed by PhotoSELEX

In one embodiment of the method of the present invention, selection of nucleic acid ligands through SELEX is followed by selection through photoSELEX for ligands able to crosslink the target molecule. This protocol leads to ligands with high binding affinity for the target molecule that are also able to photocrosslink to the target.

Photoreactive nucleotides are incorporated into RNA by T7 polymerase transcription with the reactive nucleotide triphosphate in place of a specified triphosphate. For example, 5-bromouridine triphosphate is substituted for uridine triphosphate or 8-bromo-adenosine triphosphate is substituted for adenosine triphosphate. A randomized set of RNA sequences containing photoreactive nucleotides are generated and the SELEX methodology applied. The initial SELEX rounds are used to eliminate intrinsically poor binders and enhance the pool of molecules that converge to form a pool of RNAs that contain the photoreactive group(s) and which bind to the target molecule. Aliquots from the initial SELEX rounds are irradiated and the enhancement of photocrosslinking followed via PAGE as the rounds proceed. As a slower migrating band representing crosslinked products starts to become evident, the pool of RNAs are introduced into rounds of photoSELEX. RNAs that have a photoreactive group adjacent to a reactive amino acid residue in the nucleoprotein complexes form a crosslink and are selected and RNAs that do not have reactive nucleotides in proximity to reactive target residues are eliminated.

This protocol selectively applies photoSELEX selection to previously identified ligands to a target molecule.

EXAMPLE 13

PhotoSELEX Followed by SELEX

In another embodiment of the method of the present invention, an RNA ligand able to photocrosslink a target molecule is preselected through the photoSELEX methodology. Subsequently, SELEX is performed to select a crosslinking oligonucleotide for ability to bind the target molecule.

EXAMPLE 14

Limited SELEX Followed by PhotoSELEX

In this embodiment of the present invention, nucleic acid ligands are selected through the SELEX process for a limited number of selection rounds. SELEX is not applied to completion as in Example 12. Rather, the candidate mixture is partially selected for oligonucleotides having relatively enhanced affinity for the target molecule. The random oligonucleotides of the candidate mixture contain photoreactive groups and the initial SELEX selection is conducted in the absence of irradiation. PhotoSELEX is then performed to select oligonucleotides able to crosslink to the target molecule.

This protocol allows the selection of crosslinking ligands from a pool of oligonucleotides with a somewhat enhanced capacity to bind the target molecule and may be useful in circumstances where selection to completion through SELEX does not yield crosslinking ligands.

EXAMPLE 15

Limited Directed PhotoSELEX

In one embodiment of the method of the present invention, in which nucleic acid ligands identified through SELEX are subjected to limited randomization, followed by selection through photoSELEX.

The construction of the DNA template used to transcribe the partially randomized RNA is based on the sequence of the initially selected ligand and contains at each position primarily the nucleotide that is complementary to that position of the initial selected RNA sequence. However, each position is also partially randomized by using small amounts of each of the other three nucleotides in the sequencer, which varies the original sequence at that position. A limited RNA pool is then transcribed from this set of DNA molecules with a photoreactive triphosphate replacing a specific triphosphate in the reaction mix (i.e., BrU for U). The partially randomized set of RNA molecules which contains the photoreactive nucleotides is mixed with a quantity of the target protein. Bound RNAs that have a photoreactive group adjacent to a reactive amino acid residue in the nucleoprotein complex form covalent crosslinks upon irradiation. RNAs that bind and crosslink are selected through several rounds of photoSELEX and separated away from RNAs that bind but do not crosslink.

EXAMPLE 16

Methods for Modifying a Target Molecule

In another embodiment of the method of the present invention, photoSELEX is applied to develop a ligand capable of modifying a target molecule. Under these circumstances, incorporation of a photoreactive group onto or into a ligand selected by photoSELEX or SELEX may modify the target in several ways such that the biological activity of the target molecule is modified. For example, the target molecule may be inactivated by photocrosslinked ligand. Mechanisms of inactivation include electron or hydrogen abstraction from the target molecule or radical addition to the target molecule that elicit a chemical modification. These different mechanisms may be achieved by changing the mode of irradiation.

A ligand selected through photoSELEX used as a diagnostic for a target molecule with ultraviolet (UV) light may also inactivate the same target in vivo if the source of irradiation is changed to X-rays or gamma rays. The resultant vinyl radical may work similarly to a hydroxyl radical, that is, by abstraction of hydrogen atoms from the binding domain of the target molecule.

X-ray irradiation of the R17 coat protein bound to radiolabelled IU- or BrU-substituted RNA hairpin sequences may result in the formation of a crosslink. The BrU or IU chromophore may also be excited to a higher energy state by X-ray irradiation resulting in the formation of a vinyl radical (Mee (1987) in: *Radiation Chemistry: Principles and Applications* (Farhataziz and Rodgers, eds.), VCH Publishers, New York, pp. 477–499). The radical abstracts a hydrogen from the binding domain of the R17 coat protein, thereby reducing or inhibiting its ability to bind the RNA ligand. Inactivation is tested by X-ray irradiation of the RI 7 coat protein in the presence and absence of substituted RNAs. The formation of crosslinked complexes is analyzed by PAGE. The effect of X-ray irradiation of RNA resulting in modification of binding by modification of the protein domain is followed by nitrocellulose binding assay.

EXAMPLE 17

Diagnostic Use of PhotoSELEX To Identify Unique Proteins Associated with Specific Disease Processes A goal of diagnostic procedures is to correlate the appearance of unique proteins with specific disease processes. Some of these correlations are obvious, e.g., after bacterial or viral infections, one can detect antigens which are antigen specific or antibodies to such antigens not found in the blood of uninfected subjects. Less obvious correlations include the appearance in serum of α-foeto protein which is directly correlated with the presence of the most common form of testicular cancer.

The photoSELEX method may be applied to the discovery of heretofore unknown correlations between biological proteins and important human diseases. In one embodiment of the present invention, serum is taken from a patient with a disease, RNA ligands to all the proteins in the serum are produced and adsorbed to normal sera. RNA ligands to serum proteins may be identified through the SELEX method, with subsequent incorporation of photoreactive groups, or may be identified through photo-SELEX, initially selected from a candidate mixture of oligonucleotides containing one or more photoreactive groups. RNA ligands left unbound are those which specifically bind only unique proteins in the serum from patients with that disease. For example, RNA ligands are initially identified to a limited number of serum proteins (e.g., 11). The RNA ligands identified contain a modified NTP having a reversible or photoreactive functional group capable of crosslinking reversibly or non-reversibly with the target protein. Optionally, the presence of a cross-linked ligand to every protein may be verified. The RNA ligands are then removed and amplified. RNA is then transcribed for a second SELEX round. RNA is now bound to a large excess of 10 of the original 11 proteins, leaving an RNA ligand specific for the unique (11th) protein. This RNA is then amplified. This is a subtractive technique.

In one embodiment of the diagnostic method of the present invention, the method described above is used to identify a ligand to an abnormal protein, for example, an α-foeto protein. Sera from patients with important diseases is obtained and RNA ligands to all proteins present identified. The RNA ligands are adsorbed to normal sera, leaving an unbound ligand. The unbound ligand is both a potential diagnostic agent and a tool for identifying serum proteins specifically associated with a disease.

EXAMPLE 18

Method of Treating Disease by In Vivo Use of Photocrosslinking Nucleic Acid Ligand A nucleic acid ligand to a target molecule associated with a disease state is selected through the photoSELEX process (Example 11). The photoSELEX selected nucleic acid ligand may be introduced into a patient in a number of ways known to the art. For example, the non-halogenated photoSELEX ligand is cloned into stem cells which are transferred into a patient. The ligand may be transiently or constitutively expressed in the patient's cells. IC administered to the patient is incorporated into the oligonucleotide product of the cloned sequence. Upon irradiation, the ligand is able to crosslink to the target molecule. Irradiation may include visible, 325 nm, 308 nm, X-ray, ultraviolet, and infrared light.

Alternatively, the photoSELEX ligand may be taken into a patient's cells as a double-stranded DNA which is transcribed in the cell in the presence of iodinated cytosine. Further methods of introducing the photoSELEX ligand into a patient include liposome delivery of the halogenated ligand into the patient's cells.

EXAMPLE 19

PhotoSELEX Ligands for Use in In Vitro Diagnostic, In Vivo Imaging and Therapeutic Delivery PhotoSELEX may be used to identify molecules specifically associated with a disease condition and/or abnormal cells such as tumor cells. PhotoSELEX-identified oligonucleotides may be produced that react covalently with such marker molecules.

In one embodiment of the present invention, the target for photoSELEX is the abnormal serum or tumor cell (e.g., the target mixture). A library candidate mixture of oligonucleotides is generated containing photoreactive groups. Using one of the above-described photoSELEX protocols, oligonucleotides able to photocrosslink to the unique proteins in the abnormal serum or on the tumor cells are identified. Oligonucleotides able to crosslink to a marker protein on a tumor cell are useful as in vitro diagnostics or when coupled to enhancing agents for in vitro imaging. Further, oligonucleotides able to crosslink to a marker protein on a tumor cell may be used therapeutically, for example, as a method for immune activation, as a method of inactivation, or as a method of delivering specific target-active pharmaceutical compounds.

EXAMPLE 20

PhotoSELEX and HIV-1 Rev

At each position of the template deoxy-oligonucleotide synthesis, the nucleotide reagent ratio was 62.5:12.5:12.5:12.5. The nucleotide added in greater amount at each position corresponds to the nucleotide found in the 6a sequence (SEQ ID NO:5) at the same position.

Cloning and Sequencing procedure: RNA's isolated from each round were reverse transcribed to produce cDNA and PCR amplified producing a 111 bp fragment with unique BamnHI and HindIII restriction sites at the ends. The phenol/CHCl$_3$ treated fragment and a pUC18 vector were digested together overnight with BamHI and HindIII at 37° C., phenol/CHCl$_3$ treated and precipitated. The digested vector and PCR product was ligated at room temperature for 4 hours with T4 DNA ligase and transformed into competent DH5α-F'cells which were then grown on ampicillin-containing LB plates. Individual colonies were grown overnight in LB-ampicillin media and plasmid was prepared using Wizard (Promega) plasmid preparation kit. Sequencing was performed utilizing a Sequenase (USB) kit.

Conditions for nitrocellulose filter binding selections: All rounds utilized approximately 20 nM RNA. Round 1 and 2: 6 nM Rev. Round 3: 3 nM Rev. Round 8: 1 nM Rev. Round 9–10: 3 nM Rev. Binding reaction volumes ranged from 5 mls to 1 ml.

Conditions for crosslinking selections: Approximately 50–100 nM of folded pool RNA was added to 0.2 (Rounds 4–6) or 0.5 (Round 7) μM Rev, 1 μM BSA in 1×BB (50 mM TrisAc pH 7.7, 200 mM KOAc, 10 mM DTT) on ice and incubated 5 minutes at 37° C. The samples were then irradiated at 37° C., for 3 minutes at 308 nm by a XeCl excimer laser (round 4), 30 minutes at 325 nm by a HeCd laser (round 5), 10 minutes at 325 mn, (round 6), or 1 minute at 325 nm, (round 7). Approximately one-half of the sample was heated in 50% formamide, 40 μg tRNA at 90° C. for 4 minutes and separated by electrophoresis in an 8 percent polyacrylamide/8 M urea gel.

The following procedure was utilized to elute crosslinked RNAs from acrylamide gels with approximately 80% recovery: The nucleoprotein containing gel slice was crushed to a homogenous slurry in 1×PK buffer (100 mM Tris-Cl pH 7.7, 50 mM NaCl and 10 mM EDTA). Proteinase K was added to 1 mg/ml concentration and incubated at 42° C. for 30 minutes. Fifteen minute incubations at 42° C. with increasing urea concentrations of approximately 0.7 M, 1.9 M, and 3.3 M were performed. The resulting solution was passed through DMCS treated glass wool and 0.2 μm cellulose acetate filter. The filtered solution was extracted twice with phenol/CHCl$_3$ and then precipitated with a 1:1 volume mixture of EtOH:isopropanol.

The crosslinked band from each round was placed in scintillation fluid and counted in a Beckman LS-133 Liquid Scintillation System. The percent crosslinked=cpms of crosslinked product from RNA+Rev after 4 minutes irradiation at 325 mn minus cpms in crosslinked region for RNA only irradiated divided by total cpms. The fold increase in crosslinking is % R13 crosslinked divided by % D37 crosslinked.

Simultaneous selection for affinity and crosslinking using competitor tRNA was performed as follows. 10 μM yeast tRNA was added to 0.5 μM Rev, 1 μM BSA in 1×BB (50 mM TrisAc (pH=7.5), 200 mM KOAc, 10 mM DTT) and incubated 10 minutes on ice. 200,000 cpms (approximately 50–100 nM final concentration RNA) was added and incubated an additional 15 to 60 minutes on ice followed by 5 minutes at 37° C. The samples were then irradiated 4 minutes at 325 nm by a HeCd laser at 37° C. Approximately one-third of the sample was heated in 50% formamide, 40 μg tRNA at 90° C. for 4 minutes and separated by electrophoresis in an 8 percent polyacrylamide-8M urea gel.

The LI crosslinking RNA ligands form additional crosslinked product with a 4 minute 325 nm laser irradiation.

The template oligos used to produce the truncated RNA's are: PTS-1; 5'-TAATACGACTCACTATA-3', (SEQ ID NO:60) DNA-2; 5'-GAGTGGAAACACACGTGGTGTTT-CATACACCCTATAGTGAGTCGTATTA-3' (SEQ ID NO:61), and DNA-24; 5'-AGGGTTAACAGGTGTGCCTGTTAATCCCCTATA GT-GAGTCGTATTA-3' (SEQ ID NO:62). PTS-1 was annealed with DNA-2 or DNA-24 to produce a template for T7 transcription.

To calculate the number of changes for individual molecules compared to 6a (SEQ ID NO:5), each was aligned to 6a for maximum similarity. Gaps are calculated as one change and truncated molecules were counted as unchanged. To calculate the average probability of finding molecules within each class; the average number of specific (s) and non-specific (ns) changes and unchanged (u) were calculated and used in the equation: $(P)=(0.125)^s(0.375)^{ns}(0.625)^u$. Class Ia $(P)=9\times10^{-15}$; Ib $(P)=3\times10^{-15}$; Ic $(P)=7\times10^{-13}$; Id $(P)=3\times10^{-15}$; Class II$(P)=2\times10^{-14}$. Since the starting population consists of $10^{14}$ molecules, sequences with $(P)<10^{-14}$ will not be represented. (s) are those changes required to produce the uppercase, consensus nucleotides and (ns) are additional changes.

Trunc24 (SEQ ID NO:59) photo-independent crosslinking with HIV-1 Rev in the presence of human nuclear extracts was determined as follows: Trunc24 RNA, nuclear extracts, and Rev protein were combined and incubated on ice for 10 min. Samples were mixed 1:1 with 8 M urea loading buffer and placed on a 7 M urea, 8% polyacrylamide gel for analysis, XL indicates the nucleoprotein complex, RNA indicates free trunc24 RNA.

EXAMPLE 21

Primer Extension Ihibition Solution SELEX

Primer extension inhibition relies on the ability of a tightly bound target molecule to inhibit cDNA synthesis of high affinity oligonucleotides and results in formation of an amplifiable cDNA pool corresponding to high affinity oligonucleotides and a non-amplifiable cDNA pool corresponding to low affinity oligonucleotides. Thus, the PCR step of solution SELEX acts as a partitioning screen between two cDNA pools. General protocols for nucleic acid synthesis, primer extension inhibition and PCR are herein provided. Further, N-acryloylamino phenyl mercuric gel electrophoretic conditions for separation of selected nucleic acid ligands is described. The methods of cloning and sequencing nucleic acid ligands is as described by Tuerk and Gold (1990) supra.

RNA Synthesis. The RNA candidate mixture was generated by incubating RNA polymerase and DNA templates. The reaction conditions are 8% polyethylene glycol 8000, 5 mM dithiothreitol, 40 mM Tris-HCl (pH 8.0), 12 mM $MgCl_2$, 1 mM spermidine, 0.002% Triton X-100, 2 mM nucleotide triphosphates, and 1 unit/µl RNA polymerase. Reactions are incubated at 37° C. for 2 hours.

The transcription protocol may be used to generate RNAs with modified nucleotides. The transcription reaction may either be primed with a nucleotide triphosphate derivative (to generate a modified 5' end), modified nucleotides may be randomly incorporated into the nascent RNA chain, or oligonucleotides or their derivatives ligated onto the 5' or 3' ends of the RNA product.

Primer Extension Ihibition. Primer extension inhibition is performed as described by Hartz et al. (1988) supra. Briefly, an oligonucleotide primer is annealed to the 3' end of the oligonucleotides of the candidate mixture by incubating them with a 2-fold molar excess of primer at 65° C. for 3 min in distilled water. The annealing reaction is cooled on ice, followed by the addition of 1/10 volume of 10× concentrated extension buffer (e.g., 10 mM Tris-HCl (pH 7.4), 60 mM $NH_4Cl$, 10 mM Mg-acetate, 6 mM β-mercaptoethanol, and 0.4 mM nucleotide triphosphates). Primer extension is initiated by addition of polymerase and incubation at any of a variety of temperatures ranging between 0–80° C., and for times ranging from a few seconds to several hours. In one embodiment of the method of the present invention, primer extension is first conducted in the presence of chain terminating nucleotide triphosphates such that low-affinity nucleic acids preferentially incorporate these chain terminators. A second primer extension is then conducted after removing the target from high affinity nucleic acids and removing the chain terminating nucleotides triphosphates.

Polymerase Chain Reaction. The polymerase chain reaction (PCR) is accomplished by incubating an oligonucleotide template, either single- or double-stranded, with 1 unit/µl thermal stable polymerase in buffer (50 mM KCl, 10 mM Tris-HCl (pH 8.6), 2.5 mM $MgCl_2$, 1.7 mg/ml BSA, 1 mM deoxynucleotide triphosphates, and 1 µM primers). Standard thermal cycles are 95° C. for 30 sec, 55° C. for 30 sec, and 72° C. for 1 min., repeated as necessary. One modi of the PCR protocol generates single-strand DNA by incubating either single- or double-stranded template with a single, elongated primer oligonucleotides and results in an elongated product. PCR preferentially amplifies the oligonucleotides rendered amplifiable in the primer extension steps described above.

(N-Acryloylamino)phenyl mercuric gel electrophoresis. Polyacrylamide gel electrophoresis using N-acryloylamine phenyl mercury (APM) was performed as described by Igloi (1988) Biochemistry 27:3842. APM was synthesized by mixing 8 ml of acetonitrile to 0.35 g of (p-aminophenyl) mercuric acetate at 0° C., followed by 2 ml of 1.2 M $NaHCO_3$. A total of 0.2 ml of acryloyl chloride was then added with vigorous stirring and the reaction incubated overnight at 4° C. The solid phase was collected by centrifugation and washed with water, dissolved by warming to 50° C. in 8.5 ml of dioxane, followed by filtration to remove undissolved contaminants. APM crystals were formed upon standing at room temperature and the solid was washed again with water and dried under vacuum. APM was stored at 4° C. APM-polyacrylamide gels were prepared by addition of a appropriate aliquot of a 1 mg/ml solution of APM in formamide to a solution containing a given amount of acrylamide, bis(acrylamide), an urea in 0.1 M Tris-borate/EDTA (pH 8.3). Polymerization was initiated by addition of 0.5 ml of 1% ammonium persulfate and 7 µl of TEMED per 10 ml of gel solution.

EXAMPLE 22

Enzymatic or Chemical Degradation Solution SELEX

Enzymes or chemicals may be used to selectively degrade the pool of cDNA corresponding to low-affinity oligonucleotides. In one embodiment of the present invention, restriction enzymes are used to selectively degrade the cDNA pool corresponding to low-affinity oligonucleotides. A number of restriction enzymes have been identified that cleave single-stranded DNA. These enzymes cleave at specific sequences but with varying efficiencies.

Restriction enzyme digestion may be performed with a variety of sequence specific restriction endonucleases. Endonucleases that cleave single-stranded DNA include DdeI, HaeIII, HgaI, HinfI, HinPI, MnII, PstI, and RsaI. These enzymes are used under standard conditions known to those skilled in the field of molecular biology. Double-stranded nucleic acids may also be cleaved using the proper combination of nucleic acid restriction sequences and site specific restriction nucleases.

The basic solution SELEX procedure is followed as described in the SELEX Patent Applications. The first cDNA extension is performed in the presence of four dNTPS, followed by removal of the target. The second cDNA extension is performed with modified nucleotides that are resistant to enzymatic cleavage by restriction endonucleases. The mixture of cDNA extension products is incubated with the appropriate restriction enzyme. The product of the first cDNA extension from free nucleic acid is cleaved to remove the primer annealing site, rendering this cDNA pool non-amplifiable by PCR. The efficiency of cleavage by restriction endonucleases may be improved using a hairpin at the restriction site (RS) to create a localized double-stranded region, as shown in FIG. 24.

Alternatively, the first cDNA extension product is rendered selectively degradable by other classes of enzymes by incorporation of modified nucleotides. For example, cDNA corresponding to low affinity ligands may be synthesized with nucleotides sensitive to uracil DNA glycosylase, while cDNA corresponding to high affinity ligands may incorporate resistant nucleotides.

Chemical degradation of cDNA corresponding to low affinity ligands can be accomplished by incorporation of 7-methylguanosine, 5-bromouracil, or 5-iodouracil as described using piperidine or photodegradation (Sasse-Dwight and Gralla (1991) Methods Enzymol. 208:146; Aiken and Gumport (1991) Methods Enzymol. 208:433; Hockensmith et al. (1991) Methods Enzymol. 208:211).

EXAMPLE 23

Solution SELEX Followed by Affinity Chromatography

Selective removal of either the first or second cDNA extension products may be achieved through affinity chromatography. Removal of the first cDNA extension product preferentially removes the cDNA pool corresponding to free or low-affinity nucleic acids. Removal of the second cDNA extension product preferentially retains cDNA corresponding to the high-affinity ligand. This strategy relies on the incorporation of modified nucleotides during cDNA synthesis.

Selective Removal of First Extension Product. Following the basic solution SELEX protocol, the first cDNA extension is performed in the presence of modified nucleotides (e.g., biotinylated, iodinated, thiolabelled, or any other modified nucleotide) that allow retention of the first cDNA pool on an affinity matrix (FIG. 25). The target is then removed and the second cDNA extension performed in the presence of non-modified nucleotides. The cDNAs that have incorporated the modified nucleotides may be removed by affinity chromatography using a column containing the corresponding affinity ligand. The cDNA pool corresponding to nucleic acids with high affinity for the target remain and are then amplified by PCR.

Selective Removal of the Second Extension Product. Following the basic protocol, the first cDNA extension is performed in the presence of four dNTPs, and the second cDNA extension is performed in the presence of modified nucleotides (e.g., biotinylated, iodinated, thiolabelled, or any other modified nucleotide) that allow retention of the second cDNA pool on an affinity matrix as described above.

Incorporation of Specific Sequences for Annealing to An Affinity Matrix. In an alternate embodiment of the method of the present invention, a special sequence can also be selectively incorporated for annealing to an affinity matrix. Thus, either first or second synthesis cDNAs can be retarded and purified on commercially obtainable matrices as desired.

EXAMPLE 24

Exonuclease Ihibition Solution SELEX

Figure 26:
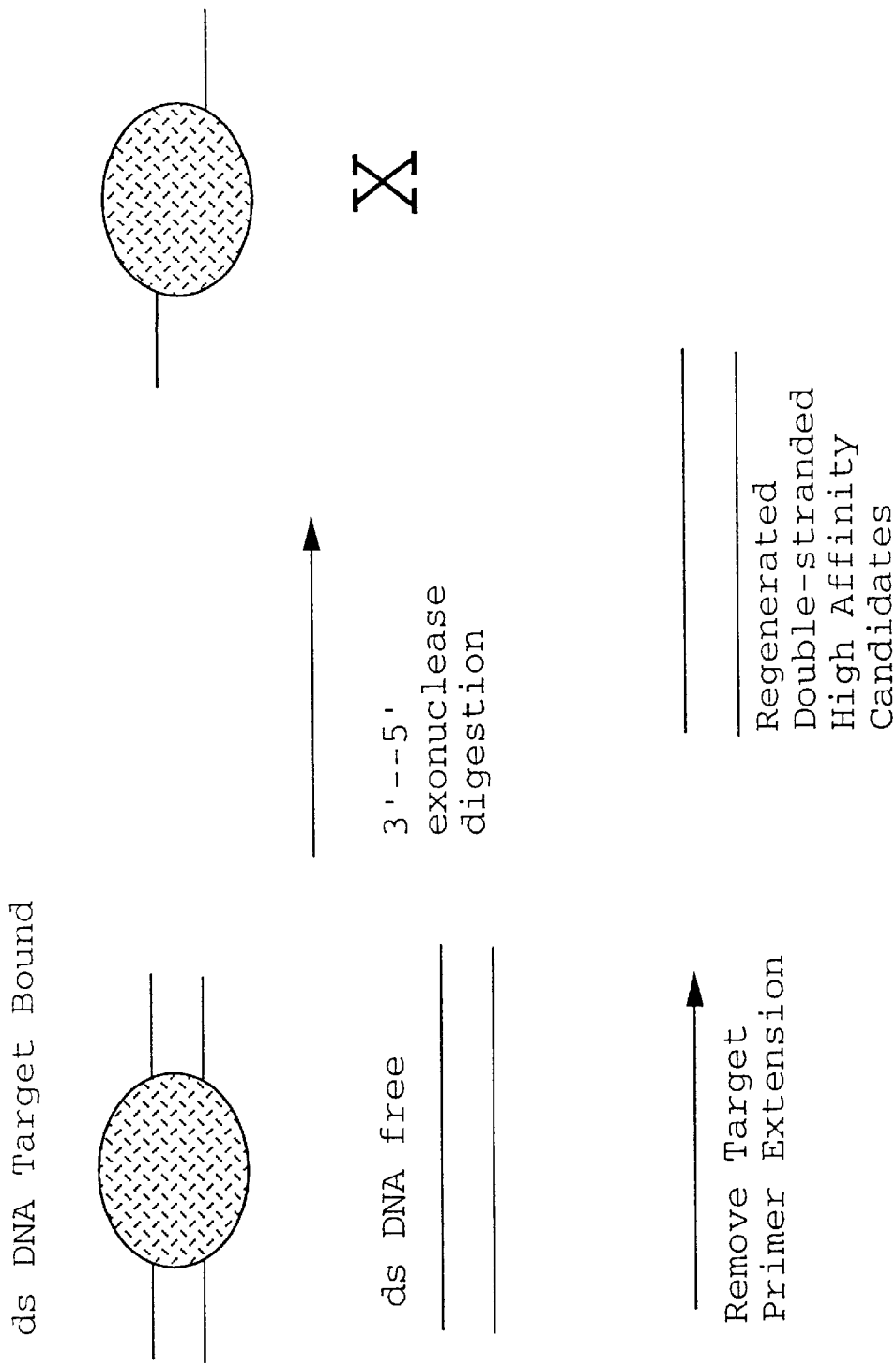
FIG. 26 illustrates one embodiment of the solution SELEX process wherein partitioning between oligonucleotides having high and low affinity to a target molecule is achieved by exonuclease inhibition and results in formation of a double-stranded nucleic acid population with high affinity for the target molecule.

Exonuclease inhibition may be used to isolate double-stranded ligands. Double-stranded nucleic acid ligands tightly bound to the target molecule will inhibit exonuclease hydrolysis at the 3' edge of the binding site. This results in a population of nucleic acid molecules resistant to hydrolysis that also contain a long single-stranded 5' overhang and a central base paired region (see FIG. 26). This nucleic acid molecule is a substrate for any polymerase, and incubation with polymerase will generate the double-stranded starting material. This molecule is amplified by PCR. Members of the nucleic acid candidate mixture that are not tightly bound to the target molecule are digested during the initial exonuclease step.

3'→5' hydrolysis of double-stranded nucleic acid is accomplished by incubation with any double-stranded specific 3'→5' exonuclease. Exonuclease III specifically hydrolyzes double-stranded DNA 3'→5' and is active in a variety of buffers, including 50 mM Tris-HCl (pH 8.0), 5 mM $MgCl_2$, 10 mM $\mu$-mercaptoethanol at 37° C.

EXAMPLE 25

Solution SELEX Method for Isolating Catalytic Nucleic Acids

Solution SELEX may be used to isolate catalytic nucleic acid sequences. This embodiment of the invention takes advantage of a linear to circular transformation to sort non-catalytic nucleic acids from catalytic nucleic acids.

Figure 27:
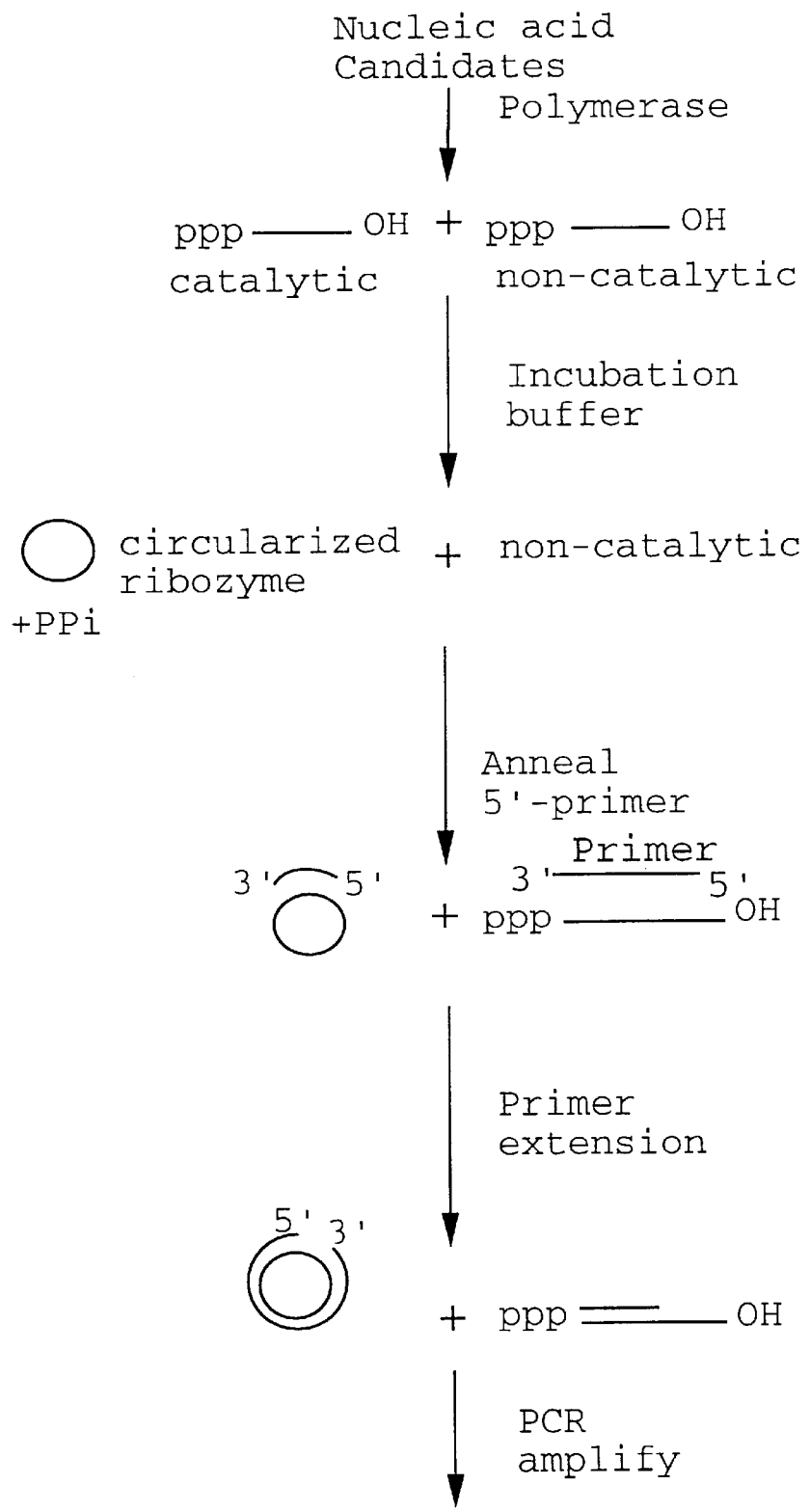
FIG. 27 illustrates one embodiment of the solution SELEX process wherein catalytic nucleic acids are selected and isolated.

As shown in FIG. 27, the PCR step may be exploited to screen the nucleic acid candidate mixture for catalytic members. Catalytic nucleic acids that either self-circularize, or alter their 5' or 3' ends to allow circularization with ligase, will amplify during PCR. The figure illustrates circle formation by catalytic members of the candidate mixture; the non-catalytic oligonucleotide members of the candidate mixture will remain linear. After circularization, the candidate mixture is incubated with a primer that anneals to the extreme 5' end. In this embodiment of the invention, only the circular oligonucleotide members will generate cDNA and be amplified during the PCR step.

This strategy isolates nucleic acids that either directly catalyze self-circularization or that modify their own ends so that the amplifiable form may be generated by incubation with ligase. As shown in FIG. 27, the unusual interaction of the cDNA primer with the 5' end of the oligonucleotides of the candidate mixture permits amplification of only the circular molecules. In a further embodiment of the method of the present invention, this strategy is modified to allow isolation of catalytic nucleic acids that catalyze novel reactions.

EXAMPLE 26

Automation of Solution SELEX

The automated solution SELEX protocol represents a modification of the technology used in the automated DNA synthesizer. The nucleic acid candidate mixture is attached to a solid support by either the biotin/avidin interaction or a variety of covalent chromatographic techniques (e.g., the condensation of modified nucleotides onto maleimide or citraconic anhydride supports). The bound nucleic acid candidate mixture provides a good substrate for targeting binding, and the column allows use of a single reaction vessel for the SELEX procedure. Primer extension inhibition is used to physically sort low and high affinity ligands. Low affinity nucleic acids may be degraded by incorporation of modified nucleotides during the first cDNA extension step that renders the cDNA degradable as described in Example 22, while high affinity ligands are copied into non-degradable cDNA and amplified by PCR. For additional rounds of solution SELEX, the PCR generated candidate mixture is purified or is transcribed into RNA and reattached to a second solid support, in the same or a new reaction vessel as desired. The process is repeated as necessary.

What is claimed is:

1. A nucleic acid ligand that photocrosslinks to a target molecule that is associated with a disease state, said target molecule is a protein, wherein said nucleic acid ligand is comprised of a non-naturally occurring nucleic acid having a specific binding affinity for said target molecule, wherein said target molecule is not a nucleic acid binding molecule, and wherein said nucleic acid ligand is not a nucleic acid having the known physiological function of being bound by the target molecule, identified by the process of:
    a) identifying a nucleic acid ligand that photocrosslinks to a target molecule that is associated with said disease state from a candidate mixture of nucleic acids, wherein each member of said candidate mixture contains a photoreactive group, said method comprising:
        i) contacting said candidate mixture of nucleic acids with a first biological substance obtained from a source associated with said disease state which is suspected of containing the target molecule that is associated with said disease state, wherein nucleic acids having an increased affinity to molecules of said first biological substance relative to the candidate mixture form nucleic acid-target molecule complexes with the target molecule;
        ii) irradiating said complexes, wherein said nucleic acids and target molecules photocrosslink;
        iii) partitioning the photocrosslinked nucleic acid-target molecule complexes from the remainder of the candidate mixture; and
        iv) identifying nucleic acid ligands that photocrosslink to said target molecule;
    b) contacting a second biological substance of the same type as the first biological substance, and obtained from a source not associated with said disease state and which does not contain said target molecule that is associated with said disease state with said nucleic acid ligands identified in step iv), wherein the nucleic acids with affinity to the molecules in the second biological substance that are not associated with said disease state are removed; and
    c) amplifying the remaining nucleic acids to yield a mixture of nucleic acids enriched for nucleic acids with relatively higher affinity and specificity for binding to said target molecule that is associated with said disease state, whereby a nucleic acid ligand that photocrosslinks to a target molecule that is associated with a disease state in a biological substance is identified.

2. The nucleic acid ligand of claim 1, wherein the nucleic acid ligand is comprised of one or more of the photoreactive groups selected from the group consisting of 5-bromouracil, 5-iodouracil, 5-bromovinyluracil, 5-iodovinyluracil, 5-azidouracil, 4-thiouracil, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-azidoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-bromodeoxyuracil, 8-bromo-2'-deoxyadenine, 5-iodo-2'-deoxyuracil, 5-iodo-2'-deoxycytosine, 5-[(4-azidophenacyl)thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine.

3. A nucleic acid ligand that photocrosslinks to a target molecule that is associated with a disease state, wherein said target molecule is protein, wherein said nucleic acid ligand is comprised of a non-naturally occurring nucleic acid having a specific binding affinity for said target molecule, wherein said target molecule is not a nucleic acid binding molecule, and wherein said nucleic acid ligand is not a nucleic acid having the known physiological function of being bound by the target molecule, identified by the process of:
    a) identifying a nucleic acid ligand that photocrosslinks to a target molecule that is associated with the disease state from a candidate mixture of nucleic acids, said method comprising:
        i) contacting said candidate mixture of nucleic acids with a first biological substance obtained from a source associated with said disease state which is suspected of containing the target molecule that is associated with said disease state, wherein nucleic acids having an increased affinity to molecules of said first biological substance relative to the candidate mixture form nucleic acid-target molecule complexes with the target molecule;
        ii) partitioning the complexed increased affinity nucleic acids from the remainder of the candidate mixture;
        iii) amplifying the increased affinity nucleic acids to yield a ligand-enriched mixture of nucleic acids;
        iv) incorporating photoreactive groups into said amplified increased affinity nucleic acids;
        v) contacting said increased affinity nucleic acids with a biological substance obtained from a source associated with said disease state which is suspected of containing the target molecule that is associated with said disease state;
        vi) irradiating said increased affinity nucleic acids, wherein said nucleic acid-target molecule complexes photocrosslink;
        vii) partitioning the photocrosslinked nucleic acid-target molecule complexes from the remainder of the candidate mixture; and
        viii) identifying nucleic acid ligands that photocrosslink to the target molecule;
    b) contacting a second biological substance of the same type as the first biological substance, and obtained from a source not associated with said disease state and which does not contain said target molecule that is associated with said disease state with said nucleic acid ligand identified in step vii), wherein the nucleic acids with affinity to molecules not associated with said disease state are removed; and;

c) amplifying the remaining nucleic acids to yield a mixture of nucleic acids enriched for nucleic acids with relatively higher affinity and specificity for binding to said target molecule that is associated with said disease state, whereby a nucleic acid ligand that photocrosslinks to a target molecule that is associated with a disease state in a biological substance is identified.

4. The nucleic acid ligand of claim 3, wherein the nucleic acid ligand is comprised of one or more of the photoreactive groups selected from the group consisting of 5-bromouracil, 5-iodouracil, 5-bromovinyluracil, 5-iodovinyluracil, 5-azidouracil, 4-thiouracil, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-azidoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-bromodeoxyuracil, 8-bromo-2'-deoxyadenine, 5-iodo-2'-deoxyuracil, 5-iodo-2'-deoxycytosine, 5-[(4-azidophenacyl)thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine.

5. The method of claim 1, wherein said first biological substance is serum from a patient with a disease, and said second biological substance is serum from a patient not having said disease.

6. The method of claim 1, wherein said first biological substance is an abnormal cell, and said second biological substance is a normal cell of the same type.

7. The method of claim 3, wherein said first biological substance is serum from a patient with a disease, and said second biological substance is serum from a patient not having said disease.

8. The method of claim 3, wherein said first biological substance is an abnormal cell, and said second biological substance is a normal cell of the same type.

* * * * *